(12) United States Patent
Al-Ali et al.

(10) Patent No.: US 10,925,550 B2
(45) Date of Patent: *Feb. 23, 2021

(54) MEDICAL MONITORING HUB

(71) Applicant: MASIMO CORPORATION, Irvine, CA (US)

(72) Inventors: Ammar Al-Ali, San Juan Capistrano, CA (US); Bilal Muhsin, San Clemente, CA (US); Massi Joe E. Kiani, Laguna Niguel, CA (US); Anand Sampath, Irvine, CA (US); Peter Scott Housel, Irvine, CA (US); Eric Karl Kinast, Santa Ana, CA (US)

(73) Assignee: Masimo Corporation, Irvine, CA (US)

( * ) Notice: Subject to any disclaimer, the term of this patent is extended or adjusted under 35 U.S.C. 154(b) by 1105 days.

This patent is subject to a terminal disclaimer.

(21) Appl. No.: 15/214,276

(22) Filed: Jul. 19, 2016

(65) Prior Publication Data

US 2016/0327984 A1    Nov. 10, 2016

Related U.S. Application Data

(62) Division of application No. 13/651,167, filed on Oct. 12, 2012, now Pat. No. 9,436,645.

(Continued)

(51) Int. Cl.
*A61B 5/00* (2006.01)
*A61B 5/0205* (2006.01)
(Continued)

(52) U.S. Cl.
CPC ............ *A61B 5/743* (2013.01); *A61B 5/0002* (2013.01); *A61B 5/002* (2013.01); *A61B 5/0022* (2013.01);
(Continued)

(58) Field of Classification Search
None
See application file for complete search history.

(56) References Cited

U.S. PATENT DOCUMENTS 3,646,606 A    2/1972    Buxton et al.
3,690,313 A    9/1972    Weber et al.
(Continued)

FOREIGN PATENT DOCUMENTS

EP    735499    10/1996
EP    1 110 503    6/2001
(Continued)

OTHER PUBLICATIONS

US 8,845,543 B2, 09/2014, Diab et al. (withdrawn)
(Continued)

*Primary Examiner* — Rachelle L Reichert
(74) *Attorney, Agent, or Firm* — Knobbe Martens Olson & Bear LLP

(57) ABSTRACT

The present disclosure includes a medical monitoring hub as the center of monitoring for a monitored patient. The hub includes configurable medical ports and serial ports for communicating with other medical devices in the patient's proximity. Moreover, the hub communicates with a portable patient monitor. The monitor, when docked with the hub provides display graphics different from when undocked, the display graphics including anatomical information. The hub assembles the often vast amount of electronic medical data, associates it with the monitored patient, and in some embodiments, communicates the data to the patient's medical records.

10 Claims, 46 Drawing Sheets

Related U.S. Application Data

(60) Provisional application No. 61/703,773, filed on Sep. 20, 2012, provisional application No. 61/597,120, filed on Feb. 9, 2012, provisional application No. 61/547,577, filed on Oct. 14, 2011, provisional application No. 61/547,017, filed on Oct. 13, 2011.

(51) Int. Cl.

| | | |
|---|---|---|
| *A61M 16/00* | (2006.01) | |
| *A61M 5/172* | (2006.01) | |
| *G16H 40/63* | (2018.01) | |
| *G16H 10/60* | (2018.01) | |
| *G06F 13/40* | (2006.01) | |
| *A61B 5/0402* | (2006.01) | |
| *A61B 5/0476* | (2006.01) | |
| *A61B 7/00* | (2006.01) | |
| *G06F 1/16* | (2006.01) | |
| *A61B 5/021* | (2006.01) | |
| *A61B 5/08* | (2006.01) | |
| *A61B 5/1455* | (2006.01) | |
| *A61B 5/01* | (2006.01) | |
| *A61B 5/024* | (2006.01) | |
| *A61B 5/145* | (2006.01) | |

(52) U.S. Cl.
CPC ........ *A61B 5/02055* (2013.01); *A61B 5/0402* (2013.01); *A61B 5/0476* (2013.01); *A61B 5/4821* (2013.01); *A61B 5/4836* (2013.01); *A61B 5/4866* (2013.01); *A61B 5/4875* (2013.01); *A61B 5/742* (2013.01); *A61B 5/746* (2013.01); *A61B 5/7425* (2013.01); *A61B 7/003* (2013.01); *A61M 5/172* (2013.01); *A61M 16/0051* (2013.01); *A61M 16/021* (2017.08); *G06F 1/1632* (2013.01); *G06F 13/4081* (2013.01); *G16H 10/60* (2018.01); *G16H 40/63* (2018.01); *A61B 5/01* (2013.01); *A61B 5/021* (2013.01); *A61B 5/02416* (2013.01); *A61B 5/0816* (2013.01); *A61B 5/14539* (2013.01); *A61B 5/14551* (2013.01); *A61B 2560/0209* (2013.01); *A61B 2560/0214* (2013.01); *A61B 2560/0475* (2013.01); *A61B 2562/08* (2013.01); *A61B 2562/222* (2013.01); *A61B 2562/227* (2013.01); *A61M 2205/18* (2013.01); *A61M 2205/3368* (2013.01); *A61M 2205/3375* (2013.01); *A61M 2205/3561* (2013.01); *A61M 2205/3569* (2013.01); *A61M 2205/3584* (2013.01); *A61M 2205/3592* (2013.01); *A61M 2205/505* (2013.01); *A61M 2209/086* (2013.01); *A61M 2230/04* (2013.01); *A61M 2230/10* (2013.01); *A61M 2230/201* (2013.01); *A61M 2230/205* (2013.01); *A61M 2230/208* (2013.01); *A61M 2230/30* (2013.01); *A61M 2230/42* (2013.01); *A61M 2230/50* (2013.01)

(56) References Cited

U.S. PATENT DOCUMENTS

| | | |
|---|---|---|
| 3,810,102 A | 5/1974 | Parks, III et al. |
| 3,815,583 A | 6/1974 | Scheidt |
| 3,972,320 A | 8/1976 | Kalman |
| 3,978,849 A | 9/1976 | Geneen |
| 4,108,166 A | 8/1978 | Schmid |
| 4,231,354 A | 11/1980 | Kurtz et al. |
| 4,589,415 A | 5/1986 | Haaga |
| 4,662,378 A | 5/1987 | Thomis |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,309,918 A | 5/1994 | Schraag |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Schimizu |
| 5,375,604 A | 12/1994 | Kelly |
| 5,377,676 A | 1/1995 | Vari et al. |
| 5,400,794 A | 3/1995 | Gorman |
| 5,406,952 A | 4/1995 | Barnes et al. |
| D357,982 S | 5/1995 | Dahl et al. |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,537,289 A | 7/1996 | Dahl |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,953 A | 6/1997 | Bishop et al. |
| 5,640,967 A | 6/1997 | Fine et al. |
| 5,645,440 A | 7/1997 | Tobler et al. |
| 5,671,914 A | 9/1997 | Kalkhoran et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang et al. |
| 5,724,580 A | 3/1998 | Levin et al. |
| 5,724,983 A | 3/1998 | Selker et al. |
| 5,725,308 A | 3/1998 | Smith et al. |
| 5,726,440 A | 3/1998 | Kalkhoran et al. |

(56) References Cited

U.S. PATENT DOCUMENTS

| | | |
|---|---|---|
| 5,734,739 A | 3/1998 | Sheehan et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,813,403 A | 9/1998 | Soller et al. |
| 5,822,544 A | 10/1998 | Chaco et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| 5,876,351 A | 3/1999 | Rohde |
| 5,885,214 A | 3/1999 | Monroe et al. |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,931,791 A | 8/1999 | Saltzstein et al. |
| 5,934,925 A | 8/1999 | Tobler et al. |
| 5,940,182 A | 8/1999 | Lepper, Jr. et al. |
| 5,942,986 A | 8/1999 | Shabot et al. |
| 5,987,343 A | 11/1999 | Kinast |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,010,937 A | 1/2000 | Karam et al. |
| 6,011,986 A | 1/2000 | Diab et al. |
| 6,014,345 A | 1/2000 | Malone |
| 6,014,346 A | 1/2000 | Malone |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang |
| 6,036,642 A | 3/2000 | Diab et al. |
| 6,036,718 A | 3/2000 | Ledford et al. |
| 6,040,578 A | 3/2000 | Malin et al. |
| 6,045,509 A | 4/2000 | Caro et al. |
| 6,045,527 A | 4/2000 | Appelbaum et al. |
| 6,057,758 A | 5/2000 | Dempsey et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,175,752 B1 | 1/2001 | Say et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,241,684 B1 | 6/2001 | Amano et al. |
| 6,251,113 B1 | 6/2001 | Appelbaum |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,364,834 B1 | 4/2002 | Reuss et al. |
| 6,364,839 B1 | 4/2002 | Little et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,407,335 B1 | 6/2002 | Franklin-Lees |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 | 10/2002 | Boesen |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,516,289 B2 | 2/2003 | David et al. |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,551,243 B2 | 4/2003 | Bocionek et al. |

(56) References Cited

U.S. PATENT DOCUMENTS

| | | |
|---|---|---|
| 6,570,592 B1 | 5/2003 | Sajdak et al. |
| 6,578,428 B1 | 6/2003 | Dromms et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,641,533 B2 | 11/2003 | Causey et al. |
| 6,643,530 B2 | 11/2003 | Diab et al. |
| 6,646,556 B1 | 11/2003 | Smith |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Kiani et al. |
| 6,661,161 B1 | 12/2003 | Lanzo et al. |
| 6,663,570 B2 | 12/2003 | Mott et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,707,476 B1 | 3/2004 | Hochstedler |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,746,406 B2 | 6/2004 | Lia et al. |
| 6,750,463 B1 | 6/2004 | Riley |
| 6,751,492 B2 | 6/2004 | Ben-haim |
| 6,760,607 B2 | 7/2004 | Al-Ali |
| 6,766,188 B2 | 7/2004 | Soller |
| 6,770,028 B1 | 8/2004 | Ali et al. |
| 6,771,994 B2 | 8/2004 | Kiani et al. |
| 6,773,396 B2 | 8/2004 | Flach et al. |
| 6,783,492 B2 | 8/2004 | Dominguez |
| 6,788,965 B2 | 9/2004 | Ruchti et al. |
| 6,790,178 B1 | 9/2004 | Mault et al. |
| 6,792,300 B1 | 9/2004 | Diab et al. |
| 6,795,724 B2 | 9/2004 | Hogan |
| 6,796,186 B2 | 9/2004 | Lia et al. |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,241 B2 | 11/2004 | Grubisic |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,839,584 B2 | 1/2005 | Makarewicz et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,876,931 B2 | 4/2005 | Lorenz et al. |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,952,340 B2 | 10/2005 | Son |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,983,179 B2 | 1/2006 | Ben-haim |
| 6,985,764 B2 | 1/2006 | Mason et al. |
| 6,988,989 B2 | 1/2006 | Weiner et al. |
| 6,990,087 B2 | 1/2006 | Rao et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,884 B2 | 2/2006 | Ulmsten |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,010,336 B2 | 3/2006 | Lorenz et al. |
| 7,015,451 B2 | 3/2006 | Dalke et al. |
| 7,024,233 B2 | 4/2006 | Ali et al. |
| 7,025,729 B2 | 4/2006 | De Chazal et al. |
| 7,027,849 B2 | 4/2006 | Al-Ali |
| 7,030,749 B2 | 4/2006 | Al-Ali |
| 7,033,761 B2 | 4/2006 | Shafer |
| 7,035,686 B2 | 4/2006 | Hogan |
| 7,039,449 B2 | 5/2006 | Al-Ali |
| 7,041,060 B2 | 5/2006 | Flaherty et al. |
| 7,044,918 B2 | 5/2006 | Diab |
| 7,044,930 B2 | 5/2006 | Stromberg |
| 7,048,687 B1 | 5/2006 | Reuss et al. |
| 7,059,769 B1 | 6/2006 | Potega |
| 7,063,666 B2 | 6/2006 | Weng et al. |
| 7,067,893 B2 | 6/2006 | Mills et al. |
| 7,079,035 B2 | 7/2006 | Bock et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,229,415 B2 | 6/2007 | Schwartz |
| 7,239,905 B2 | 7/2007 | Kiani-Azarbayjany et al. |
| 7,241,287 B2 | 7/2007 | Shehada et al. |
| 7,244,251 B2 | 7/2007 | Shehada et al. |
| 7,245,373 B2 | 7/2007 | Soller et al. |
| 7,245,953 B1 | 7/2007 | Parker |
| 7,252,659 B2 | 8/2007 | Shehada et al. |
| 7,254,429 B2 | 8/2007 | Schurman et al. |
| 7,254,431 B2 | 8/2007 | Al-Ali |
| 7,254,433 B2 | 8/2007 | Diab et al. |

(56) References Cited

U.S. PATENT DOCUMENTS

| | | | |
|---|---|---|---|
| 7,254,434 B2 | 8/2007 | Schulz et al. |
| 7,256,708 B2 | 8/2007 | Rosenfeld |
| 7,261,697 B2 | 8/2007 | Berstein |
| 7,264,616 B2 | 9/2007 | Shehada et al. |
| 7,267,671 B2 | 9/2007 | Shehada et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,285,090 B2 | 10/2007 | Stivoric |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,543 B2 | 12/2007 | Rosenfeld |
| 7,313,423 B2 | 12/2007 | Griffin et al. |
| 7,314,446 B2 | 1/2008 | Byrd et al. |
| 7,315,825 B2 | 1/2008 | Rosenfeld |
| 7,321,862 B2 | 1/2008 | Rosenfeld |
| 7,322,971 B2 | 1/2008 | Shehada et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,178 B2 | 4/2008 | Ziel et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,378,975 B1 | 5/2008 | Smith |
| 7,382,247 B2 | 6/2008 | Welch et al. |
| 7,383,070 B2 | 6/2008 | Diab et al. |
| 7,390,299 B2 | 6/2008 | Weiner et al. |
| 7,395,216 B2 | 7/2008 | Rosenfeld |
| 7,411,509 B2 | 8/2008 | Rosenfeld |
| 7,413,546 B2 | 8/2008 | Agutter et al. |
| 7,415,297 B2 | 8/2008 | Al-Ali et al. |
| 7,419,483 B2 | 9/2008 | Shehada |
| 7,428,432 B2 | 9/2008 | Ali et al. |
| 7,433,827 B2 | 10/2008 | Rosenfeld |
| 7,438,683 B2 | 10/2008 | Al-Ali et al. |
| 7,439,856 B2 | 10/2008 | Weiner et al. |
| 7,440,786 B2 | 10/2008 | Hockersmith et al. |
| 7,440,787 B2 | 10/2008 | Diab |
| 7,454,240 B2 | 11/2008 | Diab et al. |
| 7,454,359 B2 | 11/2008 | Rosenfeld |
| 7,454,360 B2 | 11/2008 | Rosenfeld |
| 7,462,151 B2 | 12/2008 | Childre et al. |
| 7,467,002 B2 | 12/2008 | Weber et al. |
| 7,467,094 B2 | 12/2008 | Rosenfeld |
| 7,469,157 B2 | 12/2008 | Diab et al. |
| 7,471,969 B2 | 12/2008 | Diab et al. |
| 7,471,971 B2 | 12/2008 | Diab et al. |
| 7,475,019 B2 | 1/2009 | Rosenfeld |
| 7,483,729 B2 | 1/2009 | Al-Ali et al. |
| 7,483,730 B2 | 1/2009 | Diab et al. |
| 7,489,250 B2 | 2/2009 | Bock et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,497,828 B1 | 3/2009 | Wilk et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,551,717 B2 | 6/2009 | Tome et al. |
| 7,559,520 B2 | 7/2009 | Quijano et al. |
| 7,563,110 B2 | 7/2009 | Al-Ali et al. |
| 7,577,475 B2 | 8/2009 | Consentino et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,597,665 B2 | 10/2009 | Wilk et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,639,145 B2 | 12/2009 | Lawson et al. |
| 7,640,140 B2 | 12/2009 | Ruchti et al. |
| 7,647,083 B2 | 1/2010 | Al-Ali et al. |
| 7,650,291 B2 | 1/2010 | Rosenfeld |
| D609,193 S | 2/2010 | Al-Ali et al. |
| 7,654,966 B2 | 2/2010 | Westinskow et al. |
| 7,684,845 B2 | 3/2010 | Juan |
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,740,590 B2 | 6/2010 | Bernstein |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,772,799 B2 | 8/2010 | Wu |
| 7,774,060 B2 | 8/2010 | Westenskow et al. |
| 7,778,851 B2 | 8/2010 | Schoenberg et al. |
| 7,791,155 B2 | 9/2010 | Diab |
| 7,794,407 B2 | 9/2010 | Rothenberg |
| 7,801,581 B2 | 9/2010 | Diab |
| 7,806,830 B2 | 10/2010 | Bernstein |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |

(56) References Cited

U.S. PATENT DOCUMENTS

| | | |
|---|---|---|
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Al-Ali et al. |
| 7,991,463 B2 | 8/2011 | Kelleher et al. |
| 7,991,625 B2 | 8/2011 | Rosenfeld |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| 8,094,013 B1 | 1/2012 | Lee et al. |
| 8,107,397 B1 | 1/2012 | Bagchi et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,182,429 B2 | 5/2012 | Mason |
| 8,182,443 B1 | 5/2012 | Kiani |
| 8,185,180 B2 | 5/2012 | Diab et al. |
| 8,190,223 B2 | 5/2012 | Al-ali et al. |
| 8,190,227 B2 | 5/2012 | Diab et al. |
| 8,200,308 B2 | 6/2012 | Zhang et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,294,588 B2 | 10/2012 | Fisher et al. |
| 8,294,716 B2 | 10/2012 | Lord et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| RE43,860 E | 12/2012 | Parker |
| 7,899,507 C1 | 12/2012 | Al-Ali et al. |
| 8,326,649 B2 | 12/2012 | Rosenfeld |
| 8,328,793 B2 | 12/2012 | Birkenbach |
| 8,337,403 B2 | 12/2012 | Al-Ali et al. |
| 6,970,792 C1 | 1/2013 | Diab |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| D679,018 S | 3/2013 | Fullerton et al. |
| 8,388,353 B2 | 3/2013 | Kiani et al. |
| 8,399,822 B2 | 3/2013 | Al-Ali |
| 8,401,602 B2 | 3/2013 | Kiani |
| 8,401,874 B2 | 3/2013 | Rosenfeld |
| 8,405,608 B2 | 3/2013 | Al-Ali et al. |
| 6,463,311 C1 | 4/2013 | Diab et al. |
| 7,377,899 C1 | 4/2013 | Weber et al. |
| 8,190,223 C1 | 4/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 7,962,188 C1 | 6/2013 | Kiani et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,167 B2 | 7/2013 | Buxton |
| 8,489,364 B2 | 7/2013 | Weber et al. |
| 8,498,684 B2 | 7/2013 | Weber et al. |
| 8,504,128 B2 | 8/2013 | Blank et al. |
| 8,506,480 B2 | 8/2013 | Banet et al. |
| 8,509,867 B2 | 8/2013 | Workman et al. |
| 8,515,509 B2 | 8/2013 | Bruinsma et al. |
| 7,024,233 C1 | 9/2013 | Al Ali et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |

(56) References Cited

U.S. PATENT DOCUMENTS

| | | |
|---|---|---|
| 8,565,847 B2 | 10/2013 | Buxton et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 7,438,683 C1 | 11/2013 | Al-Ali et al. |
| 8,180,420 C1 | 11/2013 | Diab et al. |
| 8,577,431 B2 | 11/2013 | Lamego et al. |
| 8,578,082 B2 | 11/2013 | Medina et al. |
| 8,579,813 B2 | 11/2013 | Causey |
| 8,581,732 B2 | 11/2013 | Al-Ali et al. |
| 8,588,880 B2 | 11/2013 | Abdul-Hafiz et al. |
| 8,588,924 B2 | 11/2013 | Dion |
| 6,684,090 C1 | 12/2013 | Al Ali et al. |
| 7,499,835 C1 | 12/2013 | Weber et al. |
| 8,150,487 C1 | 12/2013 | Diab et al. |
| 8,597,287 B2 | 12/2013 | Benamou et al. |
| 8,600,467 B2 | 12/2013 | Al-Ali et al. |
| 8,600,777 B2 | 12/2013 | Schoenberg |
| 8,606,342 B2 | 12/2013 | Diab |
| 8,620,678 B2 | 12/2013 | Gotlib |
| 7,530,955 C1 | 1/2014 | Diab et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 7,880,606 C1 | 2/2014 | Al-Ali |
| 8,641,631 B2 | 2/2014 | Sierra et al. |
| 8,652,060 B2 | 2/2014 | Al-Ali |
| 7,440,787 C1 | 3/2014 | Diab |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,128,572 C1 | 4/2014 | Diab et al. |
| 8,688,183 B2 | 4/2014 | Bruinsma et al. |
| 8,690,771 B2 | 4/2014 | Wekell et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 7,215,984 C1 | 5/2014 | Diab et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 6,002,952 C1 | 6/2014 | Diab et al. |
| 8,740,792 B1 | 6/2014 | Kiani et al. |
| 8,753,274 B2 | 6/2014 | Ziv et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,758,020 B2 | 6/2014 | Burdea et al. |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,950 B2 | 7/2014 | Larsen et al. |
| 8,801,613 B2 | 8/2014 | Al-Ali et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,866,620 B2 | 10/2014 | Amir |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,873,035 B2 | 10/2014 | Yang et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,907,287 B2 | 12/2014 | Vanderpohl |
| 8,909,310 B2 | 12/2014 | Lamego et al. |
| 8,909,330 B2 | 12/2014 | McCombie et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,951,248 B2 | 2/2015 | Messerly et al. |
| 8,956,292 B2 | 2/2015 | Wekell |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,057,689 B2 | 6/2015 | Soller |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,291 B2 | 8/2015 | Soller |
| 9,095,316 B2 | 8/2015 | Welch et al. |
| 9,104,789 B2 | 8/2015 | Gross et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,125,578 B2 | 9/2015 | Grunwald |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |

(56) References Cited

U.S. PATENT DOCUMENTS

| | | |
|---|---|---|
| 9,192,351 B1 | 11/2015 | Telfort et al. |
| 9,195,385 B2 | 11/2015 | Al-Ali et al. |
| D745,167 S | 12/2015 | Canas et al. |
| 6,699,194 C1 | 12/2015 | Diab et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,262,586 B2 | 2/2016 | Steiger et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,414,784 B1 | 8/2016 | Berme et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,529,762 B2 | 12/2016 | Gisler et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Al-Ali et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 6,157,850 C1 | 7/2018 | Diab et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 7,530,955 C2 | 10/2018 | Diab et al. |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| D833,624 S | 11/2018 | DeJong et al. |
| 10,123,726 B2 | 11/2018 | Al-Ali et al. |
| 10,130,289 B2 | 11/2018 | Al-Ali et al. |

(56) References Cited

U.S. PATENT DOCUMENTS

| | | |
|---|---|---|
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,478,107 B2 | 11/2019 | Kiani et al. |
| 10,512,436 B2 | 12/2019 | Muhsin et al. |
| 10,608,817 B2 | 3/2020 | Haider et al. |
| 2001/0011355 A1 | 8/2001 | Kawai |
| 2001/0031922 A1 | 10/2001 | Weng et al. |
| 2001/0034477 A1 | 10/2001 | Mansfield et al. |
| 2001/0039199 A1 | 11/2001 | Shinzaki |
| 2001/0039483 A1 | 11/2001 | Brand et al. |
| 2001/0046366 A1 | 11/2001 | Susskind |
| 2001/0046862 A1 | 11/2001 | Coppinger et al. |
| 2001/0055978 A1 | 12/2001 | Herrod et al. |
| 2002/0010401 A1 | 1/2002 | Bushmakin et al. |
| 2002/0032386 A1 | 3/2002 | Sackner et al. |
| 2002/0038392 A1 | 3/2002 | De La Huerga |
| 2002/0045836 A1 | 4/2002 | Alkawwas |
| 2002/0052311 A1 | 5/2002 | Solomon et al. |
| 2002/0058864 A1 | 5/2002 | Mansfield et al. |
| 2002/0063690 A1 | 5/2002 | Chung et al. |
| 2002/0133080 A1 | 9/2002 | Apruzzese et al. |
| 2002/0140675 A1 | 10/2002 | Ali et al. |
| 2002/0165462 A1 | 11/2002 | Westbrook et al. |
| 2002/0177758 A1 | 11/2002 | Schoenberg |
| 2002/0198445 A1 | 12/2002 | Dominguez et al. |
| 2003/0013975 A1 | 1/2003 | Kiani |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0144582 A1 | 7/2003 | Cohen et al. |
| 2003/0156288 A1 | 8/2003 | Barnum et al. |
| 2003/0158466 A1 | 8/2003 | Lynn et al. |
| 2003/0212312 A1 | 11/2003 | Coffin, IV et al. |
| 2003/0216670 A1 | 11/2003 | Smith |
| 2004/0013647 A1 | 1/2004 | Solomon et al. |
| 2004/0122787 A1 | 6/2004 | Avinash et al. |
| 2004/0126007 A1 | 7/2004 | Ziel et al. |
| 2004/0139571 A1 | 7/2004 | Chang et al. |
| 2004/0147818 A1 | 7/2004 | Levy et al. |
| 2004/0186357 A1 | 9/2004 | Soderberg et al. |
| 2004/0230118 A1 | 11/2004 | Shehada et al. |
| 2004/0230132 A1 | 11/2004 | Shehada et al. |
| 2004/0230179 A1 | 11/2004 | Shehada et al. |
| 2004/0243017 A1 | 12/2004 | Causevic |
| 2004/0249670 A1 | 12/2004 | Noguchi et al. |
| 2004/0254431 A1 | 12/2004 | Shehada et al. |
| 2004/0254432 A1 | 12/2004 | Shehada et al. |
| 2004/0267103 A1 | 12/2004 | Li et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0055276 A1 | 3/2005 | Kiani et al. |
| 2005/0065417 A1 | 3/2005 | Ali et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1 | 6/2005 | Mack |
| 2005/0125256 A1 | 6/2005 | Schoenberg |
| 2005/0164933 A1 | 7/2005 | Tymianski et al. |
| 2005/0171444 A1 | 8/2005 | Ono et al. |
| 2005/0188083 A1* | 8/2005 | Biondi ............... A61M 16/0051 709/224 |
| 2005/0191294 A1 | 9/2005 | Arap et al. |
| 2005/0261598 A1 | 11/2005 | Banet et al. |
| 2005/0268401 A1 | 12/2005 | Dixon |
| 2005/0277872 A1 | 12/2005 | Colby et al. |
| 2006/0049936 A1 | 3/2006 | Collins |
| 2006/0052718 A1 | 3/2006 | Parnagian |
| 2006/0058647 A1 | 3/2006 | Strommer et al. |
| 2006/0073719 A1 | 4/2006 | Kiani |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0161054 A1 | 7/2006 | Reuss et al. |
| 2006/0189871 A1 | 8/2006 | Al-Ali et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |

(56) References Cited

U.S. PATENT DOCUMENTS

| | | |
|---|---|---|
| 2007/0000490 A1 | 1/2007 | DeVries et al. |
| 2007/0002533 A1 | 1/2007 | Kogan et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0073116 A1 | 3/2007 | Kiani et al. |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0156033 A1 | 7/2007 | Causey et al. |
| 2007/0157285 A1 | 7/2007 | Frank et al. |
| 2007/0159332 A1 | 7/2007 | Koblasz |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0232941 A1 | 10/2007 | Rabinovich |
| 2007/0244377 A1 | 10/2007 | Cozad et al. |
| 2007/0244724 A1 | 10/2007 | Pendergast et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2007/0282478 A1 | 12/2007 | Al-Ali et al. |
| 2007/0293906 A1 | 12/2007 | Cowan et al. |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0039701 A1 | 2/2008 | Ali et al. |
| 2008/0053438 A1 | 3/2008 | DeVries et al. |
| 2008/0058657 A1 | 3/2008 | Schwartz et al. |
| 2008/0064965 A1 | 3/2008 | Jay et al. |
| 2008/0090626 A1 | 4/2008 | Griffin et al. |
| 2008/0091089 A1 | 4/2008 | Guillory et al. |
| 2008/0091090 A1 | 4/2008 | Guillory et al. |
| 2008/0091471 A1 | 4/2008 | Michon et al. |
| 2008/0094228 A1 | 4/2008 | Welch et al. |
| 2008/0097167 A1 | 4/2008 | Yudkovitch et al. |
| 2008/0099366 A1 | 5/2008 | Niemiec et al. |
| 2008/0108884 A1 | 5/2008 | Kiani |
| 2008/0119412 A1 | 5/2008 | Tymianski et al. |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0208912 A1 | 8/2008 | Garibaldi |
| 2008/0215627 A1 | 9/2008 | Higgins et al. |
| 2008/0221396 A1 | 9/2008 | Garces et al. |
| 2008/0221418 A1 | 9/2008 | Al-Ali et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0300020 A1 | 12/2008 | Nishizawa et al. |
| 2008/0319275 A1 | 12/2008 | Chiu et al. |
| 2008/0319354 A1 | 12/2008 | Bell et al. |
| 2009/0005651 A1 | 1/2009 | Ward et al. |
| 2009/0018808 A1 | 1/2009 | Bronstein et al. |
| 2009/0024008 A1 | 1/2009 | Brunner et al. |
| 2009/0036759 A1 | 2/2009 | Ault et al. |
| 2009/0043172 A1 | 2/2009 | Zagorchev et al. |
| 2009/0052623 A1 | 2/2009 | Tome et al. |
| 2009/0054735 A1 | 2/2009 | Higgins et al. |
| 2009/0054743 A1 | 2/2009 | Stewart |
| 2009/0062682 A1 | 3/2009 | Bland et al. |
| 2009/0069642 A1 | 3/2009 | Gao et al. |
| 2009/0093687 A1 | 4/2009 | Telfort et al. |
| 2009/0095926 A1 | 4/2009 | MacNeish, III |
| 2009/0099480 A1 | 4/2009 | Salgo et al. |
| 2009/0119330 A1 | 5/2009 | Sampath et al. |
| 2009/0119843 A1 | 5/2009 | Salgo |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1 | 7/2009 | Li |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0221887 A1 | 9/2009 | Mannheimer et al. |
| 2009/0226372 A1 | 9/2009 | Ruoslahti et al. |
| 2009/0247984 A1 | 10/2009 | Lamego et al. |
| 2009/0264778 A1 | 10/2009 | Markowitz et al. |
| 2009/0275813 A1 | 11/2009 | Davis |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0309755 A1 | 12/2009 | Williamson |
| 2009/0322540 A1 | 12/2009 | Richardson et al. |
| 2009/0326386 A1 | 12/2009 | Sethi et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0060747 A1 | 3/2010 | Woodman |
| 2010/0069725 A1 | 3/2010 | Al-Ali |
| 2010/0081895 A1 | 4/2010 | Zand |
| 2010/0099964 A1 | 4/2010 | O'Reilly et al. |
| 2010/0114254 A1 | 5/2010 | Kornet |
| 2010/0125217 A1 | 5/2010 | Kuo et al. |
| 2010/0144627 A1 | 6/2010 | Vitek et al. |
| 2010/0145146 A1 | 6/2010 | Melder |
| 2010/0177100 A1 | 7/2010 | Carnes et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0234706 A1 | 9/2010 | Gilland |
| 2010/0234718 A1 | 9/2010 | Sampath et al. |
| 2010/0240945 A1 | 9/2010 | Bikko |
| 2010/0241115 A1 | 9/2010 | Benamou et al. |
| 2010/0249540 A1 | 9/2010 | Lisogurski |
| 2010/0261979 A1 | 10/2010 | Kiani |
| 2010/0298651 A1 | 11/2010 | Moon et al. |
| 2010/0298657 A1 | 11/2010 | McCombie et al. |
| 2010/0298659 A1 | 11/2010 | Mccombie et al. |
| 2010/0298661 A1 | 11/2010 | Mccombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2011/0001605 A1 | 1/2011 | Kiani et al. |
| 2011/0015533 A1 | 1/2011 | Cox et al. |
| 2011/0021930 A1 | 1/2011 | Mazzeo et al. |
| 2011/0023130 A1 | 1/2011 | Gudgel et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0046495 A1 | 2/2011 | Osypka |
| 2011/0066051 A1 | 3/2011 | Moon |
| 2011/0077473 A1* | 3/2011 | Lisogurski ......... A61B 5/14551 600/301 |
| 2011/0077487 A1 | 3/2011 | Buxton et al. |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0105956 A1 | 5/2011 | Hirth |

(56) References Cited

U.S. PATENT DOCUMENTS

| | | |
|---|---|---|
| 2011/0118561 A1 | 5/2011 | Tari et al. |
| 2011/0118573 A1 | 5/2011 | Mckenna |
| 2011/0118616 A1 | 5/2011 | Vajdic et al. |
| 2011/0125060 A1 | 5/2011 | Telfort et al. |
| 2011/0152629 A1 | 6/2011 | Eaton et al. |
| 2011/0172498 A1 | 7/2011 | Olsen et al. |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213212 A1 | 9/2011 | Al-Ali |
| 2011/0227739 A1 | 9/2011 | Gilham et al. |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0257544 A1 | 10/2011 | Kaasinen et al. |
| 2011/0257554 A1 | 10/2011 | Banet et al. |
| 2011/0263950 A1 | 10/2011 | Larson |
| 2011/0288383 A1 | 11/2011 | Diab |
| 2011/0295094 A1 | 12/2011 | Doyle et al. |
| 2011/0301444 A1 | 12/2011 | Al-Ali |
| 2011/0307274 A1* | 12/2011 | Thompson ....... G06Q 10/06311 705/3 |
| 2012/0004579 A1 | 1/2012 | Luo et al. |
| 2012/0029300 A1 | 2/2012 | Paquet |
| 2012/0029304 A1 | 2/2012 | Medina et al. |
| 2012/0029879 A1 | 2/2012 | Sing |
| 2012/0041316 A1 | 2/2012 | Al-Ali et al. |
| 2012/0046557 A1 | 2/2012 | Kiani |
| 2012/0059230 A1 | 3/2012 | Teller et al. |
| 2012/0059267 A1 | 3/2012 | Lamego et al. |
| 2012/0071771 A1 | 3/2012 | Behar |
| 2012/0075464 A1 | 3/2012 | Derenne |
| 2012/0088984 A1 | 4/2012 | Al-Ali et al. |
| 2012/0095778 A1 | 4/2012 | Gross et al. |
| 2012/0101353 A1 | 4/2012 | Reggiardo et al. |
| 2012/0116175 A1 | 5/2012 | Al-Ali et al. |
| 2012/0123231 A1 | 5/2012 | O'Reilly |
| 2012/0123799 A1 | 5/2012 | Nolen et al. |
| 2012/0136221 A1 | 5/2012 | Killen et al. |
| 2012/0157806 A1 | 6/2012 | Stelger |
| 2012/0165629 A1 | 6/2012 | Merritt et al. |
| 2012/0179006 A1 | 7/2012 | Jansen et al. |
| 2012/0184120 A1 | 7/2012 | Basta et al. |
| 2012/0197619 A1 | 8/2012 | Namer Yelin et al. |
| 2012/0203078 A1 | 8/2012 | Sze |
| 2012/0209082 A1 | 8/2012 | Al-Ali |
| 2012/0209084 A1 | 8/2012 | Olsen et al. |
| 2012/0221634 A1* | 8/2012 | Treu .................. G06F 19/3418 709/203 |
| 2012/0226117 A1 | 9/2012 | Lamego et al. |
| 2012/0226160 A1 | 9/2012 | Kudoh |
| 2012/0227739 A1 | 9/2012 | Kiani |
| 2012/0239434 A1 | 9/2012 | Breslow et al. |
| 2012/0242501 A1 | 9/2012 | Tran |
| 2012/0265039 A1 | 10/2012 | Kiani |
| 2012/0282583 A1 | 11/2012 | Thaler et al. |
| 2012/0283524 A1 | 11/2012 | Kiani et al. |
| 2012/0284053 A1 | 11/2012 | Rosenfeld |
| 2012/0286955 A1 | 11/2012 | Welch et al. |
| 2012/0294801 A1 | 11/2012 | Scherz et al. |
| 2012/0296178 A1 | 11/2012 | Lamego et al. |
| 2012/0302894 A1 | 11/2012 | Diab et al. |
| 2012/0303476 A1 | 11/2012 | Krzyzanowski et al. |
| 2012/0319816 A1 | 12/2012 | Al-Ali |
| 2012/0330112 A1 | 12/2012 | Lamego et al. |
| 2013/0006131 A1 | 1/2013 | Narayan et al. |
| 2013/0006151 A1 | 1/2013 | Main et al. |
| 2013/0023775 A1 | 1/2013 | Lamego et al. |
| 2013/0035603 A1 | 2/2013 | Jarausch et al. |
| 2013/0041591 A1 | 2/2013 | Lamego |
| 2013/0045685 A1 | 2/2013 | Kiani |
| 2013/0046197 A1 | 2/2013 | Dlugos et al. |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0092805 A1 | 4/2013 | Funk et al. |
| 2013/0096405 A1 | 4/2013 | Garfio |
| 2013/0096936 A1 | 4/2013 | Sampath et al. |
| 2013/0109929 A1 | 5/2013 | Menzel |
| 2013/0109935 A1 | 5/2013 | Al-Ali et al. |
| 2013/0123616 A1 | 5/2013 | Merritt et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0197364 A1 | 8/2013 | Han |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0261494 A1 | 10/2013 | Bloom |
| 2013/0262730 A1 | 10/2013 | Al-Ali et al. |
| 2013/0267793 A1 | 10/2013 | Meador et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0279109 A1 | 10/2013 | Lindblad et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0317393 A1 | 11/2013 | Weiss |
| 2013/0324804 A1 | 12/2013 | McKeown et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0340176 A1 | 12/2013 | Stevens |
| 2013/0345921 A1 | 12/2013 | Al-Ali et al. |
| 2014/0012100 A1 | 1/2014 | Al-Ali et al. |
| 2014/0022081 A1 | 1/2014 | Ribble |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0046674 A1 | 2/2014 | Rosenfeld |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0152673 A1 | 6/2014 | Lynn et al. |
| 2014/0155712 A1 | 6/2014 | Lamego et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |

(56) References Cited

U.S. PATENT DOCUMENTS

| | | |
|---|---|---|
| 2014/0187973 A1 | 7/2014 | Brown et al. |
| 2014/0188516 A1 | 7/2014 | Kamen |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0257057 A1 | 9/2014 | Reis Cunha |
| 2014/0266787 A1 | 9/2014 | Tran |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0343889 A1 | 11/2014 | Ben Shalom |
| 2014/0357966 A1 | 12/2014 | Al-Ali |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0001302 A1 | 1/2015 | Gelay et al. |
| 2015/0005600 A1 | 1/2015 | Blank et al. |
| 2015/0006089 A1 | 1/2015 | Pagels |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0094618 A1 | 4/2015 | Russell |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0246781 A1 | 8/2016 | Cabot |
| 2016/0270717 A1 | 9/2016 | Luna et al. |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |

(56) References Cited

U.S. PATENT DOCUMENTS

| | | |
|---|---|---|
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani |
| 2020/0060629 A1 | 2/2020 | Muhsin et al. |
| 2020/0060869 A1 | 2/2020 | Telfort et al. |

FOREIGN PATENT DOCUMENTS

| | | |
|---|---|---|
| EP | 2335569 | 6/2011 |
| EP | 2766834 | 8/2014 |
| EP | 2811894 | 12/2014 |
| JP | 02-050694 | 2/1990 |
| JP | 09-187428 | 7/1997 |
| JP | 10-336064 | 12/1998 |
| JP | 2000-312668 | 11/2000 |
| JP | 2002-513602 | 5/2002 |
| JP | 2002-165764 | 6/2002 |
| JP | 2002-172096 | 6/2002 |
| JP | 2002-233512 | 8/2002 |
| JP | 2002-535026 | 10/2002 |
| JP | 2002-542493 | 12/2002 |
| JP | 2004-513732 | 5/2004 |
| JP | 2005-038417 | 2/2005 |
| JP | 2008-067931 | 3/2005 |
| JP | 2005-218036 | 8/2005 |

(56) References Cited

FOREIGN PATENT DOCUMENTS

| JP | 2005-295375 | 10/2005 |
|---|---|---|
| JP | 2007-021213 | 2/2007 |
| JP | 2007-095365 | 4/2007 |
| JP | 2007-174051 | 7/2007 |
| JP | 2008-519635 | 6/2008 |
| JP | 2008-541045 | 11/2008 |
| JP | 2009-017959 | 1/2009 |
| JP | 2009-207836 | 9/2009 |
| JP | 2010-503134 | 1/2010 |
| JP | 2010-093543 | 4/2010 |
| JP | 2010-524510 | 7/2010 |
| JP | 2011-519607 | 7/2011 |
| JP | 2011-519684 | 7/2011 |
| JP | 2011-152261 | 8/2011 |
| JP | 2012-519547 | 8/2012 |
| JP | 2014/533997 | 12/2014 |
| WO | WO 98/29790 | 7/1998 |
| WO | WO 99/13766 | 3/1999 |
| WO | WO 99/056613 | 11/1999 |
| WO | WO 00/063713 | 10/2000 |
| WO | WO 2004/056266 | 7/2004 |
| WO | WO 2004/059551 | 7/2004 |
| WO | WO 2006/051461 | 5/2006 |
| WO | WO 2010/054409 | 5/2010 |
| WO | WO 2011/001302 | 1/2011 |
| WO | WO 2011/002904 | 1/2011 |
| WO | WO 2011/021948 | 2/2011 |
| WO | WO 2011/025549 | 3/2011 |
| WO | WO 2011/041017 | 4/2011 |
| WO | WO 2013/056160 | 4/2013 |
| WO | WO 2013/119982 | 8/2013 |
| WO | WO 2015/054665 | 4/2015 |

OTHER PUBLICATIONS

U.S. Appl. No. 14/815,232, Physiological Measurement Communications Adapter, filed Jul. 31, 2015.
U.S. Appl. No. 14/464,560, Modular Patient Monitor, filed Aug. 20, 2014.
U.S. Appl. No. 14/733,781, Modular Patient Monitor, filed Jun. 8, 2015.
U.S. Appl. No. 13/762,270, Wireless Patient Monitoring Device, filed Feb. 7, 2013.
U.S. Appl. No. 14/511,974, Patient Position Detection System, filed Oct. 10, 2014.
U.S. Appl. No. 14/834,169, Wireless Patient Monitoring Device, filed Aug. 24, 2015.
U.S. Appl. No. 29/537,221, Wireless Patient Monitoring Device, filed Aug. 24, 2015.
U.S. Appl. No. 14/512,237, System for Displaying Medical Monitoring Data, filed Oct. 10, 2014.
U.S. Appl. No. 15/214,156, Medical Monitoring Hub, filed Jul. 19, 2016.
U.S. Appl. No. 15/214,186, Medical Monitoring Hub, filed Jul. 19, 2016.
Capuano et at. "Remote Telemetry—New Twists for Old Technology." Nursing Management. vol. 26, No. 7. Jul. 1995.
Elmer-Dewitt, Philip, Apple's iWatch: The killer apps may be in hospitals, not health clubs, Fortune.com, Feb. 3, 2014, http://fortune.com/2014/02/03/apples-iwatch-the-killer-apps-may-be-in-hospitals-not-health-clubs/, in 4 pages.
EP Office Action dated Jun. 15, 2015. EP App. No. 10195398.2.
Extended European Search Report for European Application No. 10195398.2 dated Jul. 5, 2012.
Grundy et al. "Telemedicine in Critical Care: An Experiment in Health Care Delivery." Oct. 1977. pp. 439-444.
Grundy et al. "Telemedicine in Critical Care: Problems in design, implementation and assessment." vol. 10, No. 7. Jul. 1982. pp. 471-475.
JP Office Action dated Aug. 17, 2015 for Application No. 2014-556738.
PCT International Preliminary Report on Patentability for Application No. PCT/US2012/060109, dated Apr. 24, 2014.
PCT International Search Report & Written Opinion, App. No. PCT/US2012/060109, dated Jun. 5, 2013.
PCT International Search Report & Written Opinion, App. No. PCT/US2014/060177, dated Dec. 19, 2014.
PCT International Search Report and Written Opinion, App. No. PCT/US2013/025384, dated Aug. 6, 2013.
Rysavy, "Making the Call with Two-Way Paging", Network Computing, Published Jan. 15, 1997, www.rysavy.com/Articles/twoway.htm.
Wachter, S. Blake; Journal of the American Medical Informatics Association; The Employment of an Iterative Design Process to Develop a Pulmonary Graphical Display; vol. 10, No. 4, Jul./Aug. 2003; pp. 363-372.
U.S. Appl. No. 15/448,989, Arm Mountable Portable Patient Monitor, filed Mar. 3, 2017.
U.S. Appl. No. 15/878,172, Arm Mountable Portable Patient Monitor, filed Jan. 23, 2018.
U.S. Appl. No. 16/157,643, Physiological Measurement Device, filed Oct. 11, 2018.
U.S. Appl. No. 16/198,057, Physiological Measurement Device, filed Nov. 21, 2018.
U.S. Appl. No. 15/814,227, Modular Patient Monitor, filed Nov. 15, 2017.
U.S. Appl. No. 16/182,427, Wireless Patient Monitoring Device, filed Nov. 6, 2018.
U.S. Appl. No. 16/182,457, Wireless Patient Monitoring Device, filed Nov. 6, 2018.
U.S. Appl. No. 15/968,392, Medical Monitoring Hub, filed May 1, 2018.
U.S. Appl. No. 15/919,792, System for Displaying Medical Monitoring Data, filed Mar. 3, 2018.
International Preliminary Report on Patentability & Written Opinion in PCT Application No. PCT/US2013/025384, dated Aug. 21, 2014.
International Preliminary Report on Patentability & Written Opinion in PCT Application No. PCT/US2014/060177, dated Apr. 21, 2016.
U.S. Appl. No. 16/411,689, Physiological Measurement Device, filed May 14, 2019.
U.S. Appl. No. 16/432,240, Modular Patient Monitor, filed Jun. 5, 2019.
U.S. Appl. No. 12/840,209, Wireless Patient Monitoring System, filed Jul. 20, 2010.
U.S. Appl. No. 13/010,653, Wireless Patient Monitoring System, filed Jan. 20, 2011.
U.S. Appl. No. 16/670,051, System for Displaying Medical Monitoring Data, filed Oct. 31, 2019.

* cited by examiner

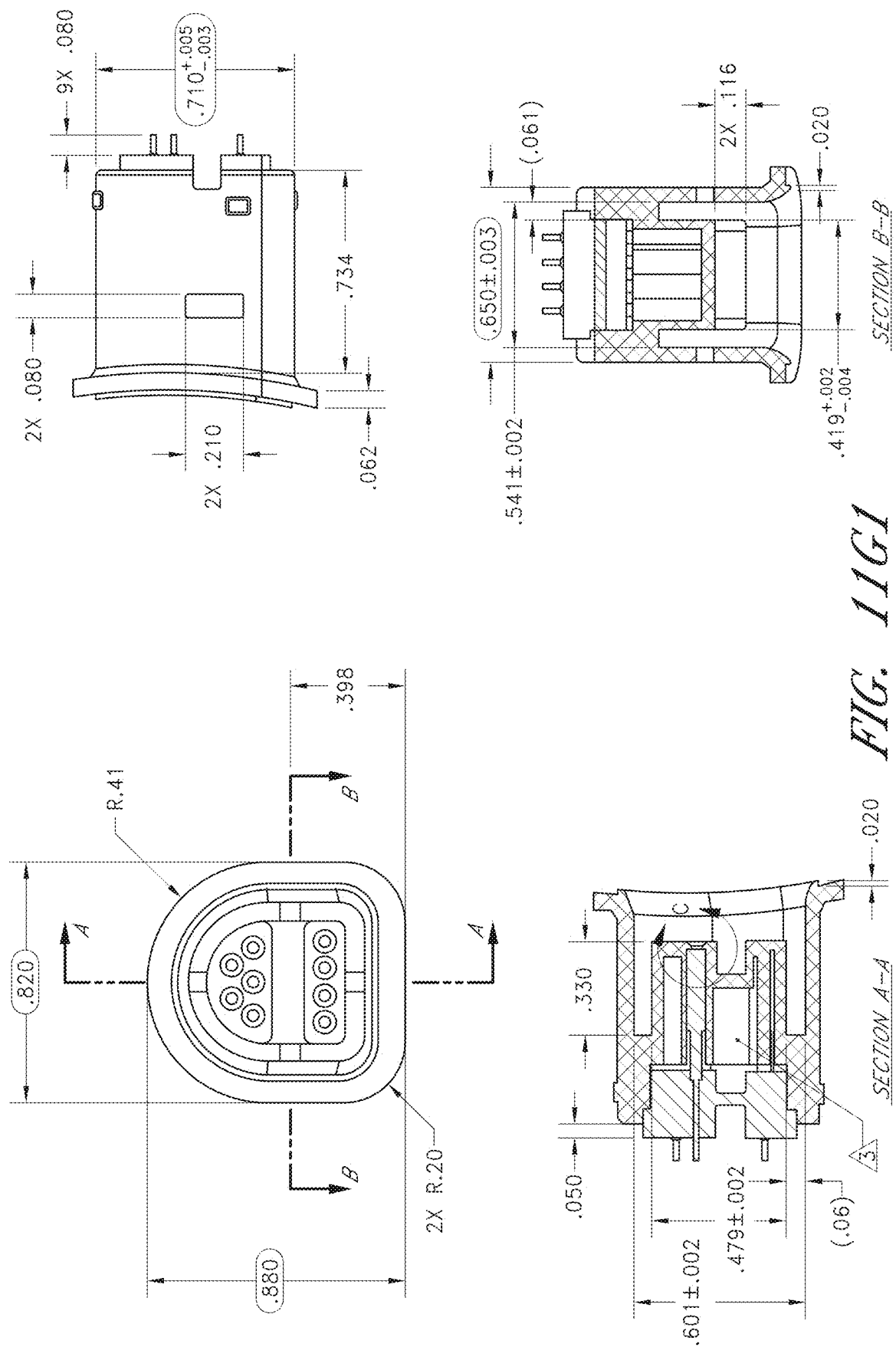
FIG. 11G1

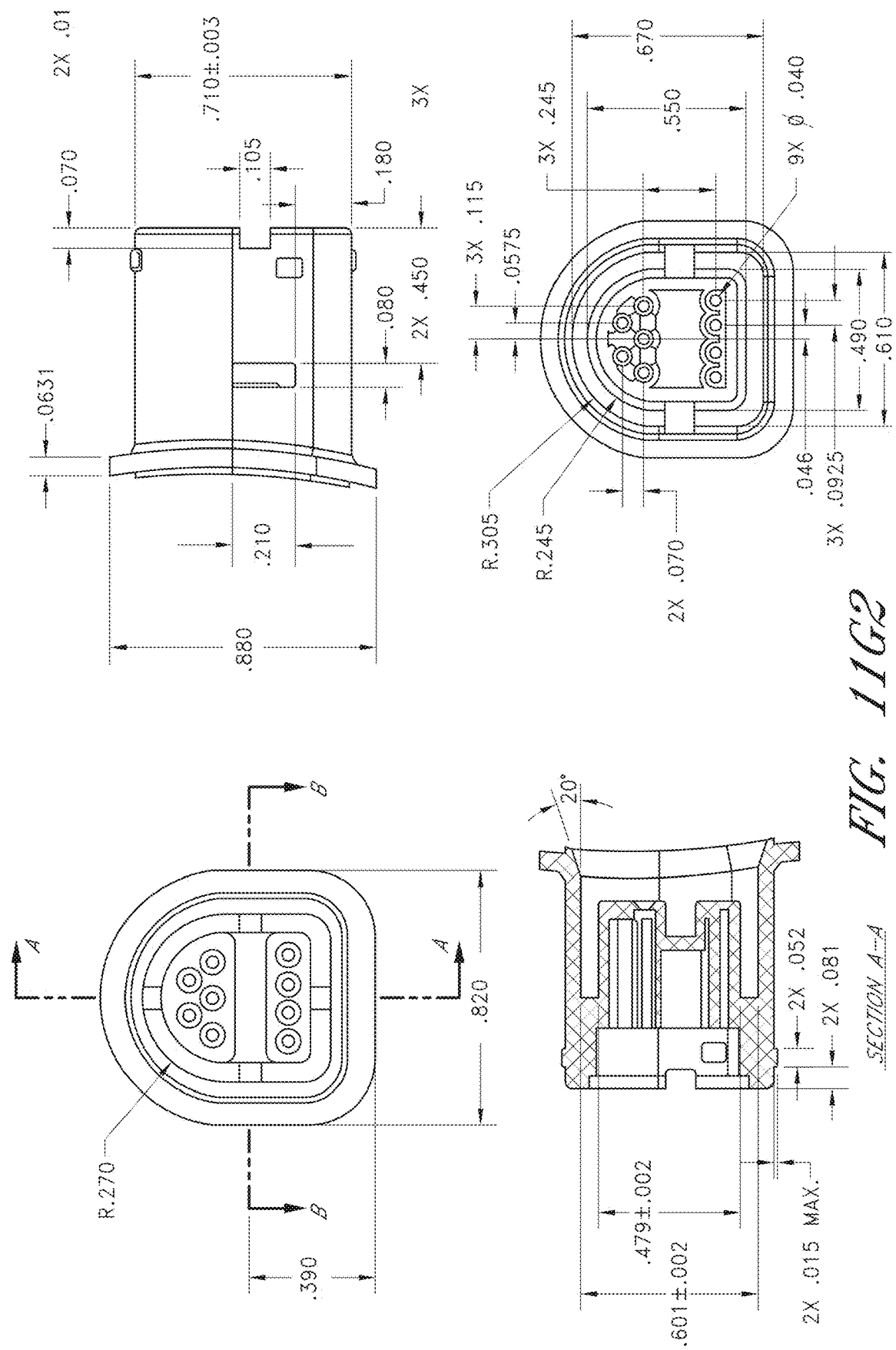
FIG. 11G2

MEDICAL MONITORING HUB

PRIORITY CLAIM AND RELATED APPLICATIONS

This application is a divisional of U.S. patent application Ser. No. 13/651,167, filed Oct. 12, 2012, and titled "Medical Monitoring Hub," which application claims a priority benefit under 35 U.S.C. § 119 to the following U.S. Provisional Patent Applications:

| Ser. No. | Date | Title |
| --- | --- | --- |
| 61/547,017 | Oct. 13, 2011 | Visual Correlation of Physiological Information, |
| 61/547,577 | Oct. 14, 2011 | Visual Correlation of Physiological Information, |
| 61/597,120 | Feb. 9, 2012 | Visual Correlation of Physiological Information, and. |
| 61/703,773 | Sep. 20, 2012 | Medical Monitoring Hub |

Each of the foregoing disclosures is incorporated by reference herein in its entirety.

FIELD OF THE DISCLOSURE

The present disclosure relates generally to patient monitoring devices and specifically to a patient monitor and medical data communication hub.

BACKGROUND OF THE DISCLOSURE

Today's patient monitoring environments are crowded with sophisticated and often electronic medical devices servicing a wide variety of monitoring and treatment endeavors for a given patient. Generally, many if not all of the devices are from differing manufactures, and many may be portable devices. The devices may not communicate with one another and each may include its own control, display, alarms, configurations and the like. Complicating matters, caregivers often desire to associate all types of measurement and use data from these devices to a specific patient. Thus, patient information entry often occurs at each device. Sometimes, the disparity in devices leads to a need to simply print and store paper from each device in a patient's file for caregiver review.

The result of such device disparity is often a caregiver environment scattered with multiple displays and alarms leading to a potentially chaotic experience. Such chaos can be detrimental to the patient in many situations including surgical environments where caregiver distraction is unwanted, and including recovery or monitoring environments where patient distraction or disturbance may be unwanted.

Various manufacturers produce multi-monitor devices or devices that modularly expand to increase the variety of monitoring or treatment endeavors a particular system can accomplish. However, as medical device technology expands, such multi-monitor devices begin to be obsolete the moment they are installed.

SUMMARY OF THE INVENTION

Based on at least the foregoing, a solution is needed that coordinates the various medical devices treating or monitoring a patient. Embodiments of such a solution should provide patient identification seamlessly across the device space and embodiments of such a solution should expand for future technologies without necessarily requiring repeated software upgrades. In addition, embodiments of such a solution may include patient electrical isolation where desired.

Therefore, the present disclosure relates to a patient monitoring hub that is the center of patient monitoring and treatment activities for a given patient. Embodiments of the patient monitoring hub interface with legacy devices without necessitating legacy reprogramming, provide flexibility for interfacing with future devices without necessitating software upgrades, and offer optional patient electrical isolation. In an embodiment, the hub includes a large display dynamically providing information to a caregiver about a wide variety of measurement or otherwise determined parameters. Additionally, in an embodiment, the hub includes a docking station for a portable patient monitor. The portable patient monitor may communicate with the hub through the docking station or through various wireless paradigms known to an artisan from the disclosure herein, including WiFi, Bluetooth, Zigbee, or the like.

In still other embodiments, the portable patient monitor modifies its screen when docked. The undocked display indicia is in part or in whole transferred to a large dynamic display of the hub and the docked display presents one or more anatomical graphics of monitored body parts. For example, the display may present a heart, lungs, a brain, kidneys, intestines, a stomach, other organs, digits, gastrointestinal systems or other body parts when it is docked. In an embodiment, the anatomical graphics may advantageously be animated. In an embodiment, the animation may generally follow the behavior of measured parameters, such as, for example, the lungs may inflate in approximate correlation to the measured respiration rate and/or the determined inspiration portion of a respiration cycle, and likewise deflate according to the expiration portion of the same. The heart may beat according to the pulse rate, may beat generally along understood actual heart contraction patterns, and the like. Moreover, in an embodiment, when the measured parameters indicate a need to alert a caregiver, a changing severity in color may be associated with one or more displayed graphics, such as the heart, lungs, brain, or the like. In still other embodiments, the body portions may include animations on where, when or how to attach measurement devices to measurement sites on the patient. For example, the monitor may provide animated directions for CCHD screening procedures or glucose strip reading protocols, the application of a forehead sensor, a finger or toe sensor, one or more electrodes, an acoustic sensor, and ear sensor, a cannula sensor or the like.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

FIG. 1A illustrates the hub with an exemplary docked portable patient monitor, FIG. 1B illustrates the hub with a set of medical ports and a noninvasive blood pressure input, and FIG. 1C illustrates the hub with various exemplary temperature sensors attached thereto, all according to various embodiments of the disclosure.

FIG. 5 illustrates an exemplary alternative docking station.

FIGS. 11A-11K illustrate various views of exemplary male and mating female universal medical connectors, according to embodiments of the disclosure.

Figure 1A:
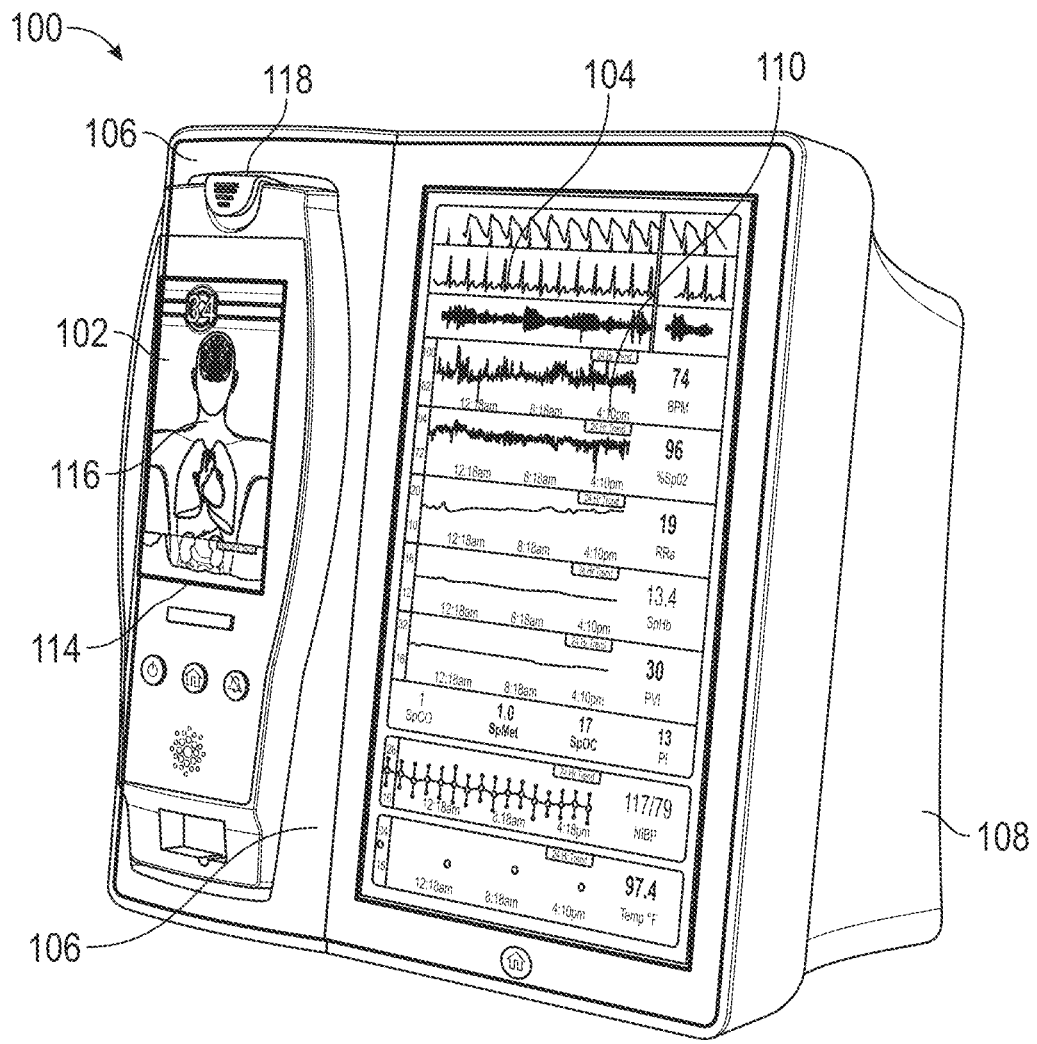
FIGS. 1A-1C illustrate perspective views of an exemplary medical monitoring hub according to an embodiment of the disclosure. For example.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION OF THE PREFERRED EMBODIMENT

The present disclosure relates to a medical monitoring hub configured to be the center of monitoring activity for a given patient. In an embodiment, the hub comprises a large easily readable display, such as an about ten (10) inch display dominating the majority of real estate on a front face of the hub. The display could be much larger or much smaller depending upon design constraints. However, for portability and current design goals, the preferred display is roughly sized proportional to the vertical footprint of one of the dockable portable patient monitors. Other considerations are recognizable from the disclosure herein by those in the art.

The display provides measurement data for a wide variety of monitored parameters for the patient under observation in numerical or graphic form, and in various embodiments, is automatically configured based on the type of data and information being received at the hub. In an embodiment, the hub is moveable, portable, and mountable so that it can be positioned to convenient areas within a caregiver environment. For example, the hub is collected within a singular housing.

In an embodiment, the hub may advantageously receive data from a portable patient monitor while docked or undocked from the hub. Typical portable patient monitors, such as oximeters or co-oximeters can provide measurement data for a large number of physiological parameters derived from signals output from optical and/or acoustic sensors, electrodes, or the like. The physiological parameters include, but not limited to oxygen saturation, carboxy hemoglobin, methemoglobin, total hemoglobin, glucose, pH, bilirubin, fractional saturation, pulse rate, respiration rate, components of a respiration cycle, indications of perfusion including perfusion index, signal quality and/or confidences, plethysmograph data, indications of wellness or wellness indexes or other combinations of measurement data, audio information responsive to respiration, ailment identification or diagnosis, blood pressure, patient and/or measurement site temperature, depth of sedation, organ or brain oxygenation, hydration, measurements responsive to metabolism, combinations of the same or the like, to name a few. In other embodiments, the hub may output data sufficient to accomplish closed-loop drug administration in combination with infusion pumps or the like.

In an embodiment, the hub communicates with other devices in a monitoring environment that are interacting with the patient in a number of ways. For example, the hub advantageously receives serial data from other devices without necessitating their reprogramming or that of the hub. Such other devices include pumps, ventilators, all manner of monitors monitoring any combination of the foregoing parameters, ECG/EEG/EKG devices, electronic patient beds, and the like. Moreover, the hub advantageously receives channel data from other medical devices without necessitating their reprogramming or that of the hub. When a device communicates through channel data, the hub may advantageously alter the large display to include measurement information from that device. Additionally, the hub accesses nurse call systems to ensure that nurse call situations from the device are passed to the appropriate nurse call system.

The hub also communicates with hospital systems to advantageously associate incoming patient measurement and treatment data with the patient being monitored. For example, the hub may communicate wirelessly or otherwise to a multi-patient monitoring system, such as a server or collection of servers, which in turn many communicate with a caregiver's data management systems, such as, for example, an Admit, Discharge, Transfer ("ADT") system and/or an Electronic Medical Records ("EMR") system. The hub advantageously associates the data flowing through it with the patient being monitored thereby providing the electronic measurement and treatment information to be passed to the caregiver's data management systems without the caregiver associating each device in the environment with the patient.

In an embodiment, the hub advantageously includes a reconfigurable and removable docking station. The docking station may dock additional layered docking stations to adapt to different patient monitoring devices. Additionally, the docking station itself is modularized so that it may be removed if the primary dockable portable patient monitor changes its form factor. Thus, the hub is flexible in how its docking station is configured.

In an embodiment, the hub includes a large memory for storing some or all of the data it receives, processes, and/or associates with the patient, and/or communications it has with other devices and systems. Some or all of the memory may advantageously comprise removable SD memory.

The hub communicates with other devices through at least (1) the docking station to acquire data from a portable monitor, (2) innovative universal medical connectors to acquire channel data, (3) serial data connectors, such as RJ ports to acquire output data, (4) Ethernet, USB, and nurse call ports, (5) Wireless devices to acquire data from a portable monitor, (6) other wired or wireless communication mechanisms known to an artisan. The universal medical connectors advantageously provide optional electrically isolated power and communications, are designed to be smaller in cross section than isolation requirements. The connectors and the hub communicate to advantageously translate or configure data from other devices to be usable and displayable for the hub. In an embodiment, a software developers kit ("SDK") is provided to a device manufacturer to establish or define the behavior and meaning of the data output from their device. When the output is defined, the definition is programmed into a memory residing in the cable side of the universal medical connector and supplied as an original equipment manufacture ("OEM") to the device provider. When the cable is connected between the device and the hub, the hub understands the data and can use it for display and processing purposes without necessitating software upgrades to the device or the hub. In an embodiment, the hub can negotiate the schema and even add additional compression and/or encryption. Through the use of the universal medical connectors, the hub organizes the measurement and treatment data into a single display and alarm system effectively and efficiently bringing order to the monitoring environment.

As the hub receives and tracks data from other devices according to a channel paradigm, the hub may advantageously provide processing to create virtual channels of patient measurement or treatment data. In an embodiment, a virtual channel may comprise a non-measured parameter that is, for example, the result of processing data from various measured or other parameters. An example of such a parameter includes a wellness indicator derived from various measured parameters that give an overall indication of the wellbeing of the monitored patient. An example of a wellness parameter is disclosed in U.S. patent application Ser. Nos. 13/269,296, 13/371,767 and 12/904,925, by the assignee of the present disclosure and incorporated by reference herein. By organizing data into channels and virtual channels, the hub may advantageously time-wise synchronize incoming data and virtual channel data.

The hub also receives serial data through serial communication ports, such as RJ connectors. The serial data is associated with the monitored patient and passed on to the multi-patient server systems and/or caregiver backend systems discussed above. Through receiving the serial data, the caregiver advantageously associates devices in the caregiver environment, often from varied manufactures, with a particular patient, avoiding a need to have each individual device associated with the patient and possible communicating with hospital systems. Such association is vital as it reduces caregiver time spent entering biographic and demographic information into each device about the patient. Moreover, in an embodiment, through the SDK the device manufacturer may advantageously provide information associated with any measurement delay of their device, thereby further allowing the hub to advantageously time-wise synchronize serial incoming data and other data associated with the patient.

In an embodiment, when a portable patient monitor is docked, and it includes its own display, the hub effectively increases its display real estate. For example, in an embodiment, the portable patient monitor may simply continue to display its measurement and/or treatment data, which may be now duplicated on the hub display, or the docked display may alter its display to provide additional information. In an embodiment, the docked display, when docked, presents anatomical graphical data of, for example, the heart, lungs, organs, the brain, or other body parts being measured and/or treated. The graphical data may advantageously animate similar to and in concert with the measurement data. For example, lungs may inflate in approximate correlation to the measured respiration rate and/or the determined inspiration/expiration portions of a respiration cycle, the heart may beat according to the pulse rate, may beat generally along understood actual heart contraction patterns, the brain may change color or activity based on varying depths of sedation, or the like. In an embodiment, when the measured parameters indicate a need to alert a caregiver, a changing severity in color may be associated with one or more displayed graphics, such as the heart, lungs, brain, organs, circulatory system or portions thereof, respiratory system or portions thereof, other body parts or the like. In still other embodiments, the body portions may include animations on where, when or how to attach measurement devices.

The hub may also advantageously overlap parameter displays to provide additional visual information to the caregiver. Such overlapping may be user definable and configurable. The display may also incorporate analog-appearing icons or graphical indicia.

In the interest of clarity, not all features of an actual implementation are described in this specification. An artisan will of course be appreciate that in the development of any such actual implementation (as in any development project), numerous implementation-specific decisions must be made to achieve a developers' specific goals and subgoals, such as compliance with system- and business-related constraints, which will vary from one implementation to another. Moreover, it will be appreciated that such a development effort might be complex and time-consuming, but would nevertheless be a routine undertaking of device engineering for those of ordinary skill having the benefit of this disclosure.

To facilitate a complete understanding of the disclosure, the remainder of the detailed description describes the disclosure with reference to the drawings, wherein like reference numbers are referenced with like numerals throughout.

FIG. 1A illustrates a perspective view of an exemplary medical monitoring hub 100 with an exemplary docked portable patient monitor 102 according to an embodiment of the disclosure. The hub 100 includes a display 104, and a docking station 106, which in an embodiment is configured to mechanically and electrically mate with the portable patient monitor 102, each housed in a movable, mountable and portable housing 108. The housing 108 includes a generally upright inclined shape configured to rest on a horizontal flat surface, although the housing 108 can be affixed in a wide variety of positions and mountings and comprise a wide variety of shapes and sizes.

In an embodiment, the display 104 may present a wide variety of measurement and/or treatment data in numerical, graphical, waveform, or other display indicia 110. In an embodiment, the display 104 occupies much of a front face of the housing 108, although an artisan will appreciate the display 104 may comprise a tablet or tabletop horizontal configuration, a laptop-like configuration or the like. Other embodiments may include communicating display information and data to a table computer, smartphone, television, or any display system recognizable to an artisan. The upright inclined configuration of FIG. 1A presents display information to a caregiver in an easily viewable manner.

Figure 1B:
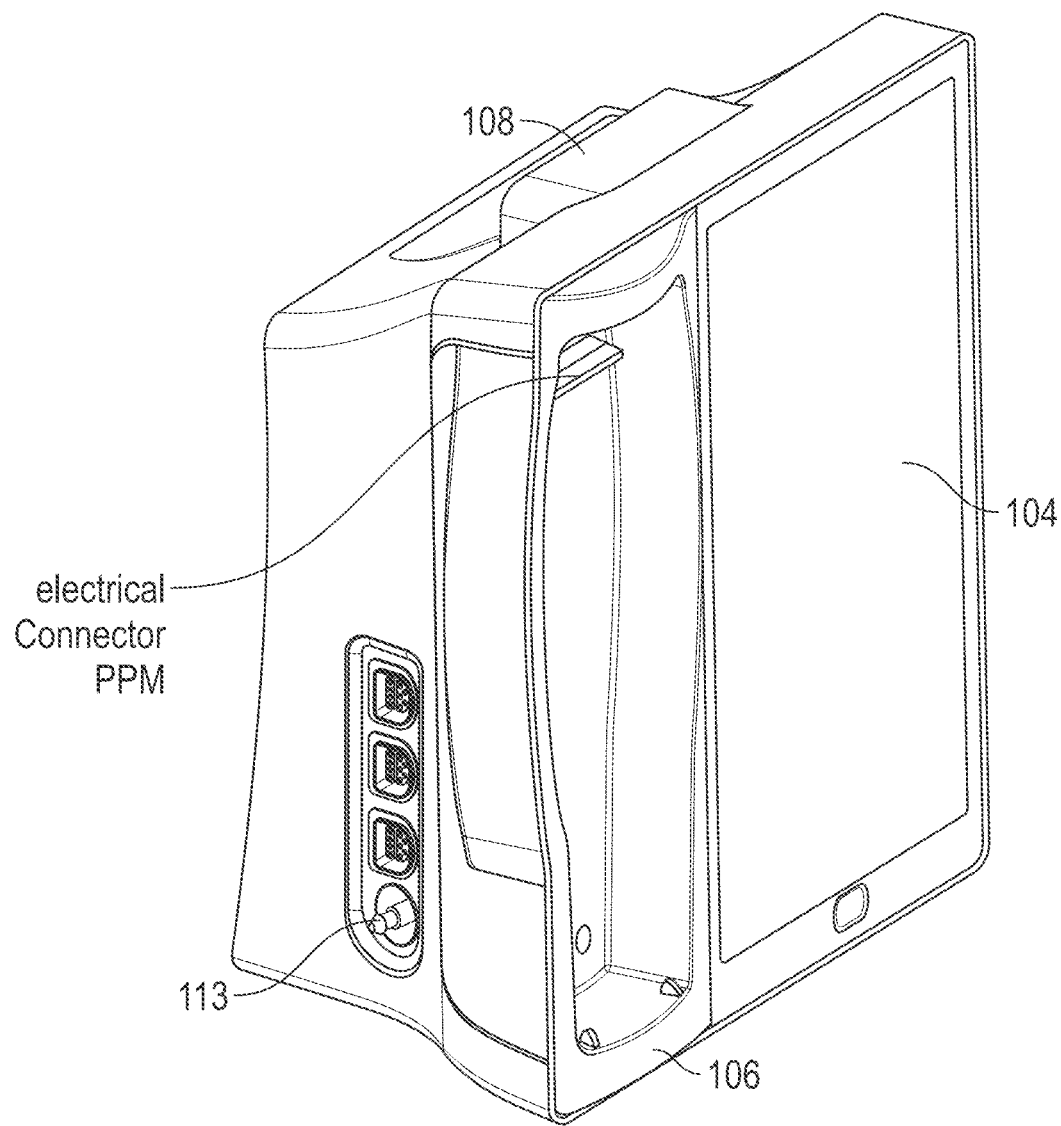

FIG. 1B shows a perspective side view of an embodiment of the hub 100 including the housing 108, the display 104, and the docking station 106 without a portable monitor docked. Also shown is a connector for noninvasive blood pressure.

Figure 1C:
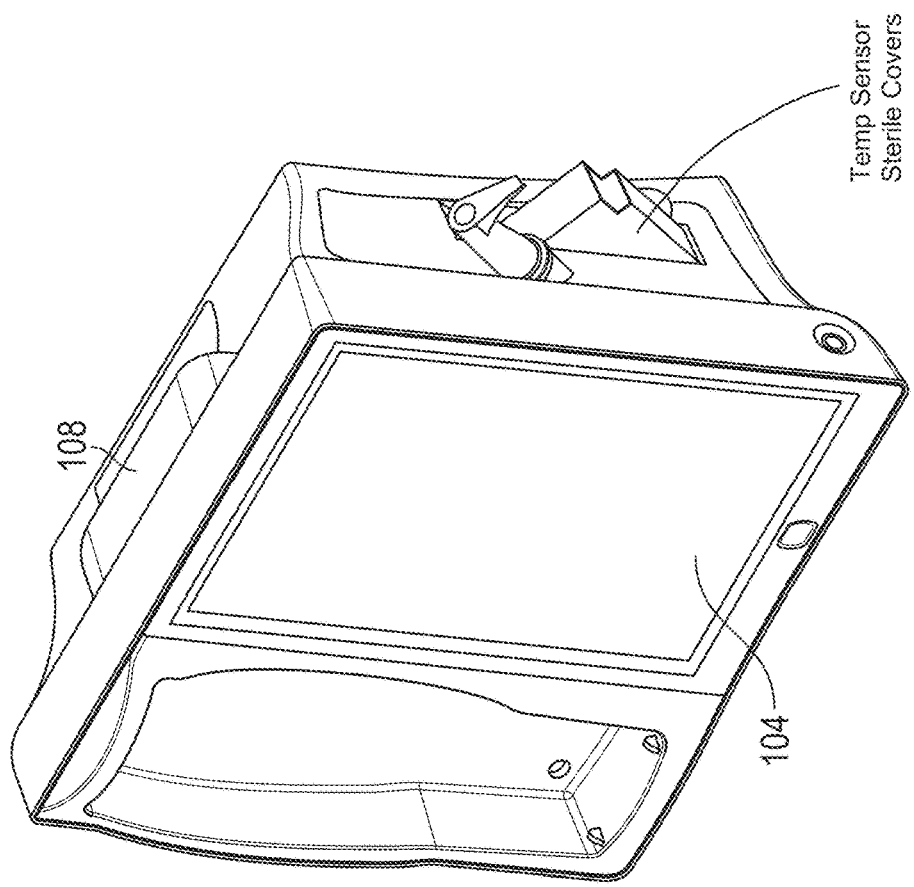
Figure 1C:
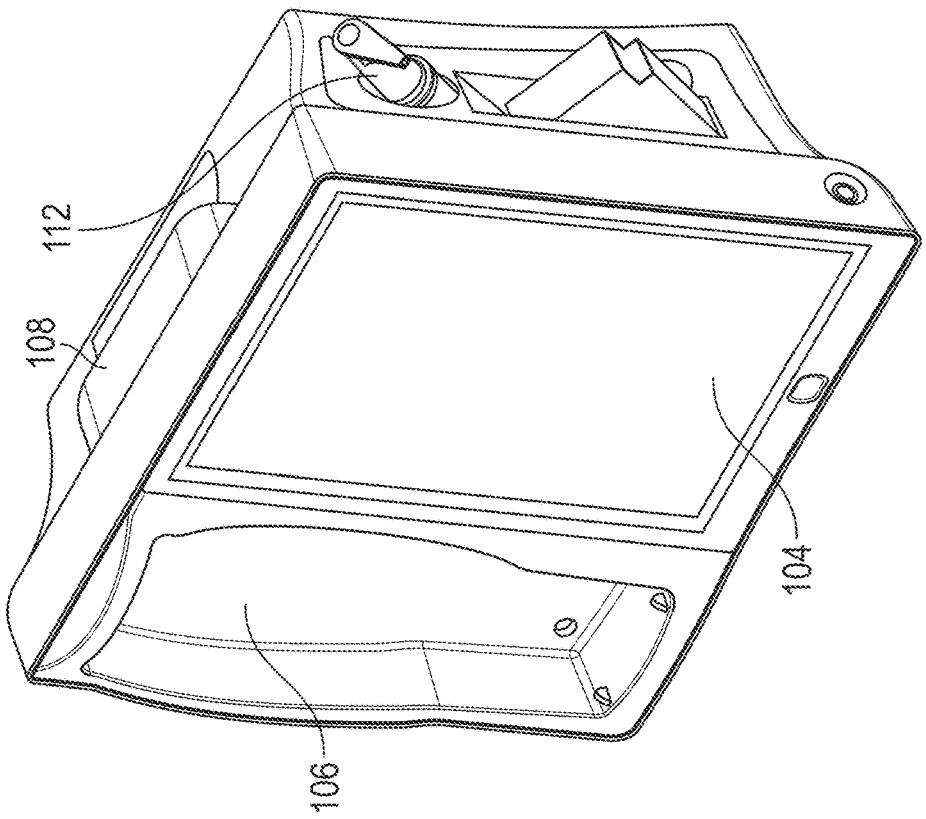

In an embodiment, the housing 108 may also include pockets or indentations to hold additional medical devices, such as, for example, a blood pressure monitor or temperature sensor 112, such as that shown in FIG. 1C.

The portable patient monitor 102 of FIG. 1A may advantageously comprise an oximeter, co-oximeter, respiratory monitor, depth of sedation monitor, noninvasive blood pressure monitor, vital signs monitor or the like, such as those commercially available from Masimo Corporation of Irvine, Calif., and/or disclosed in U.S. Pat. Pub. Nos. 2002/0140675, 2010/0274099, 2011/0213273, 2012/0226117, 2010/0030040; U.S. Pat. App. Ser. Nos. 61/242,792, 61/387,457, 61/645,570, 13/554,908 and U.S. Pat. Nos. 6,157,850, 6,334,065, and the like. The monitor 102 may communicate with a variety of noninvasive and/or minimally invasive devices such as optical sensors with light emission and detection circuitry, acoustic sensors, devices that measure blood parameters from a finger prick, cuffs, ventilators, and the like. The monitor 102 may include its own display 114 presenting its own display indicia 116, discussed below with reference to FIGS. 19A-19J. The display indicia may advantageously change based on a docking state of the monitor 102. When undocked, the display indicia may include parameter information and may alter orientation based on, for example, a gravity sensor or accelerometer.

In an embodiment, the docking station 106 of the hub 100 includes a mechanical latch 118, or mechanically releasable catch to ensure that movement of the hub 100 doesn't mechanically detach the monitor 102 in a manner that could damage the same.

Although disclosed with reference to particular portable patient monitors 102, an artisan will recognize from the disclosure herein a large number and wide variety of medical devices that may advantageously dock with the hub 100. Moreover, the docking station 106 may advantageously electrically and not mechanically connect with the monitor 102, and/or wirelessly communicate with the same.

Figure 2:
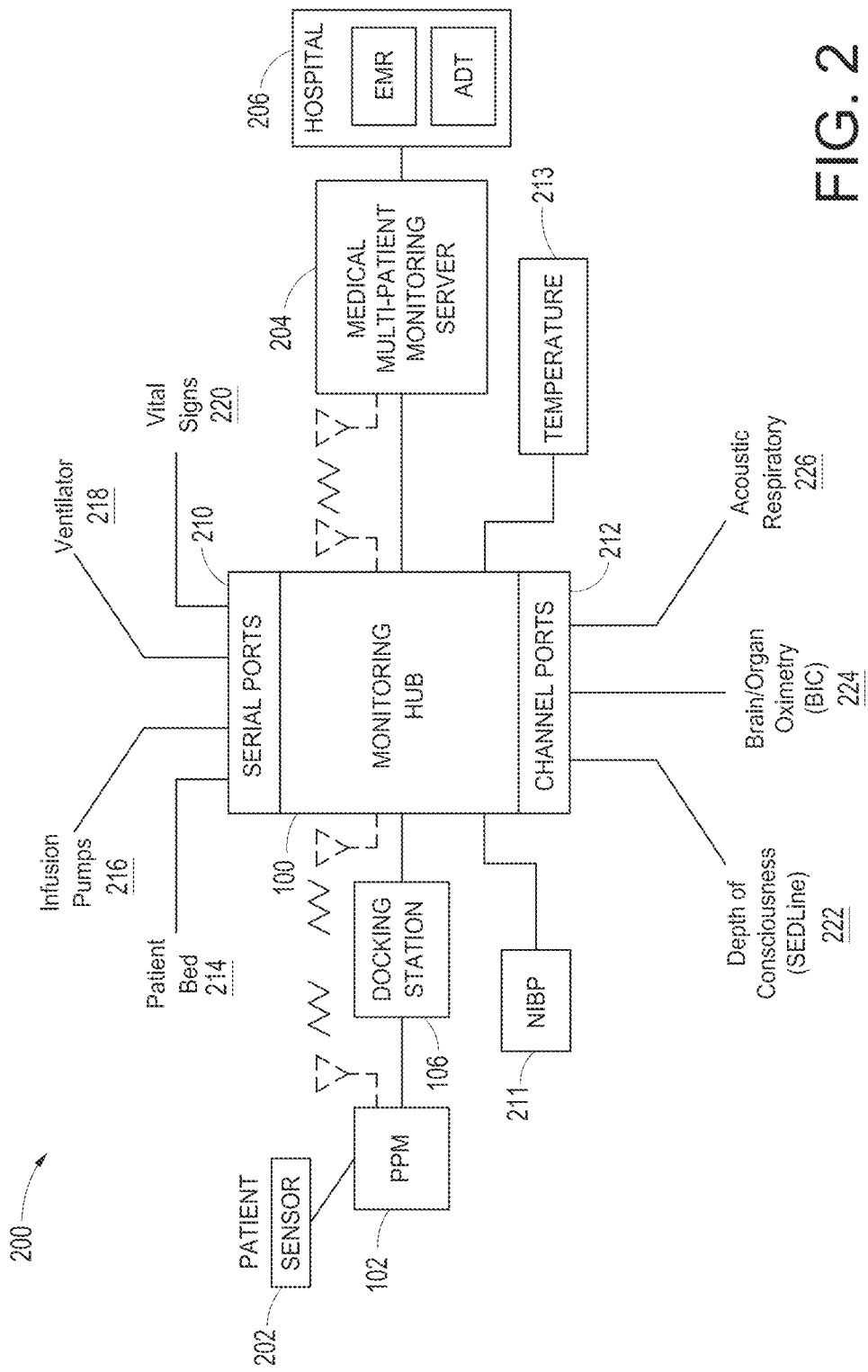
FIG. 2 illustrates a simplified block diagram of an exemplary monitoring environment including the hub of FIG. 1, according to an embodiment of the disclosure.

FIG. 2 illustrates a simplified block diagram of an exemplary monitoring environment 200 including the hub 100 of FIG. 1, according to an embodiment of the disclosure. As shown in FIG. 2, the environment may include the portable patient monitor 102 communicating with one or more patient sensors 202, such as, for example, oximetry optical sensors, acoustic sensors, blood pressure sensors, respiration sensors or the like. In an embodiment, additional sensors, such as, for example, a NIBP sensor or system 211 and a temperature sensor or sensor system 213 may communicate directly with the hub 100. The sensors 202, 211 and 213 when in use are typically in proximity to the patient being monitored if not actually attached to the patient at a measurement site.

As disclosed, the portable patient monitor 102 communicates with the hub 100, in an embodiment, through the docking station 106 when docked and, in an embodiment, wirelessly when undocked, however, such undocked communication is not required. The hub 100 communicates with one or more multi-patient monitoring servers 204 or server systems, such as, for example, those disclosed with in U.S. Pat. Pub. Nos. 2011/0105854, 2011/0169644, and 2007/0180140. In general, the server 204 communicates with caregiver backend systems 206 such as EMR and/or ADT systems. The server 204 may advantageously obtain through push, pull or combination technologies patient information entered at patient admission, such as demographic information, billing information, and the like. The hub 100 accesses this information to seamlessly associate the monitored patient with the caregiver backend systems 206. Communication between the server 204 and the monitoring hub 100 may be any recognizable to an artisan from the disclosure herein, including wireless, wired, over mobile or other computing networks, or the like.

FIG. 2 also shows the hub 100 communicating through its serial data ports 210 and channel data ports 212. As disclosed in the forgoing, the serial data ports 210 may provide data from a wide variety of patient medical devices, including electronic patient bed systems 214, infusion pump systems 216 including closed loop control systems, ventilator systems 218, blood pressure or other vital sign measurement systems 220, or the like. Similarly, the channel data ports 212 may provide data from a wide variety of patient medical devices, including any of the foregoing, and other medical devices. For example, the channel data ports 212 may receive data from depth of consciousness monitors 222, such as those commercially available from SEDLine, brain or other organ oximeter devices 224, noninvasive blood pressure or acoustic devices 226, or the like. In an embodiment, channel device may include board-in-cable ("BIC") solutions where the processing algorithms and the signal processing devices that accomplish those algorithms are mounted to a board housed in a cable or cable connector, which in some embodiments has no additional display technologies. The BIC solution outputs its measured parameter data to the channel port 212 to be displayed on the display 104 of hub 100. In an embodiment, the hub 100 may advantageously be entirely or partially formed as a BIC solution that communicates with other systems, such as, for example, tablets, smartphones, or other computing systems.

Although disclosed with reference to a single docking station 106, the environment 200 may include stacked docking stations where a subsequent docking station mechanically and electrically docks to a first docking station to change the form factor for a different portable patent monitor as discussed with reference to FIG. 5. Such stacking may include more than 2 docking stations, may reduce or increase the form fact for mechanical compliance with mating mechanical structures on a portable device.

Figure 3:
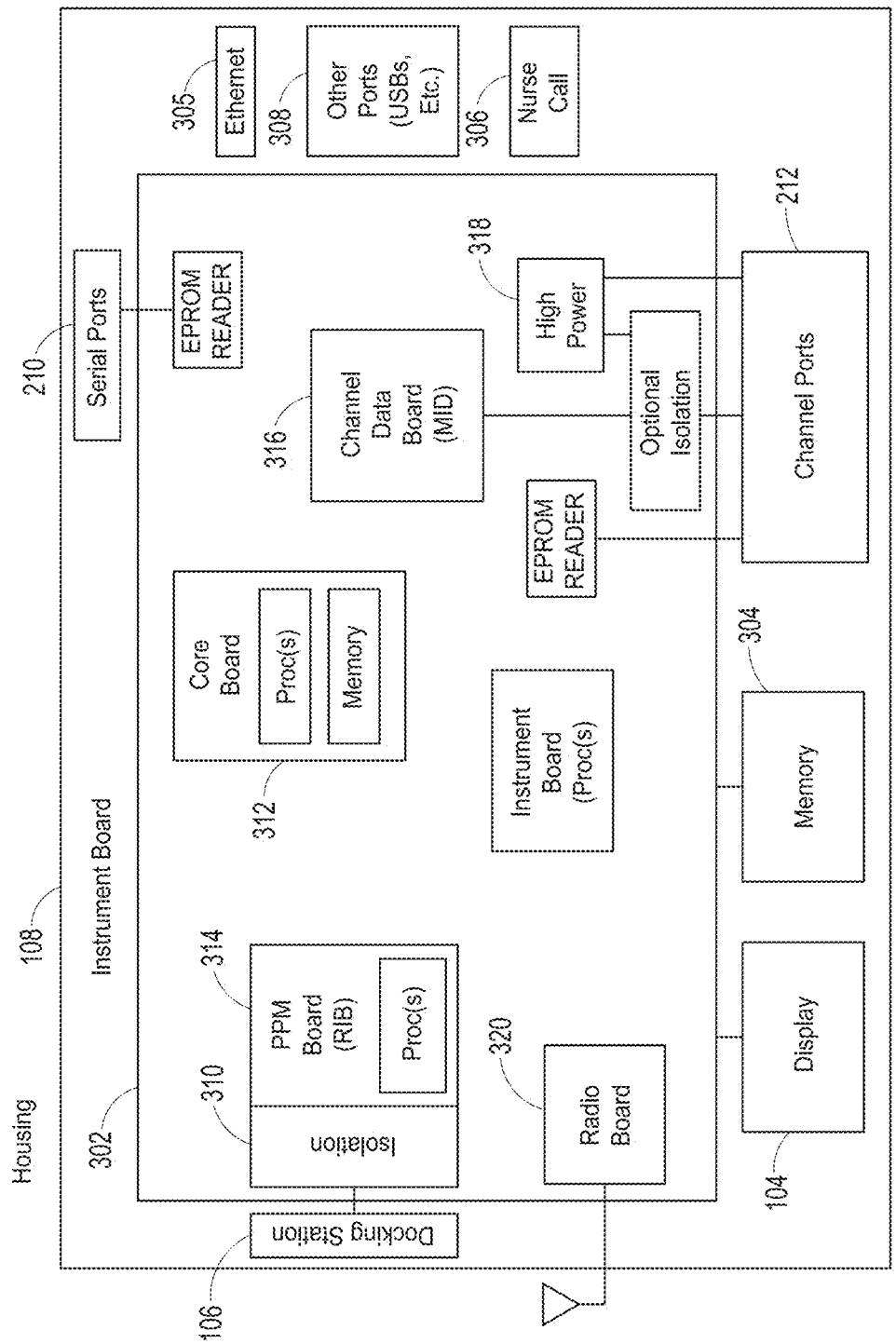
FIG. 3 illustrates a simplified exemplary hardware block diagram of the hub of FIG. 1, according to an embodiment of the disclosure.

FIG. 3 illustrates a simplified exemplary hardware block diagram of the hub 100 of FIG. 1, according to an embodiment of the disclosure. As shown in FIG. 3, the housing 108 of the hub 100 positions and/or encompasses an instrument board 302, the display 104, memory 304, and the various communication connections, including the serial ports 210, the channel ports 212, Ethernet ports 305, nurse call port 306, other communication ports 308 including standard USB or the like, and the docking station interface 310. The instrument board 302 comprises one or more substrates including communication interconnects, wiring, ports and the like to enable the communications and functions described herein, including inter-board communications. A core board 312 includes the main parameter, signal, and other processor(s) and memory, a portable monitor board ("RIB") 314 includes patient electrical isolation for the monitor 102 and one or more processors, a channel board ("MID") 316 controls the communication with the channel ports 212 including optional patient electrical isolation and power supply 318, and a radio board 320 includes components configured for wireless communications. Additionally, the instrument board 302 may advantageously include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

An artisan will recognize from the disclosure herein that the instrument board 302 may comprise a large number of electronic components organized in a large number of ways. Using different boards such as those disclosed above advantageously provides organization and compartmentalization to the complex system.

Figure 4:
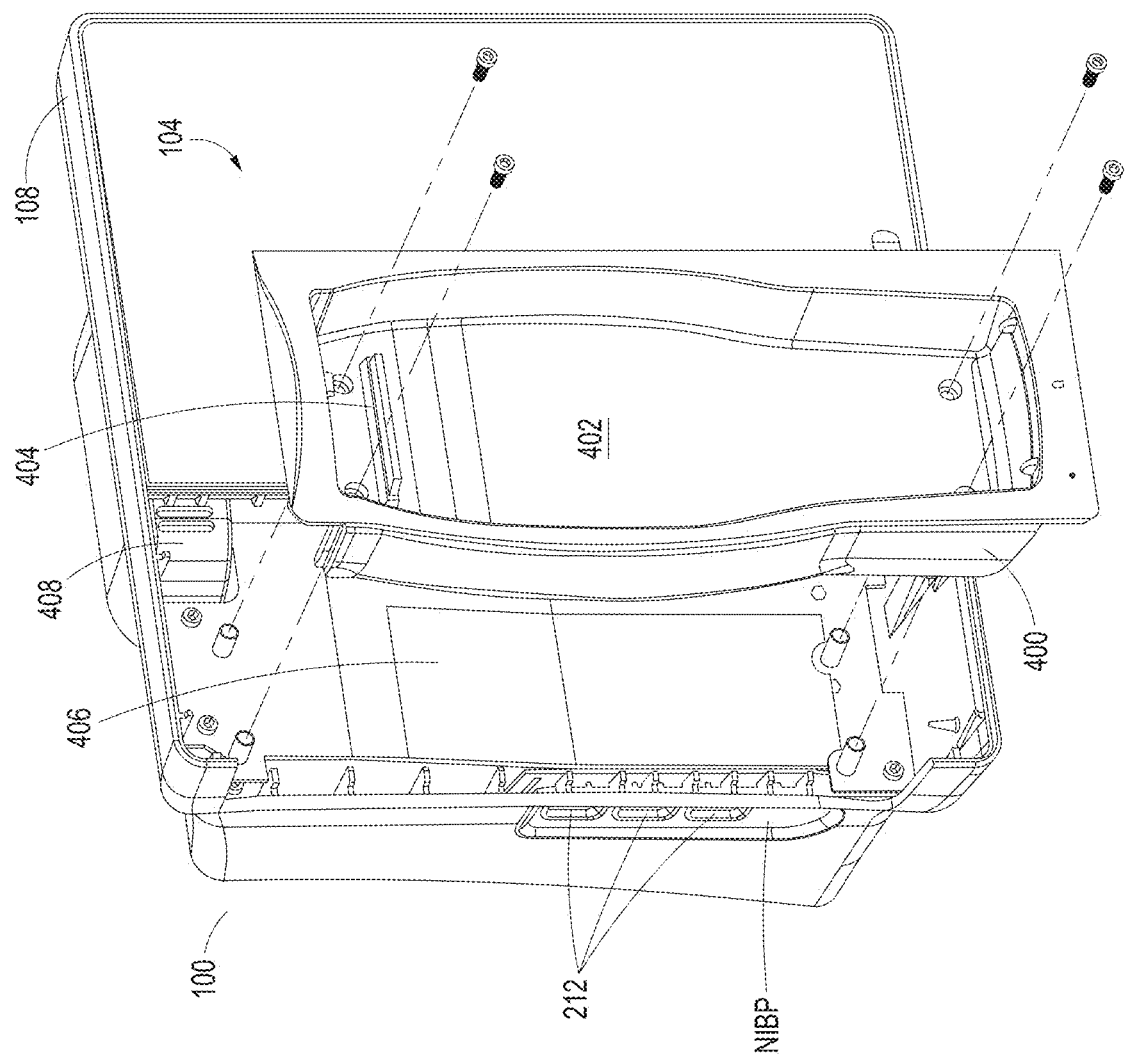
FIG. 4 illustrates a perspective view of an exemplary removable docking station of the hub of FIG. 1, according to an embodiment of the disclosure.

FIG. 4 illustrates a perspective view of an exemplary removable docking station 400 of the hub 100 of FIG. 1, according to an embodiment of the disclosure. As shown in FIG. 4, the docking station 400 provides a mechanical mating to portable patient monitor 102 to provide secure mechanical support when the monitor 102 is docked. The docking station 400 includes a cavity 402 shaped similar to the periphery of a housing of the portable monitor 102. The station 400 also includes one or more electrical connectors 404 providing communication to the hub 100. Although shown as mounted with bolts, the docking station 400 may snap fit, may use movable tabs or catches, may magnetically attach, or may employ a wide variety or combination of attachment mechanisms know to an artisan from the disclosure herein. In an embodiment, the attachment of the docking station 400 should be sufficiently secure that when docked, the monitor 102 and docking station cannot be accidentally detached in a manner that could damage the instruments, such as, for example, if the hub 100 was accidently bumped or the like, the monitor 102 and docking station 400 should remain intact.

The housing 108 of the hub 100 also includes cavity 406 housing the docking station 400. To the extent a change to the form factor for the portable patient monitor 102 occurs, the docking station 400 is advantageously removable and replaceable. Similar to the docking station 400, the hub 100 includes within the cavity 406 of the housing 108 electrical connectors 408 providing electrical communication to the docking station 400. In an embodiment, the docking station 400 includes its own microcontroller and processing capabilities, such as those disclosed in U.S. Pat. Pub. No. 2002/0140675. In other embodiments, the docking station 400 passes communications through to the electrical connector 408.

FIG. 4 also shows the housing 108 including openings for channel ports 212 as universal medical connectors discussed in detail below.

Figure 5:
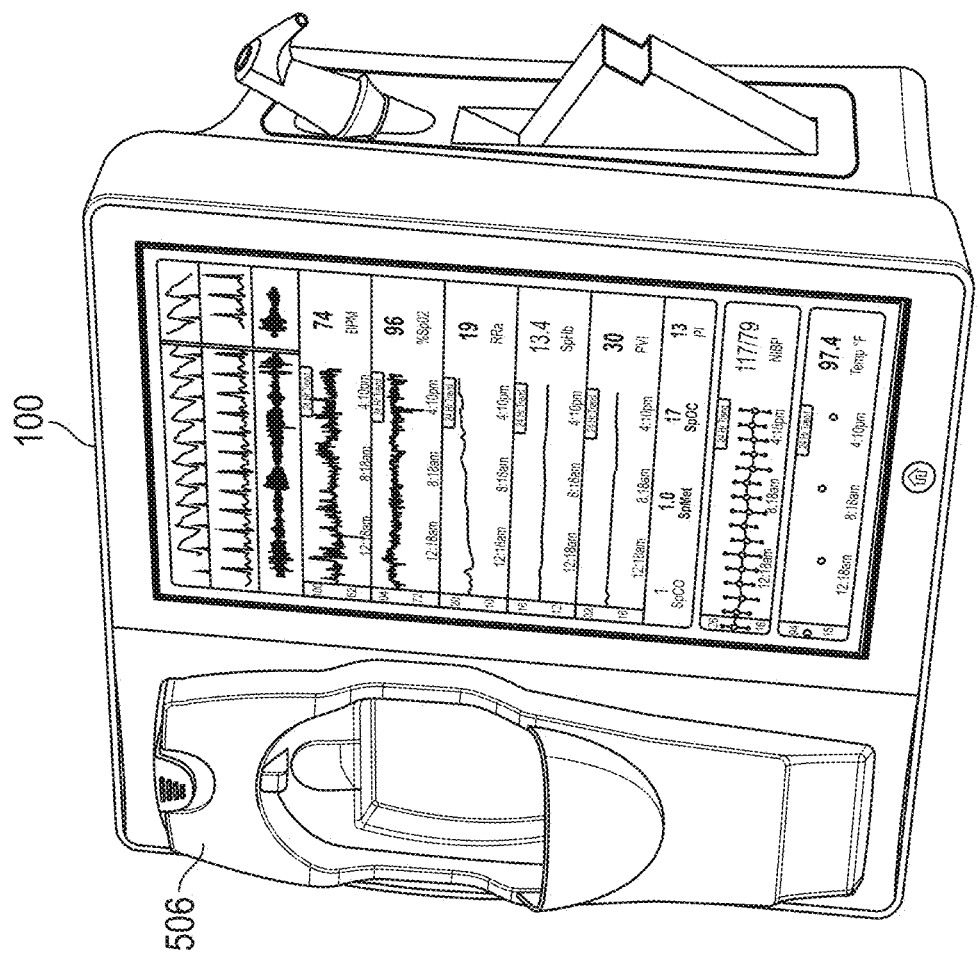
FIG. 5 illustrates a perspective view of exemplary portable patient monitors undocked from the hub of FIG. 1, according to an embodiment of the disclosure. Moreover.
Figure 5:
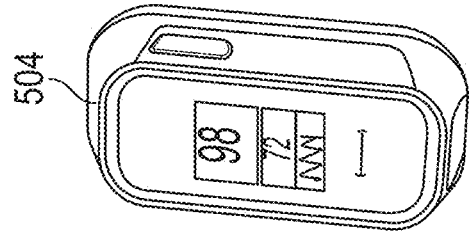
Figure 5:
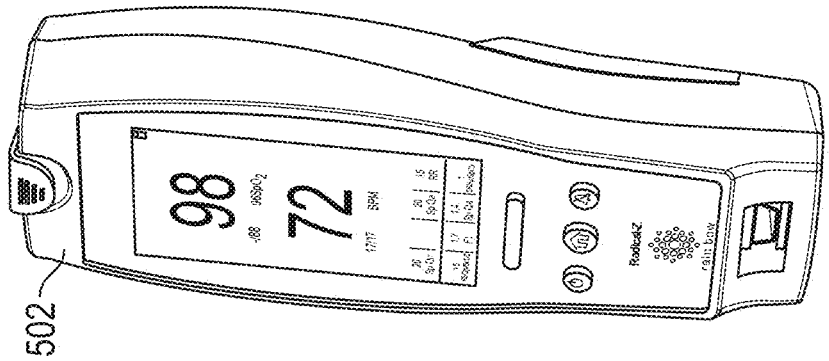

FIG. 5 illustrates a perspective view of exemplary portable patient monitors 502 and 504 undocked from the hub 100 of FIG. 1, according to an embodiment of the disclosure. As shown in FIG. 5, the monitor 502 may be removed and other monitors, like monitor 504 may be provided. The docking station 106 includes an additional docking station 506 that mechanically mates with the original docking station 106 and presents a form factor mechanically matable with monitor 504. In an embodiment, the monitor 504 mechanically and electrically mates with the stacked docking stations 506 and 106 of hub 100. As can be readily appreciated by and artisan from the disclosure herein, the stackable function of the docking stations provides the hub 100 with an extremely flexible mechanism for charging, communicating, and interfacing with a wide variety of patient monitoring devices. As noted above, the docking stations may be stacked, or in other embodiments, removed and replaced.

Figure 6:
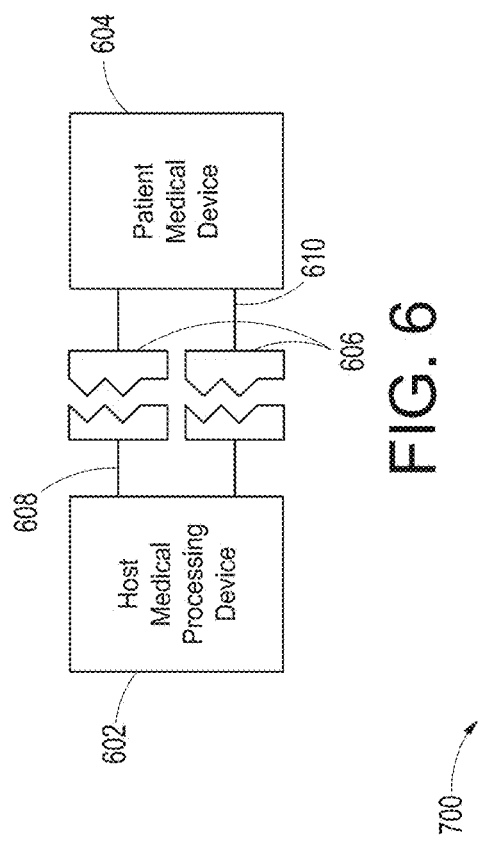
FIG. 6 illustrates a simplified block diagram of traditional patient device electrical isolation principles.

FIG. 6 illustrates a simplified block diagram of traditional patient electrical isolation principles. As shown in FIG. 6, a host device 602 is generally associated with a patient device 604 through communication and power. As the patient device 604 often comprises electronics proximate or connected to a patient, such as sensors or the like, certain safety requirements dictate that electrical surges of energy from, for example, the power grid connected to the host device, should not find an electrical path to the patient. This is generally referred to a "patient isolation" which is a term known in the art and includes herein the removing of direct uninterrupted electrical paths between the host device 602 and the patient device 604. Such isolation is accomplished through, for example, isolation devices 606 on power conductors 608 and communication conductors 610. Isolation devices 606 can include transformers, optical devices that emit and detect optical energy, and the like. Use of isolation devices, especially on power conductors, can be expensive component wise, expensive size wise, and drain power. Traditionally, the isolation devices were incorporated into the patient device 604, however, the patient devices 604 are trending smaller and smaller and not all devices incorporate isolation.

Figure 7B:
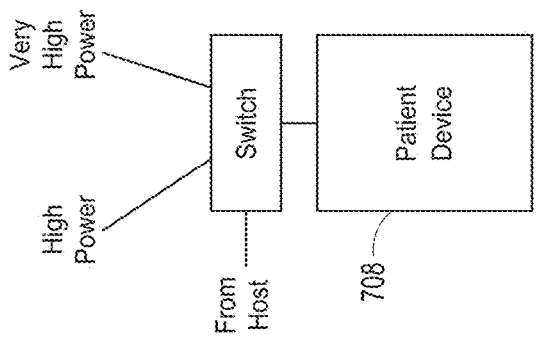
FIG. 7A illustrates a simplified block diagram of an exemplary optional patient device isolation system according to an embodiment of the disclosure, while FIG. 7B adds exemplary optional non-isolation power levels for the system of FIG. 7A, also according to an embodiment of the disclosure.
Figure 7A:
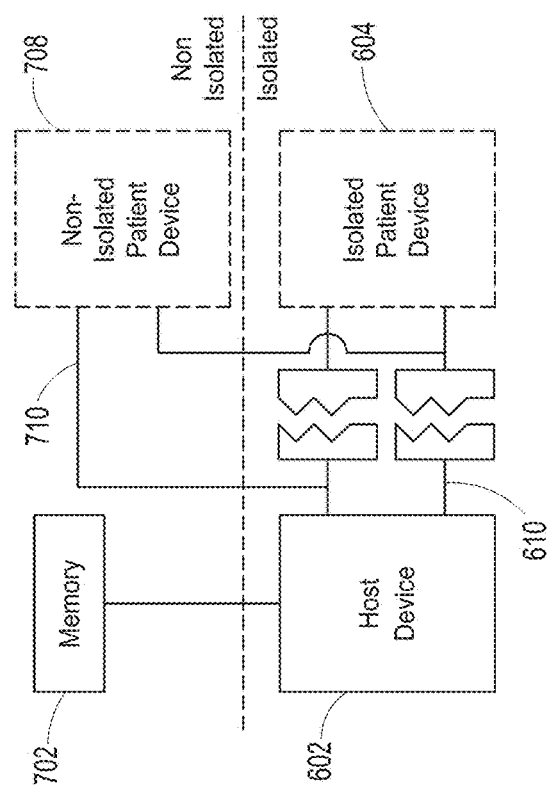

FIG. 7A illustrates a simplified block diagram of an exemplary optional patient isolation system according to an embodiment of the disclosure. As shown in FIG. 7A, the host device 602 communicates with an isolated patient device 604 through isolation devices 606. However, a memory 702 associated with a particular patient device informs the host 602 whether that device needs isolated power. If a patient device 708 does not need isolated power, such as some types of cuffs, infusion pumps, ventilators, or the like, then the host 602 can provide non-isolated power through signal path 710. This power may be much higher that what can cost-effectively be provided through the isolated power conductor 608. In an embodiment, the non-isolated patient devices 708 receive isolated communication as such communication is typically at lower voltages and is not cost prohibitive. An artisan will recognize from the disclosure herein that communication could also be non-isolated. Thus, FIG. 7A shows a patient isolation system 700 that provides optional patient isolation between a host 602 and a wide variety of potential patient devices 604, 708. In an embodiment, the hub 100 includes the channel ports 212 incorporating similar optional patient isolation principles.

FIG. 7B adds an exemplary optional non-isolation power levels for the system of FIG. 7A according to an embodiment of the disclosure. As shown in FIG. 7B, once the host 602 understands that the patient device 604 comprises a self-isolated patient device 708, and thus does not need isolated power, the host 602 provides power through a separate conductor 710. Because the power is not isolated, the memory 702 may also provide power requirements to the host 602, which may select from two or more voltage or power levels. In FIG. 7B, the host 602 provides either high power, such as about 12 volts, but could have a wide range of voltages or very high power such as about 24 volts or more, but could have a wide range of voltages, to the patient device 708. An artisan will recognize that supply voltages can advantageously be altered to meet the specific needs of virtually any device 708 and/or the memory could supply information to the host 602 which provided a wide range of non-isolated power to the patient device 708.

Moreover, using the memory 702, the host 602 may determine to simply not enable any unused power supplies, whether that be the isolated power or one or more of the higher voltage non-isolated power supplies, thereby increasing the efficiency of the host.

Figure 8:
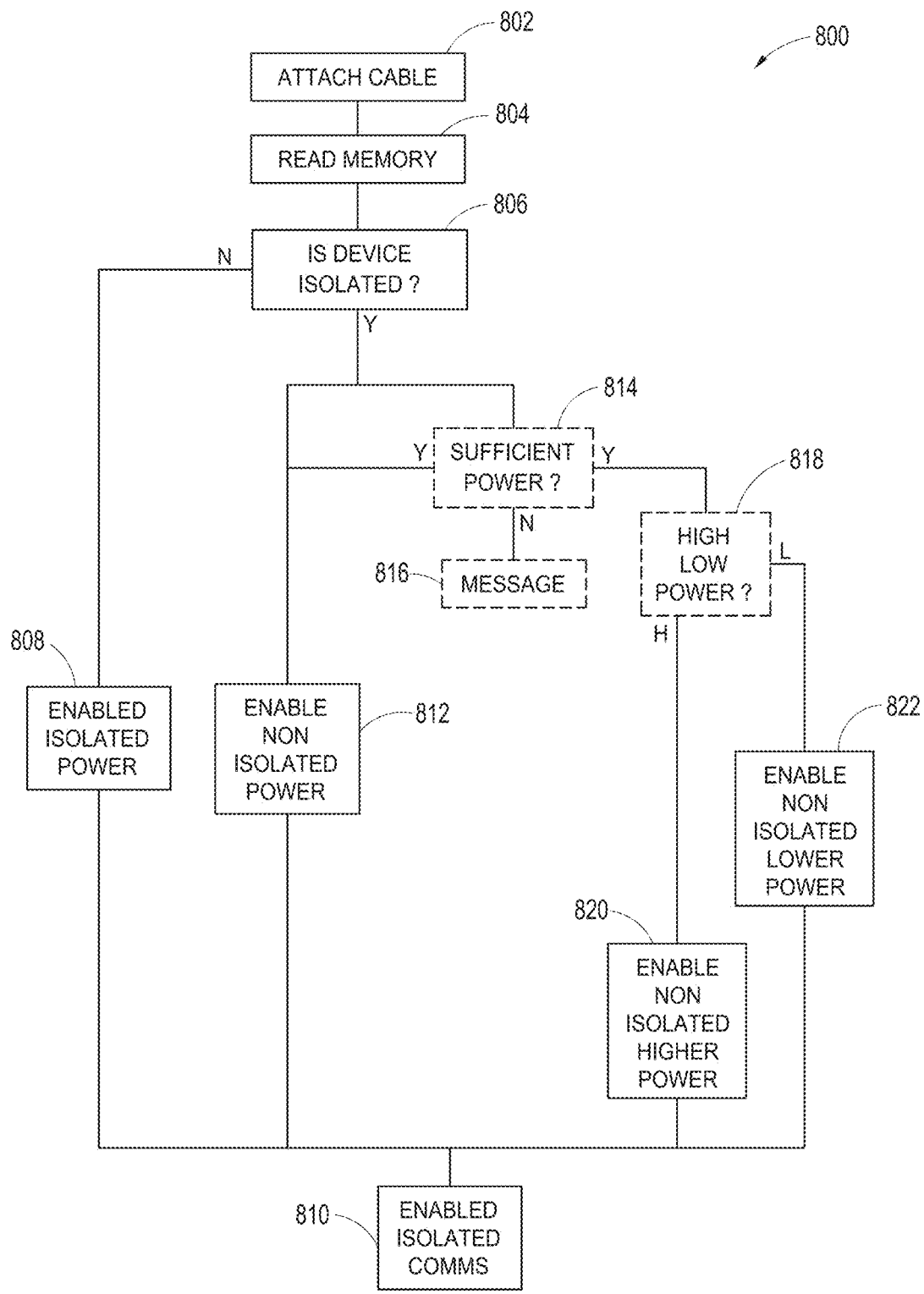
FIG. 8 illustrates a simplified exemplary universal medical connector configuration process, according to an embodiment of the disclosure.

FIG. 8 illustrates a simplified exemplary universal medical connector configuration process 800, according to an embodiment of the disclosure. As shown in FIG. 8, the process includes step 802, where a cable is attached to a universal medical connector incorporating optional patient isolation as disclosed in the foregoing. In step 804, the host device 602 or the hub 100, more specifically, the channel data board 316 or EPROM reader of the instrument board, reads the data stored in the memory 702 and in step 806, determines whether the connecting device requires isolated power. In step 808, when the isolated power is required, the hub 100 may advantageously enable isolated power and in step 810, enable isolated communications. In step 806, when isolated power is not needed, the hub 100 may simply in optional step 812 enable non-isolated power and in embodiments where communications remain isolated, step 810 enable isolated communications. In other optional embodiments, in step 806, when isolated power is not needed, the hub 100 in step 814 may use information from memory 702 to determine the amount of power needed for the patient device 708. When sufficient power is not available, because for example, other connected devices are also using connected power, in step 816 a message may be displayed indicating the same and power is not provided. When sufficient power is available, optional step 812 may enable non-isolated power. Alternatively, optional step 818 may determine whether memory 702 indicates higher or lower power is desired. When higher power is desired, the hub 100 may enable higher power in step 820 and when not, may enable lower power in step 822. The hub 100 in step 810 then enables isolated communication. In an embodiment, the hub 100 in step 818 may simply determine how much power is needed and provide at least sufficient power to the self-isolated device 708.

An artisan will recognize from the disclosure herein that hub 100 may not check to see if sufficient power is available or may provide one, two or many levels of non-isolated voltages based on information from the memory 702.

Figure 9A:
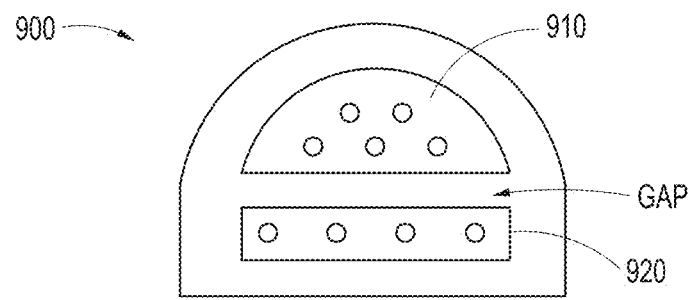
FIGS. 9A-9B illustrate simplified block diagrams of exemplary universal medical connectors having a size and shape smaller in cross section than tradition isolation requirements.
Figure 9B:
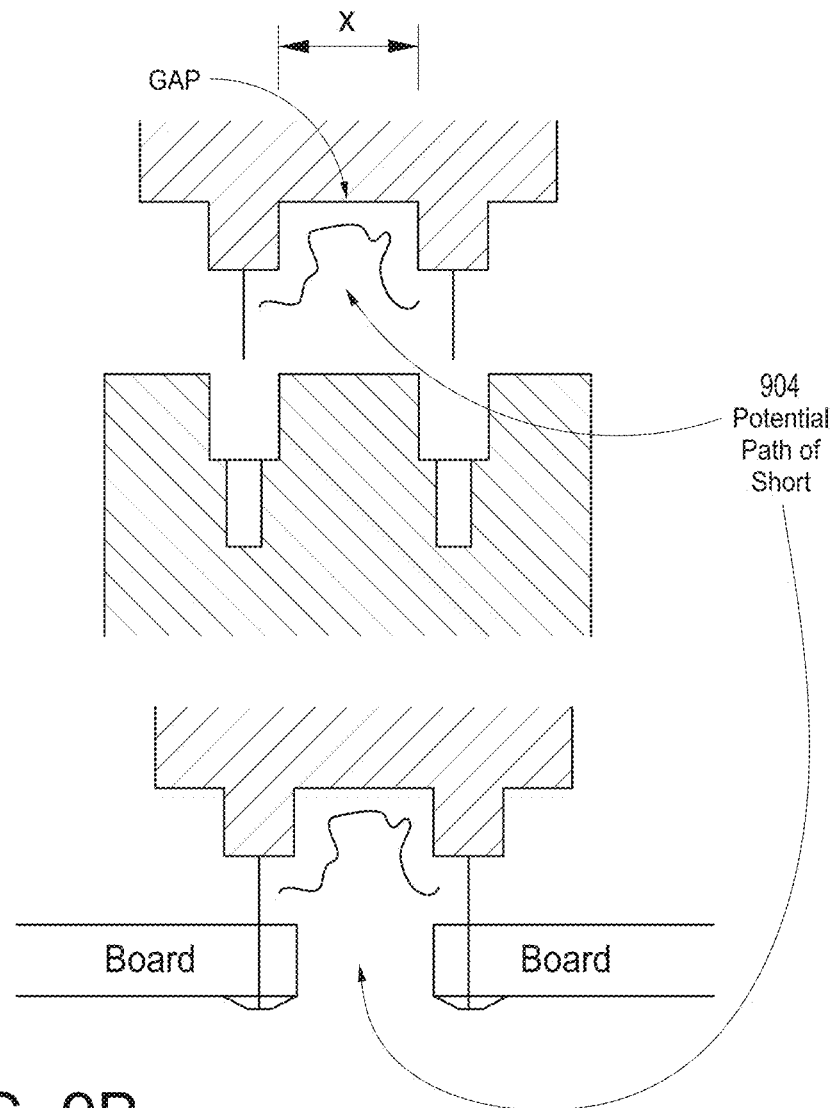

FIGS. 9A and 9B illustrate simplified block diagrams of exemplary universal medical connectors 900 having a size and shape smaller in cross section than tradition isolation requirements. In an embodiment, the connector 900 physically separates non-isolated signals on one side 910 from isolated signals on another side 920, although the sides could be reversed. The gap between such separations may be dictated at least in part by safety regulations governing patient isolation. In an embodiment, the distance between the sides 910 and 920 may appear to be too small.

As shown from a different perspective in FIG. 9B, the distance between connectors "x" appears small. However, the gap causes the distance to includes a non-direct path between conductors. For example, any short would have to travel path 904, and the distance of such path is within or beyond such safety regulations, in that the distance is greater than "x." It is noteworthy that the non-straight line path 904 occurs throughout the connector, such as, for example, on the board connector side where solder connects various pins to a PCB board.

Figure 10:
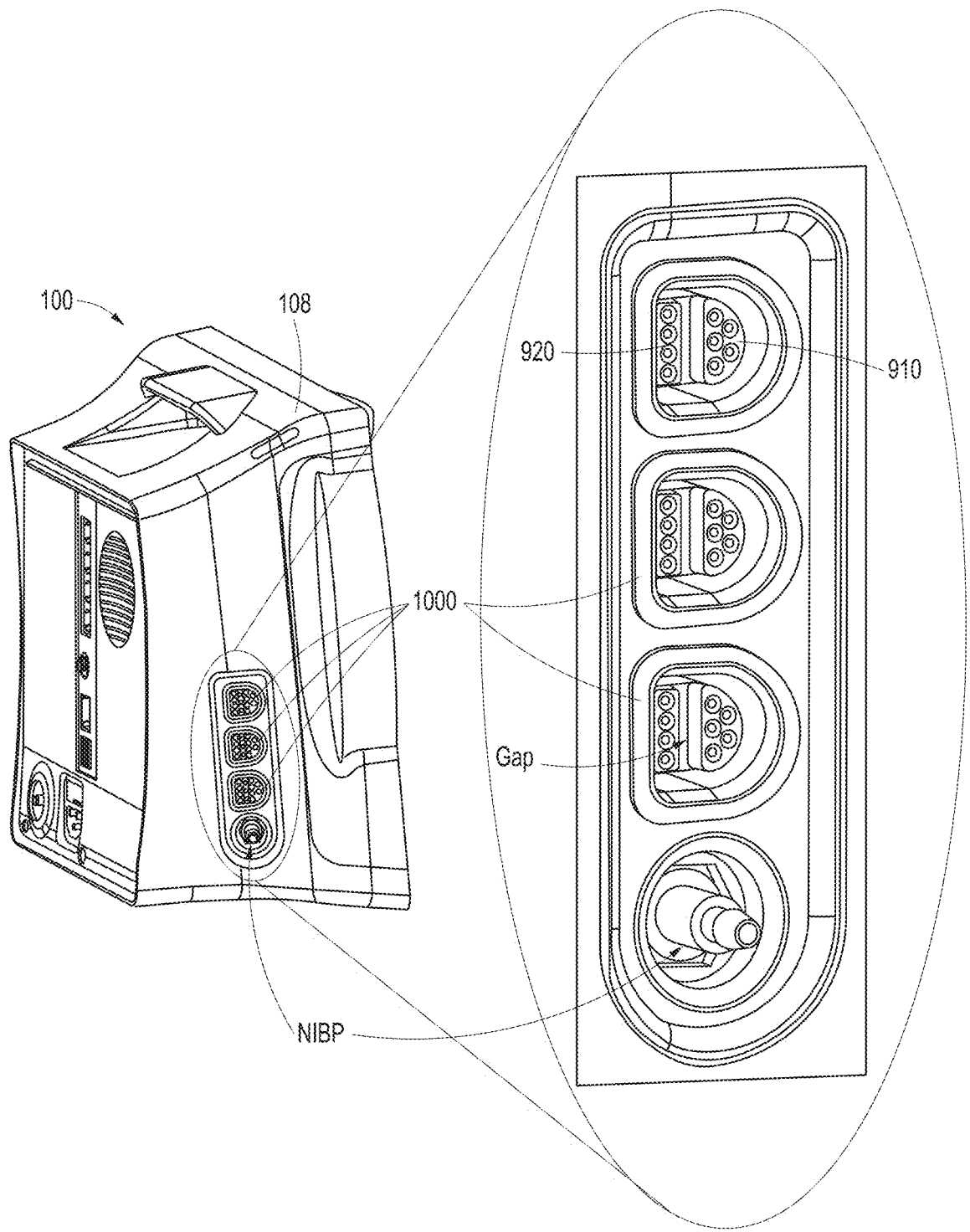
FIG. 10 illustrates a perspective view of a side of the hub of FIG. 1, showing exemplary instrument-side channel inputs for exemplary universal medical connectors, according to an embodiment of the disclosure.

FIG. 10 illustrates a perspective view of a side of the hub 100 of FIG. 1, showing exemplary instrument-side channel inputs 1000 as exemplary universal medical connectors. As shown in FIG. 10, the inputs include the non-isolated side 910, the isolated side 920, and the gap. In an embodiment, the memory 710 communicates through pins on the non-isolated side.

Figure 11A:
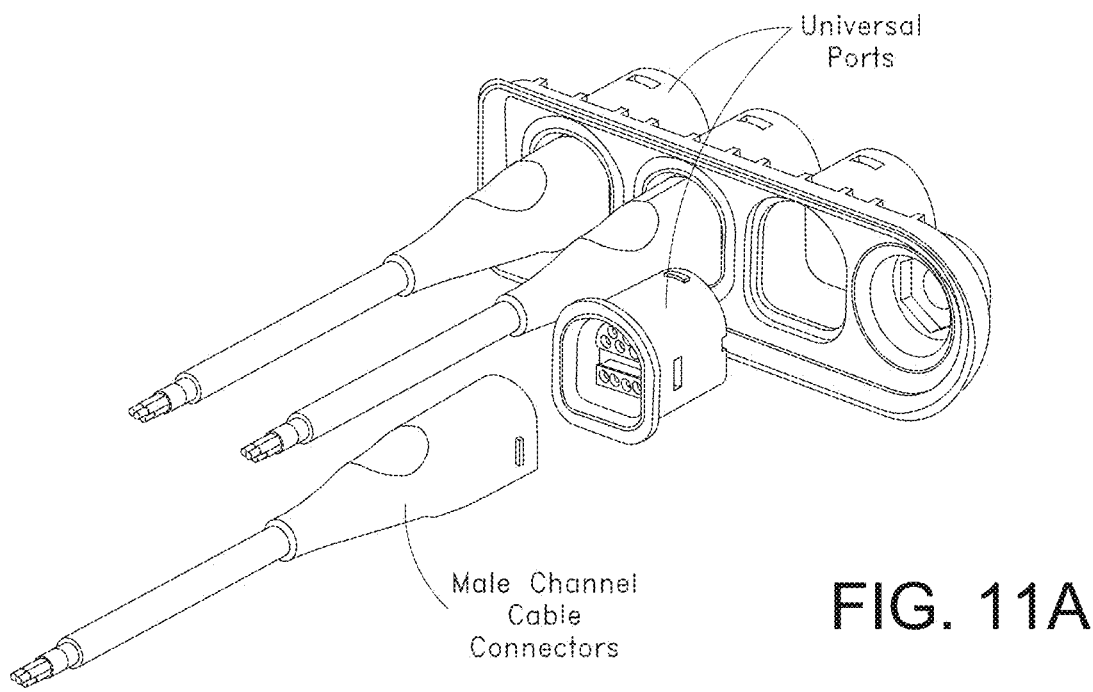
Figure 11B:
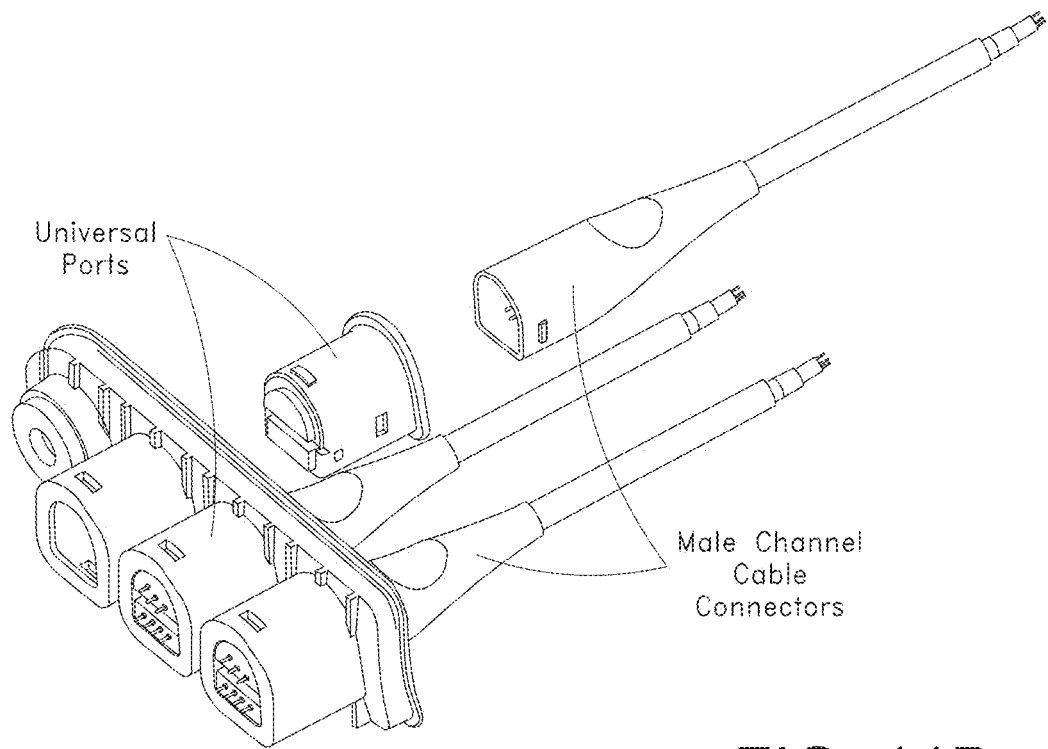
Figure 11C:
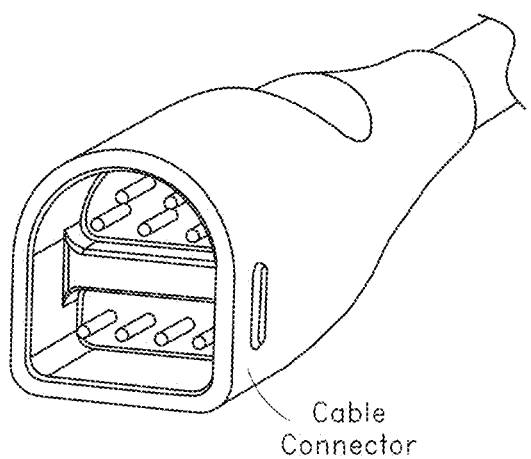
Figure 11D:
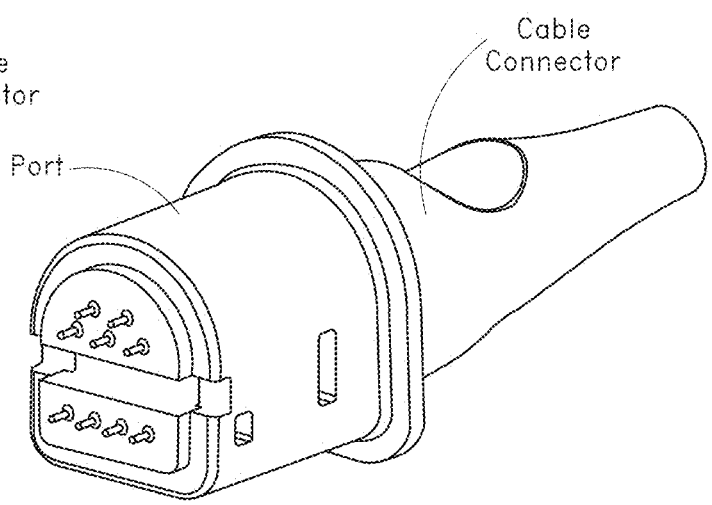
Figure 11E:
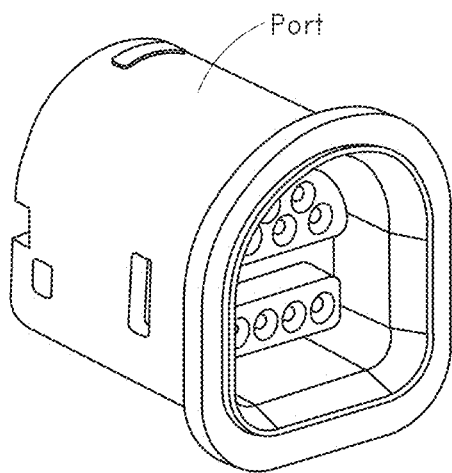
Figure 11F:
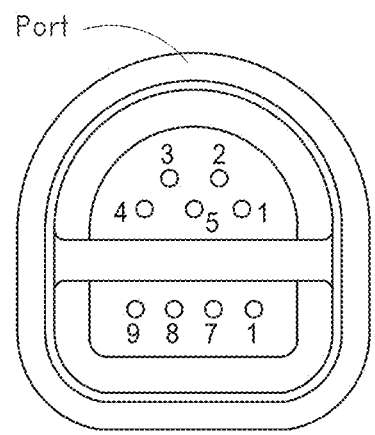
Figure 11H:
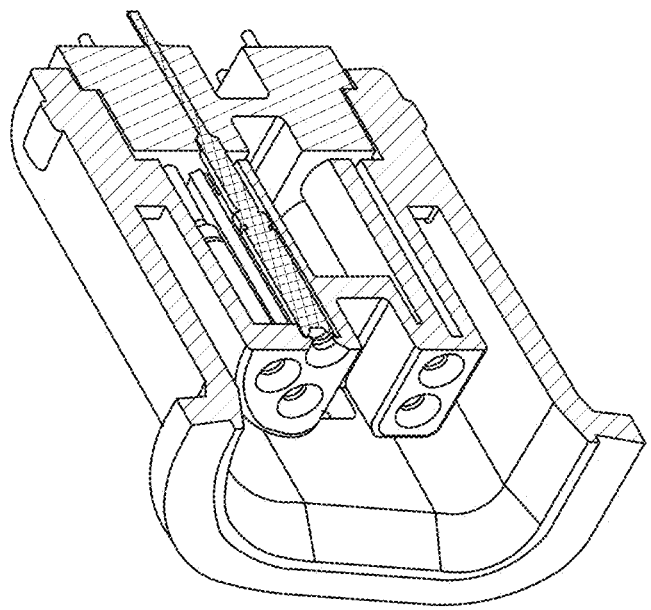
Figure 11H:
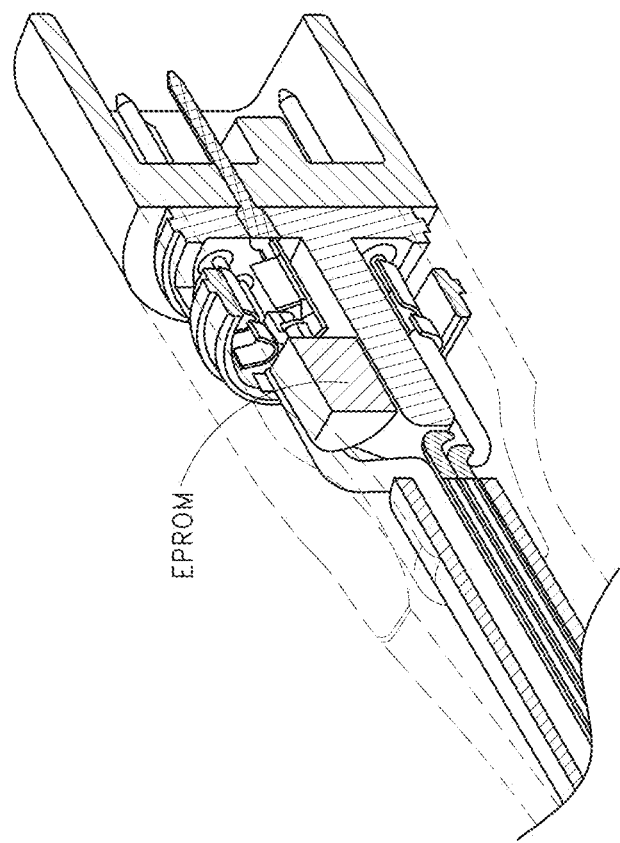
Figure 11J:
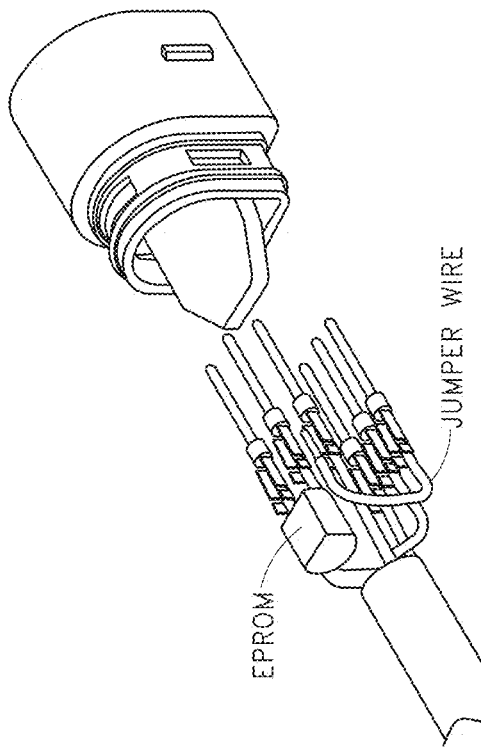
Figure 11I:
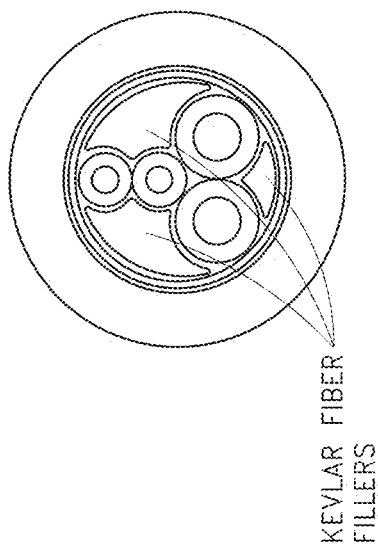
Figure 11K:
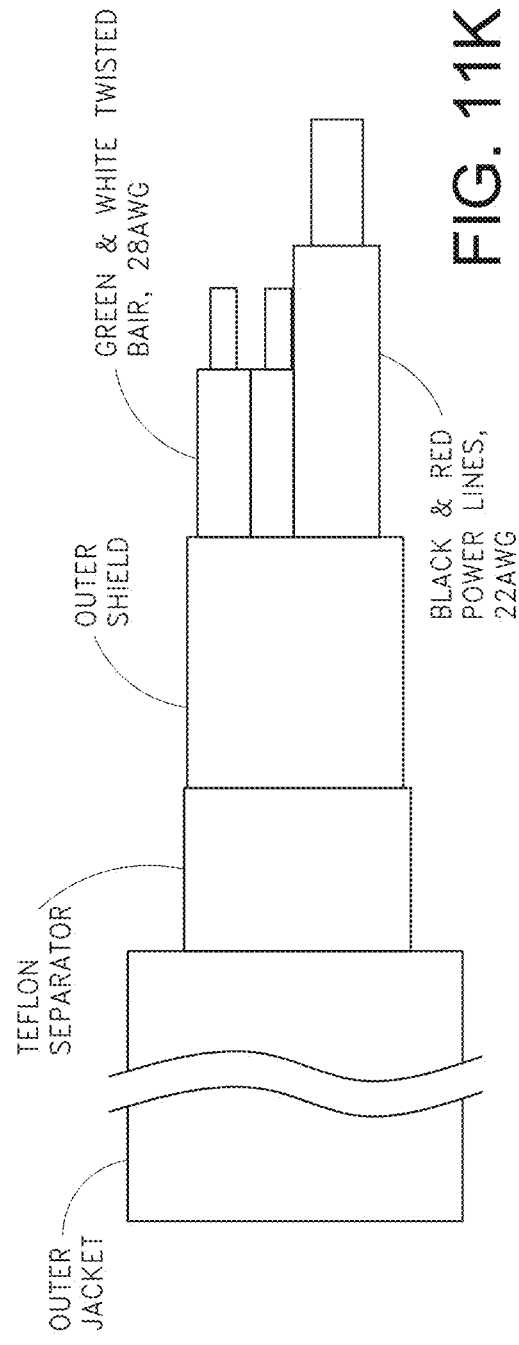

FIGS. 11A-11K illustrate various views of exemplary male and mating female universal medical connectors, according to embodiments of the disclosure. For example, FIGS. 11G1 and 11G2 shows various preferred but not required sizing, and FIG. 11H shows incorporation of electronic components, such as the memory 702 into the connectors. FIGS. 11I-11K illustrate wiring diagrams and cabling specifics of the cable itself as it connects to the universal medical connectors.

Figure 12:
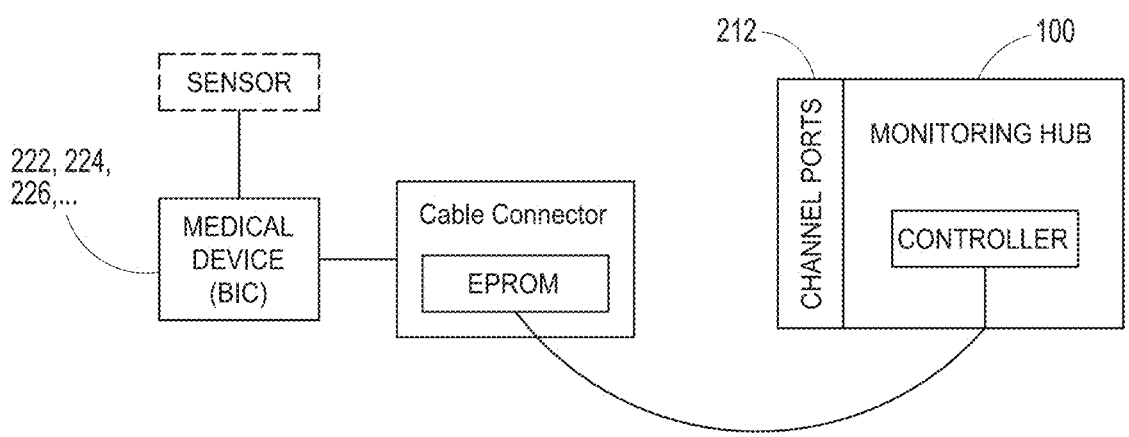
FIG. 12 illustrates a simplified block diagram of a channel system for the hub of FIG. 1, according to an embodiment of the disclosure.

FIG. 12 illustrates a simplified block diagram of a channel system for the hub of FIG. 1, according to an embodiment of the disclosure. As shown in FIG. 12, a male cable connector, such as those shown in FIG. 11 above, includes a memory such as an EPROM. The memory advantageously stores information describing the type of data the hub 100 can expect to receive, and how to receive the same. A controller of the hub 100 communicates with the EPROM to negotiate how to receive the data, and if possible, how to display the data on display 104, alarm when needed, and the like. For example, a medical device supplier may contact the hub provider and receive a software developers' kit ("SDK") that guides the supplier through how to describe the type of data output from their device. After working with the SDK, a map, image, or other translation file may advantageously be loaded into the EPROM, as well as the power requirements and isolation requirements discussed above. When the channel cable is connected to the hub 100 through the channel port 212, the hub 100 reads the EPROM and the controller of the hub 100 negotiates how to handle incoming data.

Figure 13:
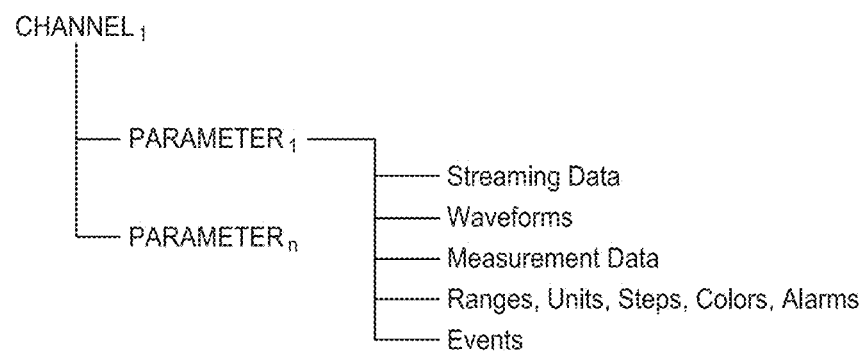
FIG. 13 illustrates an exemplary logical channel configuration, according to an embodiment of the disclosure.

FIG. 13 illustrates an exemplary logical channel configuration that may be stored in the EPROM of FIG. 12. As shown in FIG. 13, each incoming channel describes one or more parameters. Each parameter describes whatever the hub 100 should know about the incoming data. For example, the hub 100 may want to know whether the data is streaming data, waveform data, already determined parameter measurement data, ranges on the data, speed of data delivery, units of the data, steps of the units, colors for display, alarm parameters and thresholds, including complex algorithms for alarm computations, other events that are parameter value driven, combinations of the same or the like. Additionally, the parameter information may include device delay times to assist in data synchronization or approximations of data synchronization across parameters or other data received by the hub 100. In an embodiment, the SDK presents a schema to the device supplier which self-describes the type and order of incoming data. In an embodiment, the information advantageously negotiates with the hub 100 to determine whether to apply compression and/or encryption to the incoming data stream.

Such open architecture advantageously provides device manufacturers the ability to port the output of their device into the hub 100 for display, processing, and data management as disclosed in the foregoing. By implementation through the cable connector, the device manufacturer avoids any reprogramming of their original device; rather, they simply let the hub 100 know through the cable connector how the already existing output is formatted. Moreover, by describing the data in a language already understood by the hub 100, the hub 100 also avoids software upgrades to accommodate data from "new-to-the-hub" medical devices.

Figure 14:
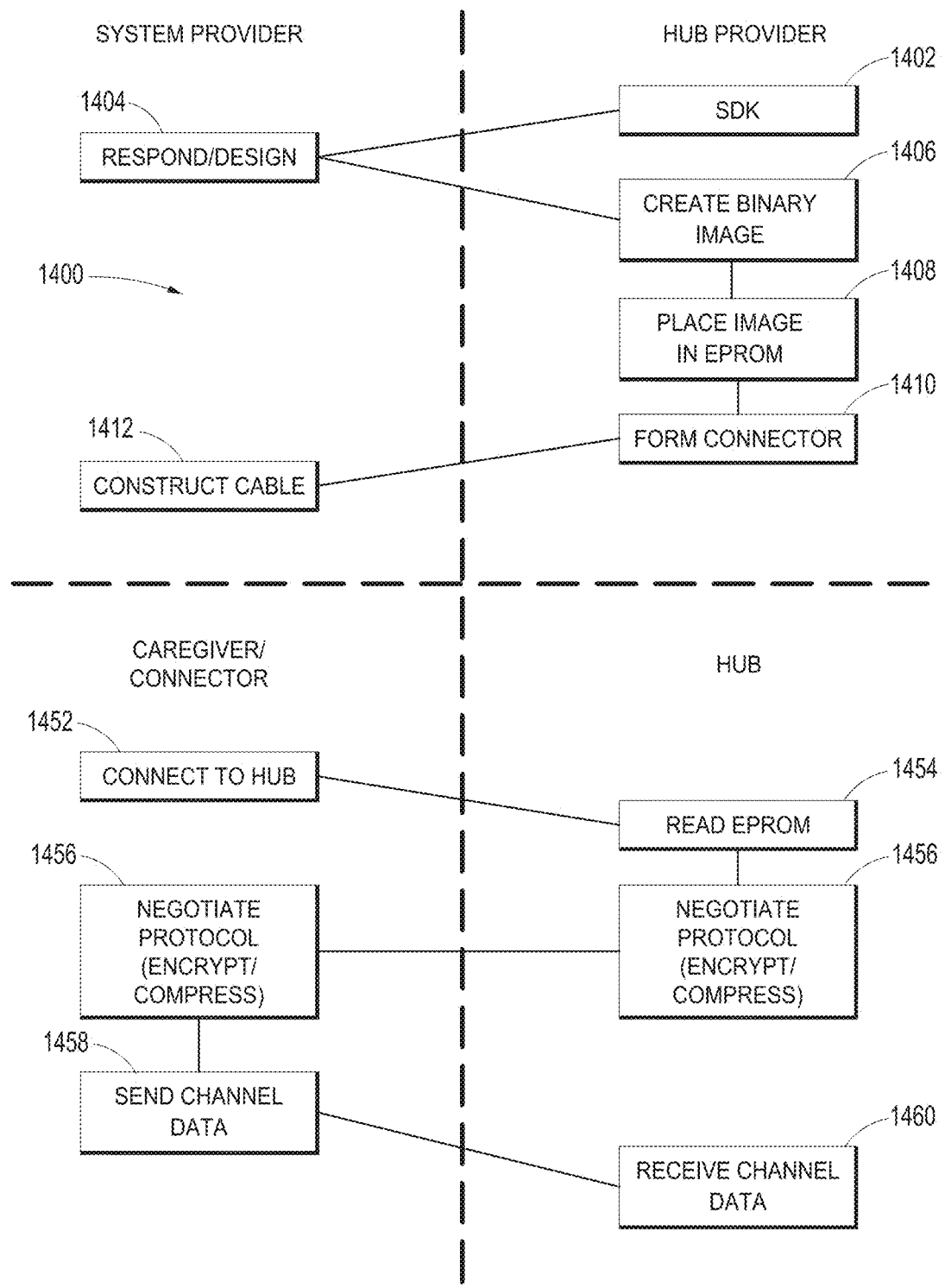
FIG. 14 illustrates a simplified exemplary process for constructing a cable and configuring a channel according to an embodiment of the disclosure.

FIG. 14 illustrates a simplified exemplary process for configuring a channel according to an embodiment of the disclosure. As shown in FIG. 14, the hub provider provides a device manufacturer with an SDK in step 1402, who in turn uses the SDK to self-describe the output data channel from their device in step 1404. In an embodiment, the SDK is a series of questions that guide the development, in other embodiments, the SDK provides a language and schema to describe the behavior of the data.

Once the device provider describes the data, the hub provider creates a binary image or other file to store in a memory within a cable connector in step 1405; however, the SDK may create the image and simply communicated it to the hub provider. The cable connector is provided as an OEM part to the provider in step 1410, who constructs and manufactures the cable to mechanically and electrically mate with output ports on their devices in step 1412.

Once a caregiver has the appropriately manufactured cable, with one end matching the device provider's system and the other OEM'ed to match the hub 100 at its channel ports 212, in step 1452 the caregiver can connect the hub between the devices. In step 1454, the hub 100 reads the memory, provides isolated or non-isolated power, and the cable controller and the hub 100 negotiate a protocol or schema for data delivery. In an embodiment, a controller on the cable may negotiated the protocol, in an alternative embodiment, the controller of the hub 100 negotiates with other processors on the hub the particular protocol. Once the protocol is set, the hub 100 can use, display and otherwise process the incoming data stream in an intelligent manner.

Through the use of the universal medical connectors described herein, connection of a myriad of devices to the hub 100 is accomplished through straightforward programming of a cable connector as opposed to necessitating software upgrades to each device.

Figure 15:
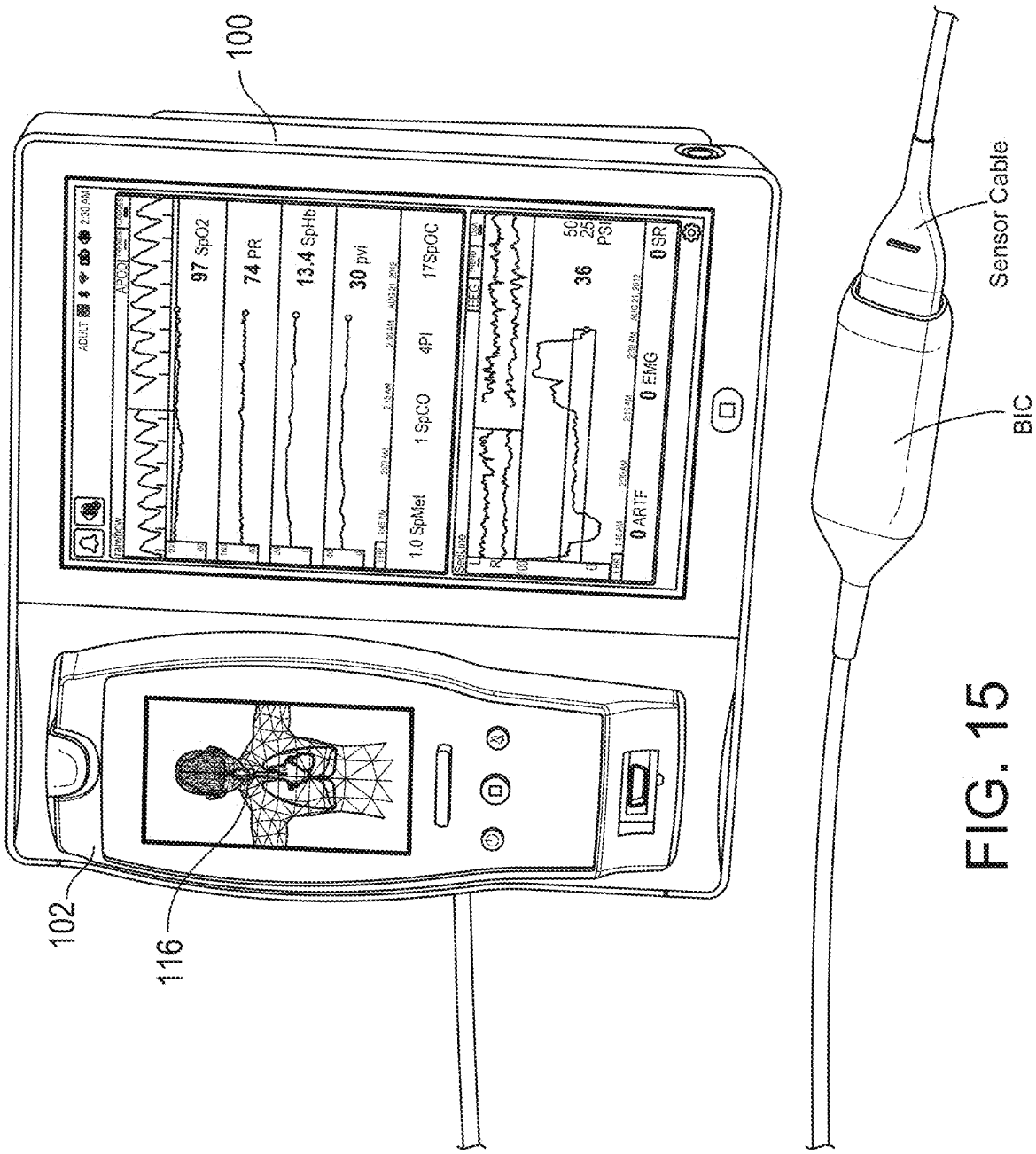
FIG. 15 illustrates a perspective view of the hub of FIG. 1, including an exemplary attached board-in-cable to form an input channel, according to an embodiment of the disclosure.

FIG. 15 illustrates a perspective view of the hub of FIG. 1 including an exemplary attached board-in-cable ("BIC") to form an input channel according to an embodiment of the disclosure. As shown in FIG. 15, a SEDLine depth of consciousness board communicates data from an appropriate patient sensor to the hub 100 for display and caregiver review. As described, the provider of the board need only use the SDK to describe their data channel, and the hub 100 understands how to present the data to the caregiver.

Figure 16:
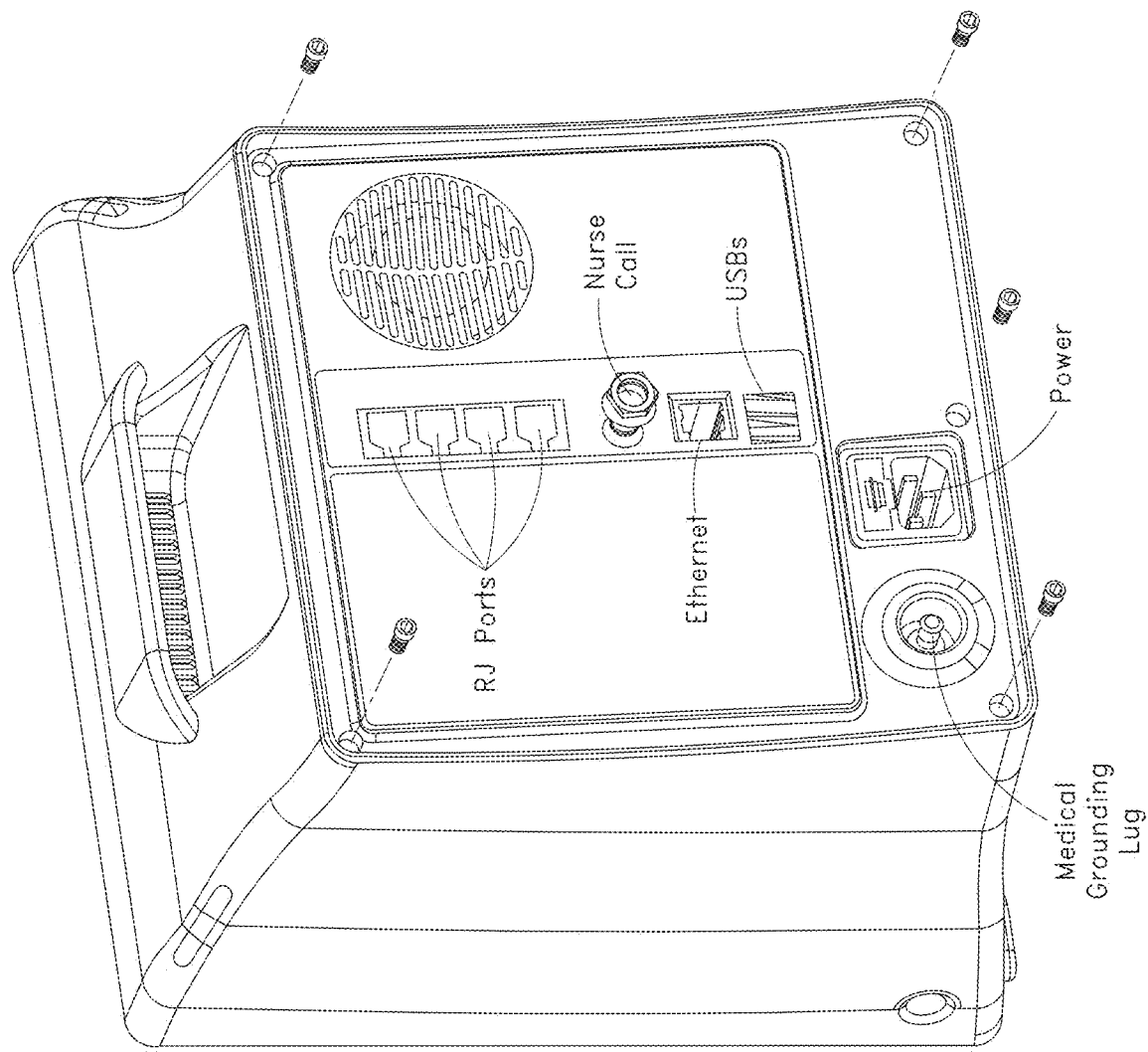
FIG. 16 illustrates a perspective view of a back side of the hub of FIG. 1, showing an exemplary instrument-side serial data inputs, according to an embodiment of the disclosure.

FIG. 16 illustrates a perspective view of a back side of the hub 100 of FIG. 1, showing an exemplary serial data inputs. In an embodiment, the inputs include such as RJ 45 ports. As is understood in the art, these ports include a data ports similar to those found on computers, network routers, switches and hubs. In an embodiment, a plurality of these ports are used to associate data from various devices with the specific patient identified in the hub 100. FIG. 16 also shows a speaker, the nurse call connector, the Ethernet connector, the USBs, a power connector and a medical grounding lug.

Figure 17A:
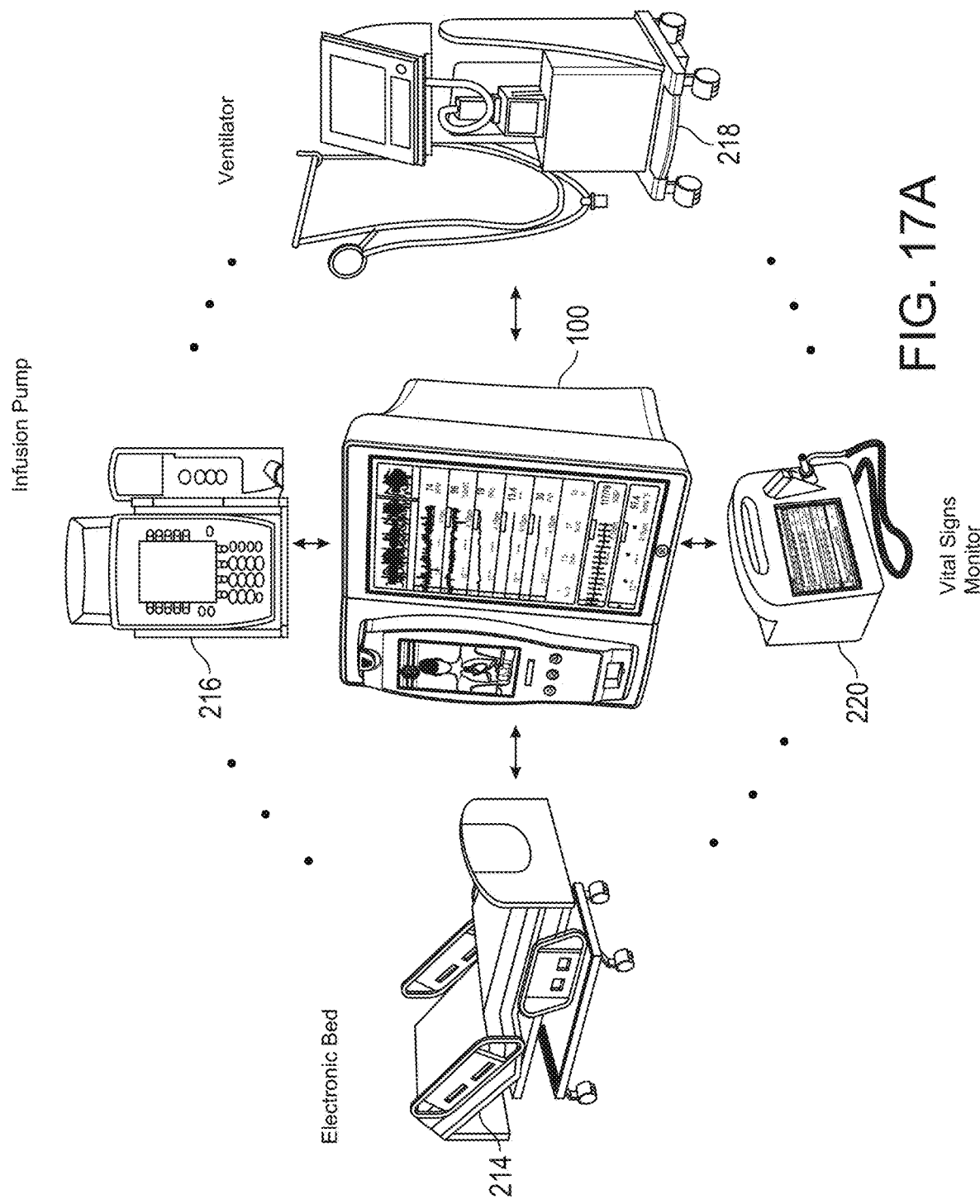
FIG. 17A illustrates an exemplary monitoring environment with communication through the serial data connections of FIG. 16.

FIG. 17A illustrates an exemplary monitoring environment with communication through the serial data connections of the hub 100 of FIG. 1, according to an embodiment of the disclosure. As shown and as discussed in the foregoing, the hub 100 may use the serial data ports 210 to gather data from various devices within the monitoring environment, including an electronic bed, infusion pumps, ventilators, vital sign monitors, and the like. The difference between the data received from these devices and that received through the channel ports 212 is that the hub 100 may not know the format or structure of this data. The hub 100 may not display information from this data or use this data in calculations or processing. However, porting the data through the hub 100 conveniently associates the data with the specifically monitored patient in the entire chain of caregiver systems, including the foregoing server 214 and backend systems 206. In an embodiment, the hub 100 may determine sufficient information about the incoming data to attempt to synchronize it with data from the hub 100.

Figure 17B:
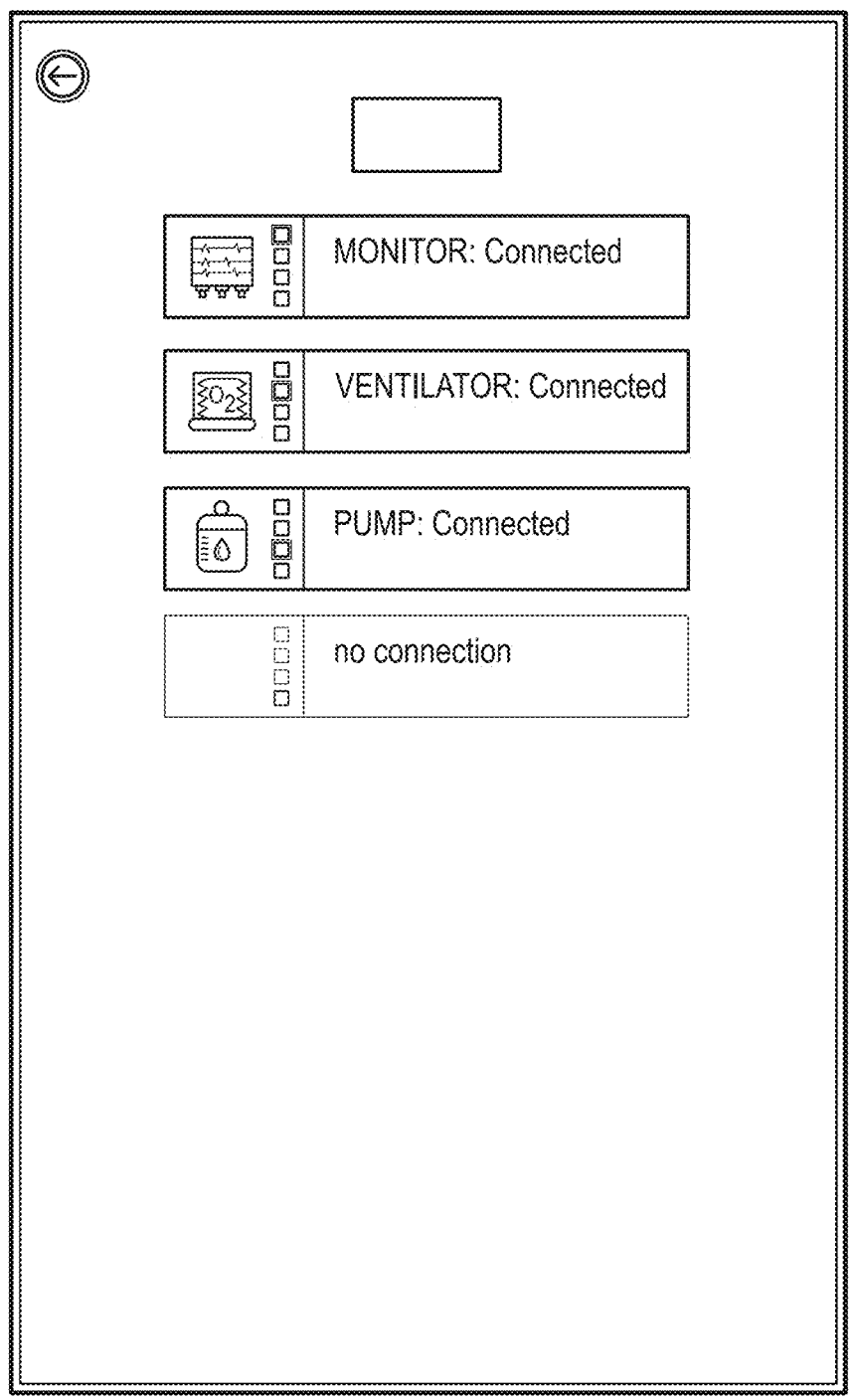
FIG. 17B illustrates an exemplary connectivity display of the hub of FIG. 1, according to embodiments of the disclosure.

In FIG. 17B, a control screen may provide information on the type of data being received. In an embodiment, a green light next to the data indicates connection to a device and on which serial input the connection occurs.

Figure 18:
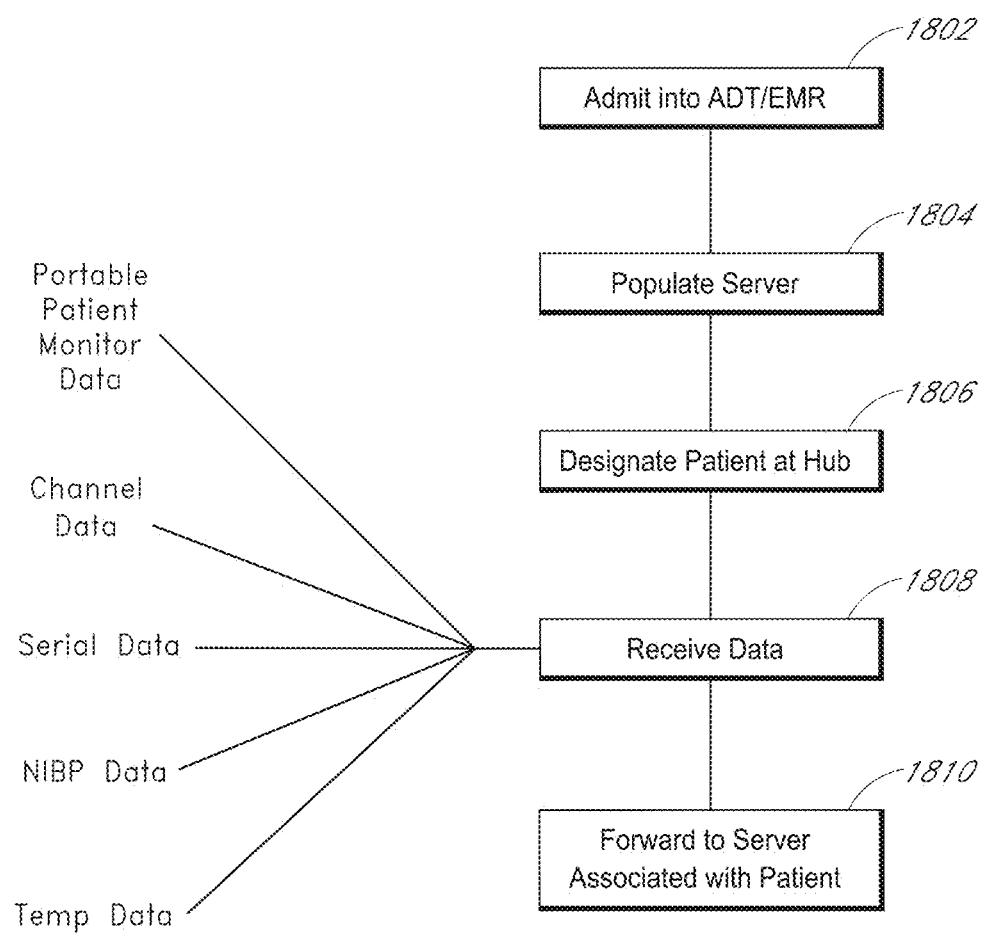
FIG. 18 illustrates a simplified exemplary patient data flow process, according to an embodiment of the disclosure.

FIG. 18 illustrates a simplified exemplary patient data flow process, according to an embodiment of the disclosure. As shown, once a patient is admitted into the caregiver environment at step 1802, data about the patient is populated on the caregiver backend systems 206. The server 214 may advantageously acquire or receive this information in step 1804, and then make it accessible to the hub 100. When the caregiver at step 1806 assigns the hub 100 to the patient, the caregiver simply looks at the presently available patient data and selects the particular patient being currently monitored. The hub 100 at step 1808 then associates the measurement, monitoring and treatment data it receives and determines with that patient. The caregiver need not again associate another device with the patient so long as that device is communicating through the hub 100 by way of (1) the docking station, (2) the universal medical connectors, (3) the serial data connectors, or (4) other communication mechanisms known to an artisan. At step 1810, some or the entirety of the received, processed and/or determined data is passed to the server systems discussed above.

Figure 19A:
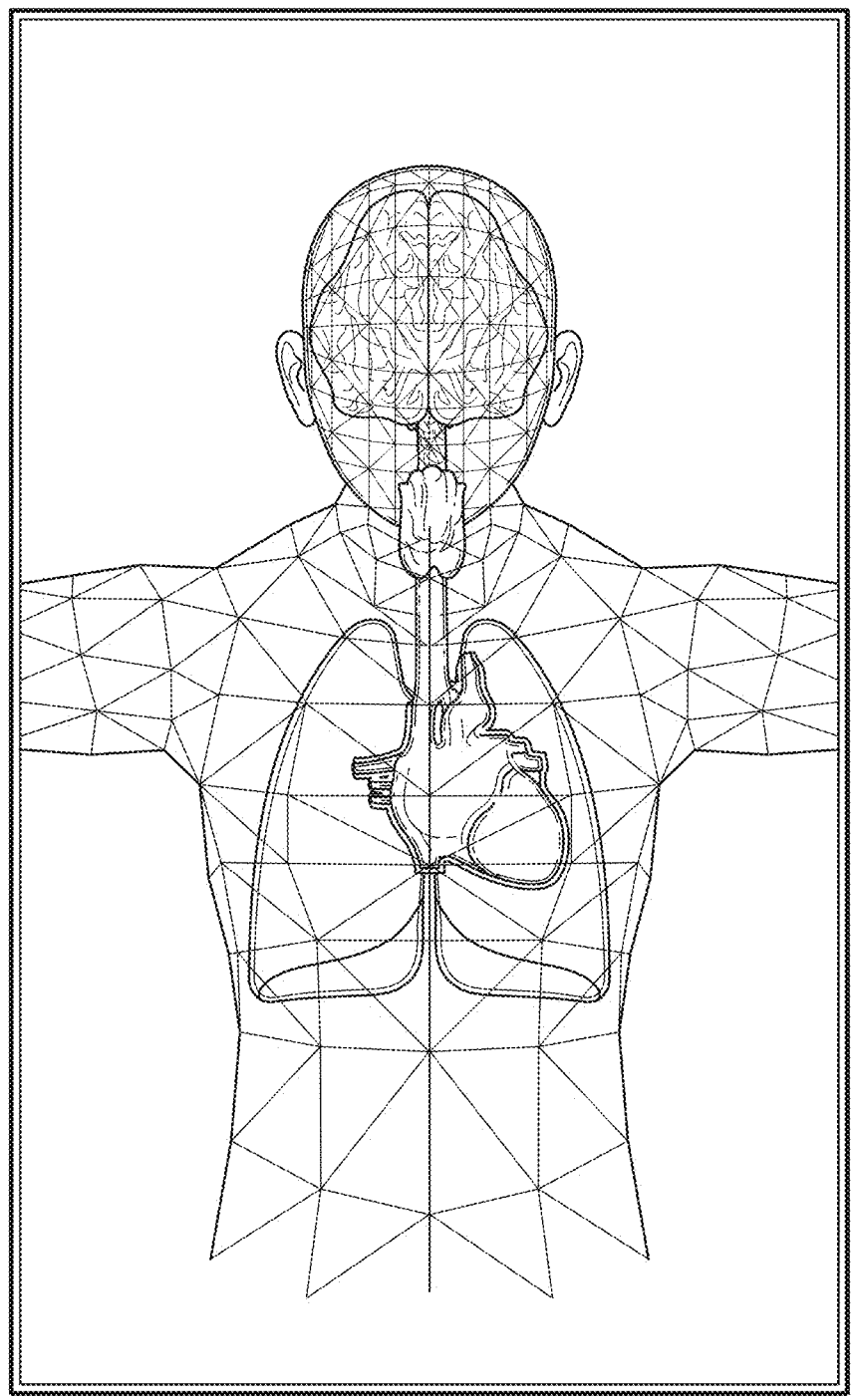
FIGS. 19A-19J illustrate exemplary displays of anatomical graphics for the portable patient monitor of FIG. 1 docked with the hub of FIG. 1, according to embodiments of the disclosure.

FIGS. 19A-19J illustrate exemplary displays of anatomical graphics for the portable patient monitor docked with the hub 100 of FIG. 1, according to embodiments of the disclosure. As shown in FIG. 19A, the heart, lungs and respiratory system are shown while the brain is not highlighted. Thus, a caregiver can readily determine that depth of consciousness monitoring or brain oximetry systems are not currently communicating with the hub 100 through the portable patient monitor connection or the channel data ports. However, it is likely that acoustic or other respiratory data and cardiac data is being communicated to or measured by the hub 100. Moreover, the caregiver can readily determine that the hub 100 is not receiving alarming data with respect to the emphasized body portions. In an embodiment, the emphasized portion may animate to show currently measured behavior or, alternatively, animate in a predetermined fashion.

Figure 19B:
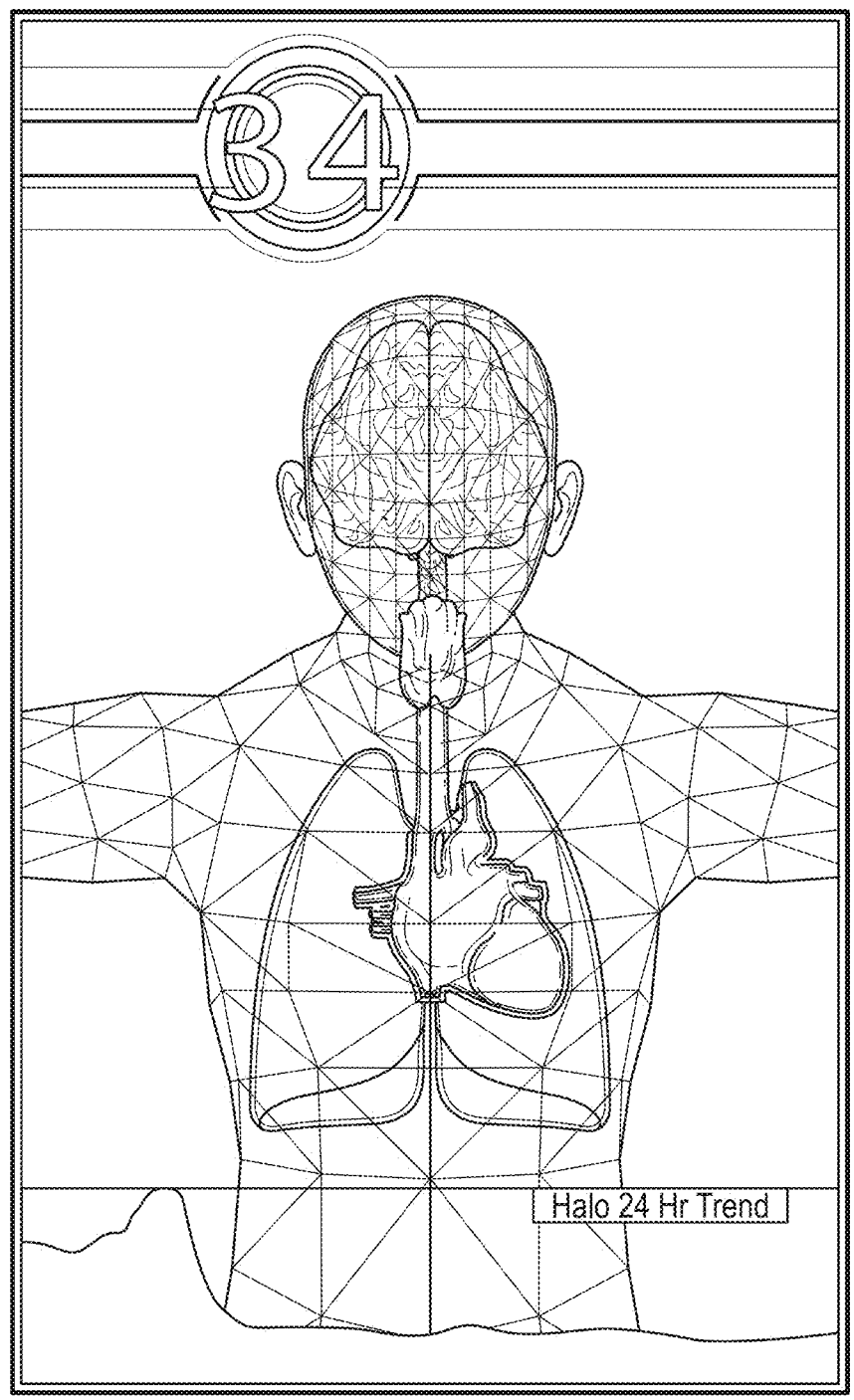
Figure 19C:
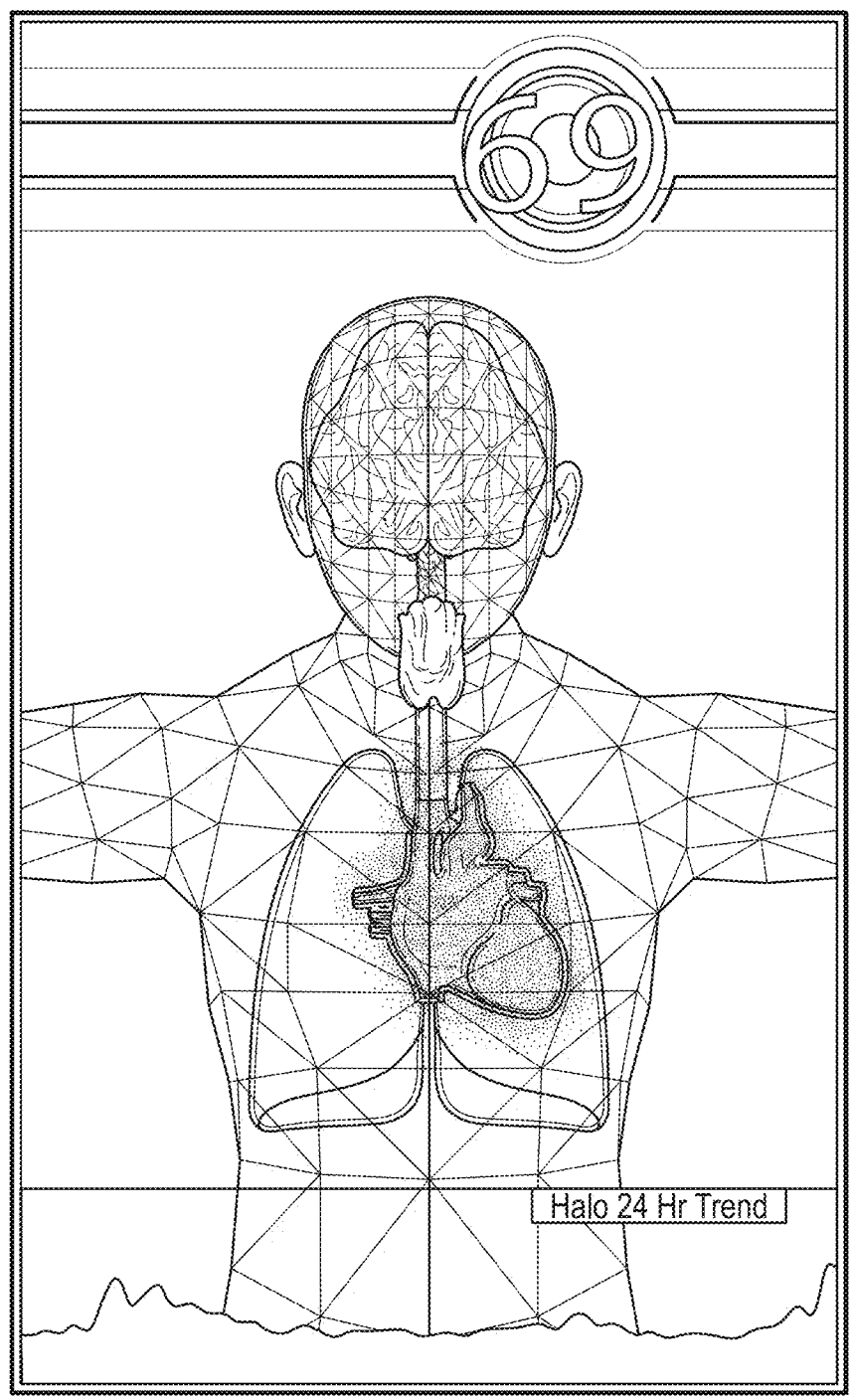

FIG. 19B shows the addition of a virtual channel showing an indication of wellness. As shown in FIG. 19B, the indication is positive as it is a "34" on an increasingly severity scale to "100." The wellness indication may also be shaded to show problems. In contrast to FIG. 19B, FIG. 19C shows a wellness number that is becoming or has become problematic and an alarming heart graphic. Thus, a caregiver responding to a patient alarm on the hub 100 or otherwise on another device or system monitoring or treating the patient can quickly determine that a review of vital signs and other parameters relating to heart function is needed to diagnose and/or treat the patient.

Figure 19D:
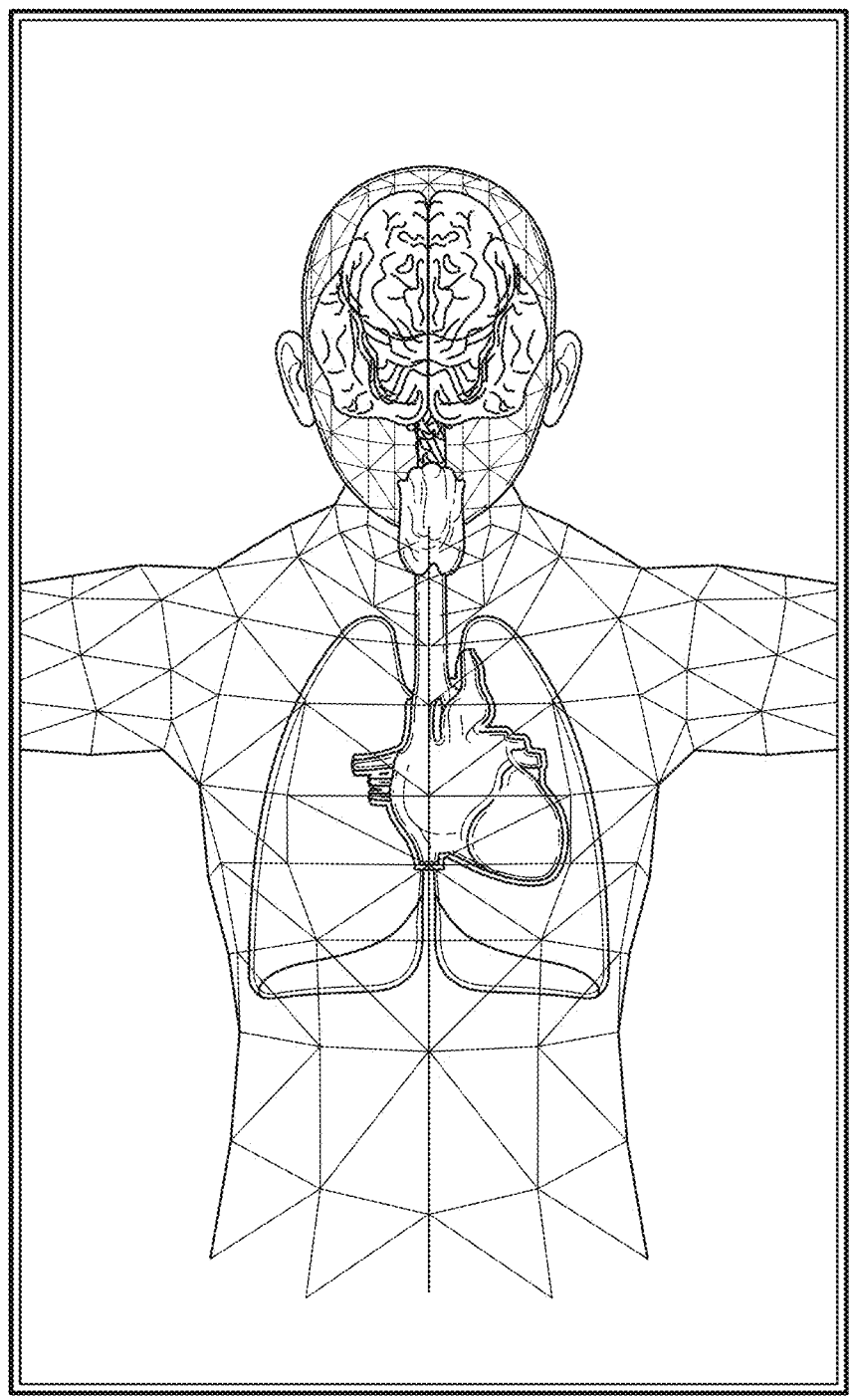
Figure 19E:
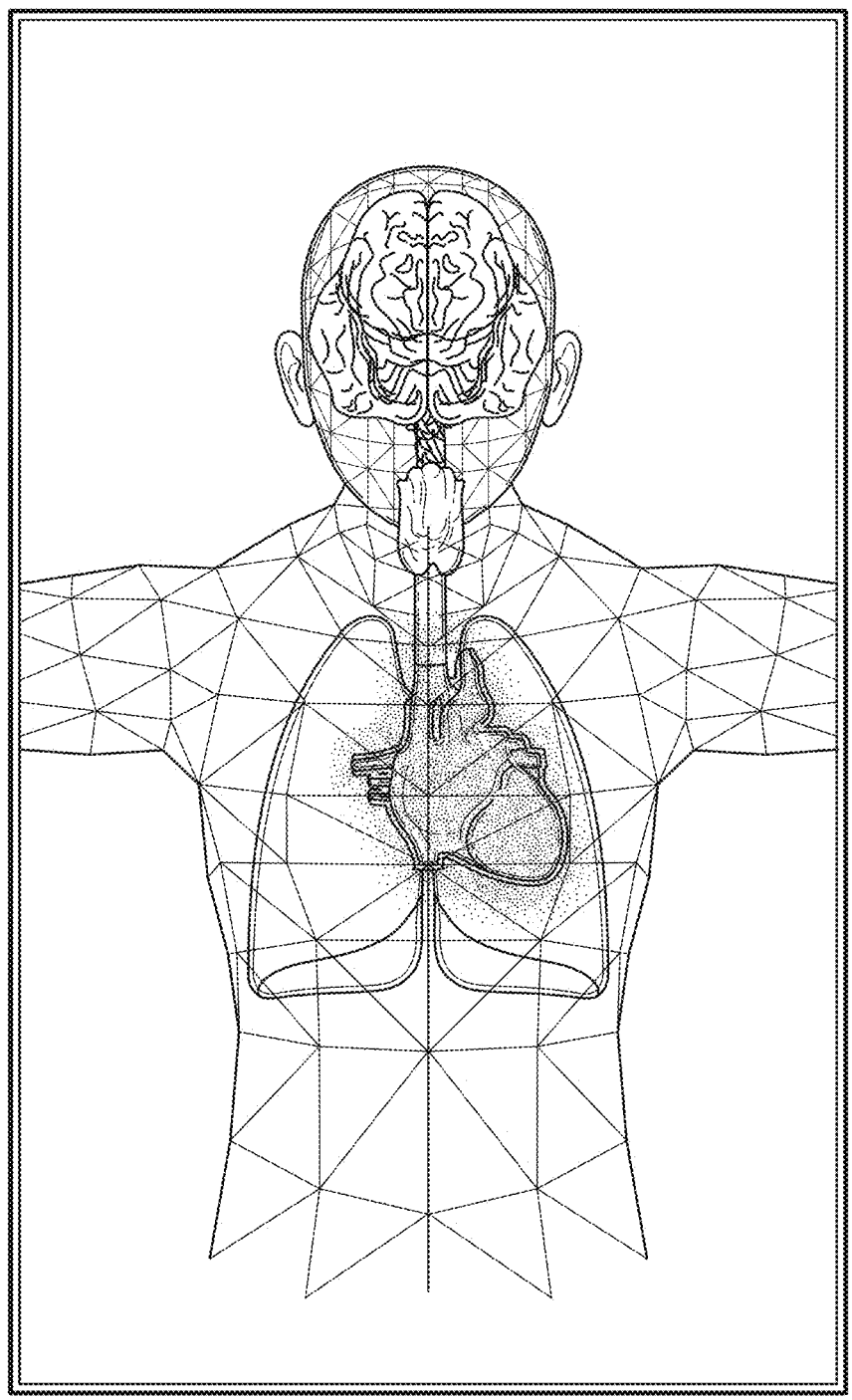

FIGS. 19D and 19E show the brain included in the emphasized body portions meaning that the hub 100 is receiving data relevant to brain functions, such as, for example, depth of sedation data or brain oximetry data. FIG. 19E additionally shows an alarming heart function similar to FIG. 19C.

Figure 19F:
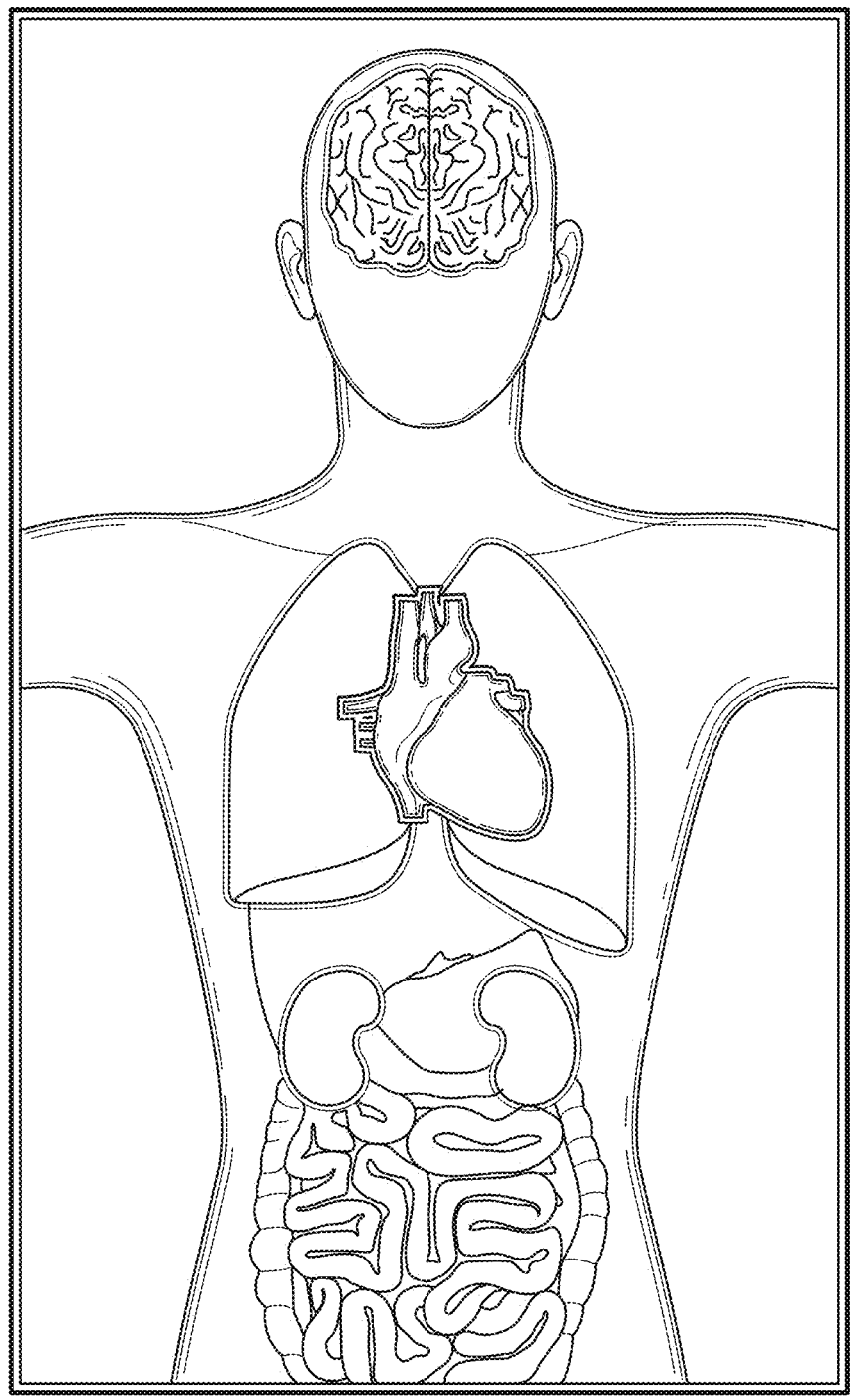
Figure 19G:
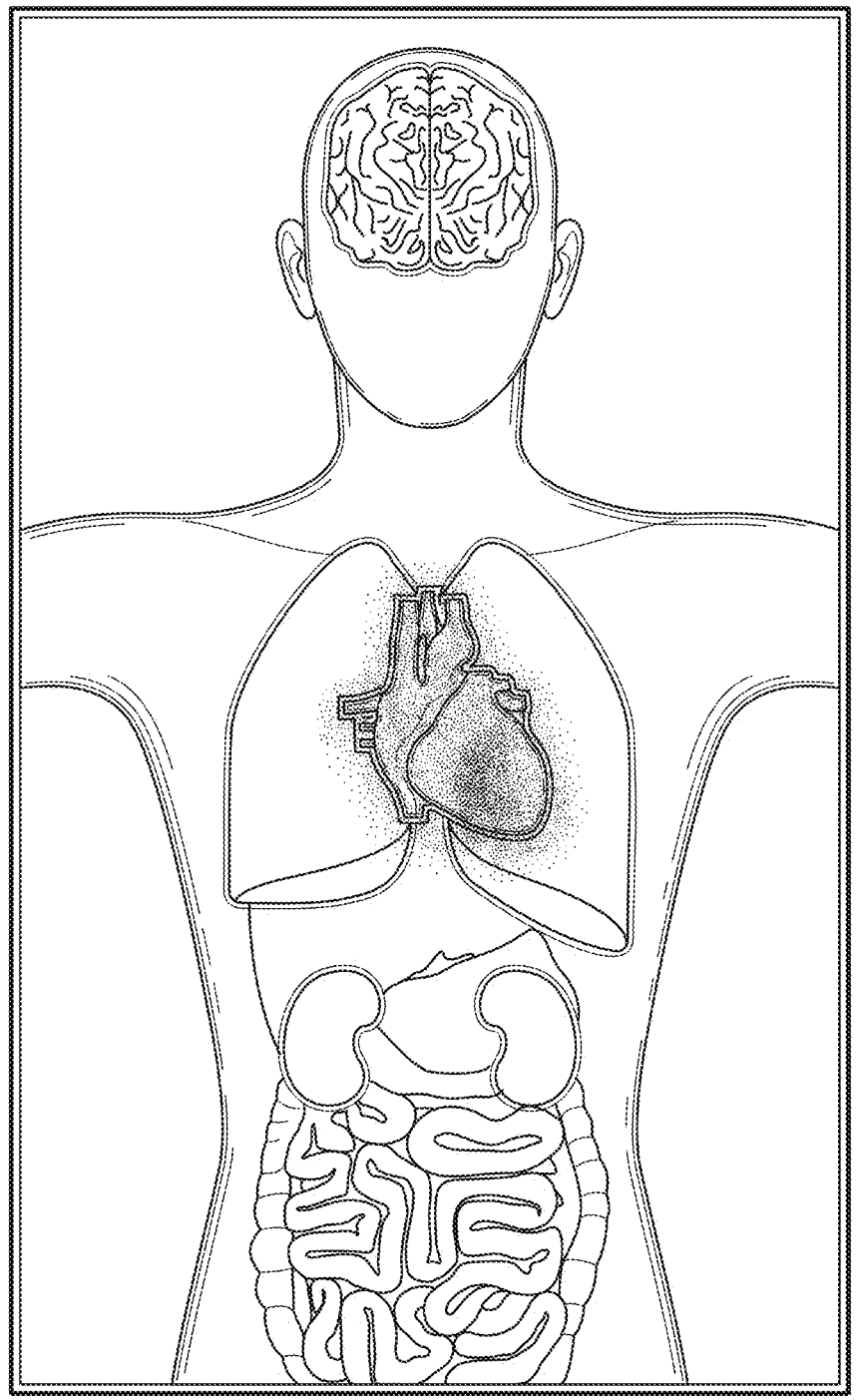
Figure 19H:
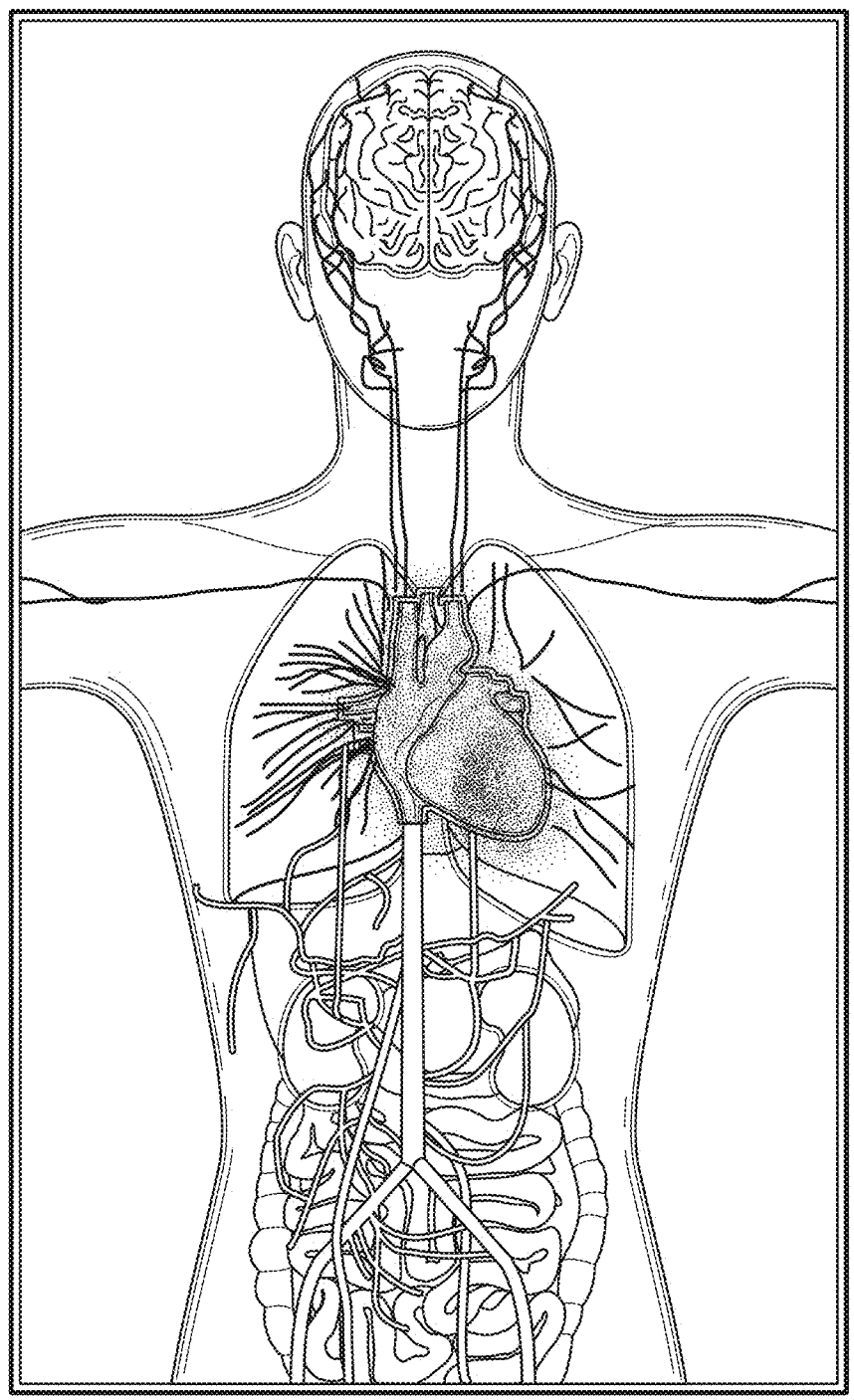
Figure 19I:
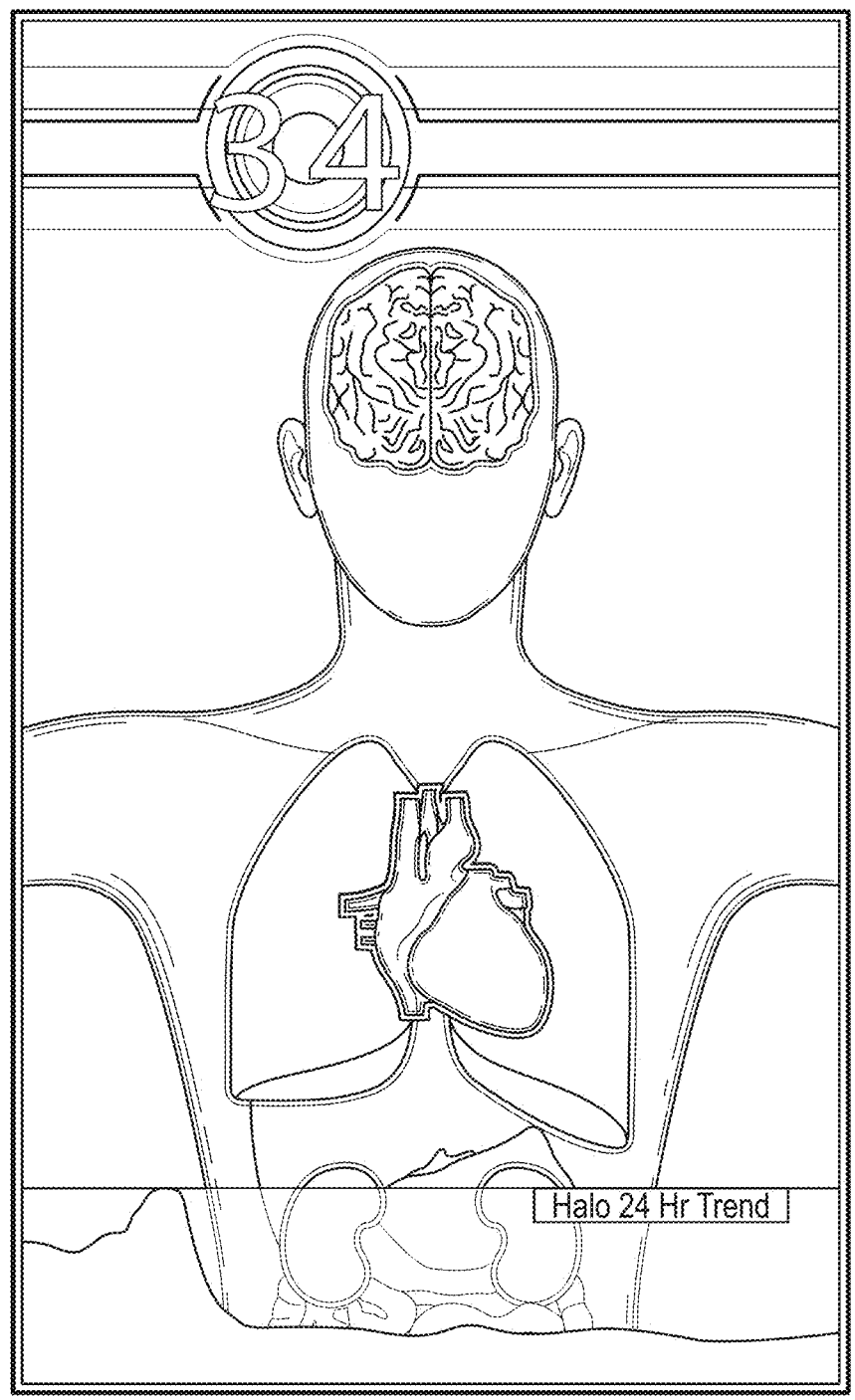
Figure 19J:
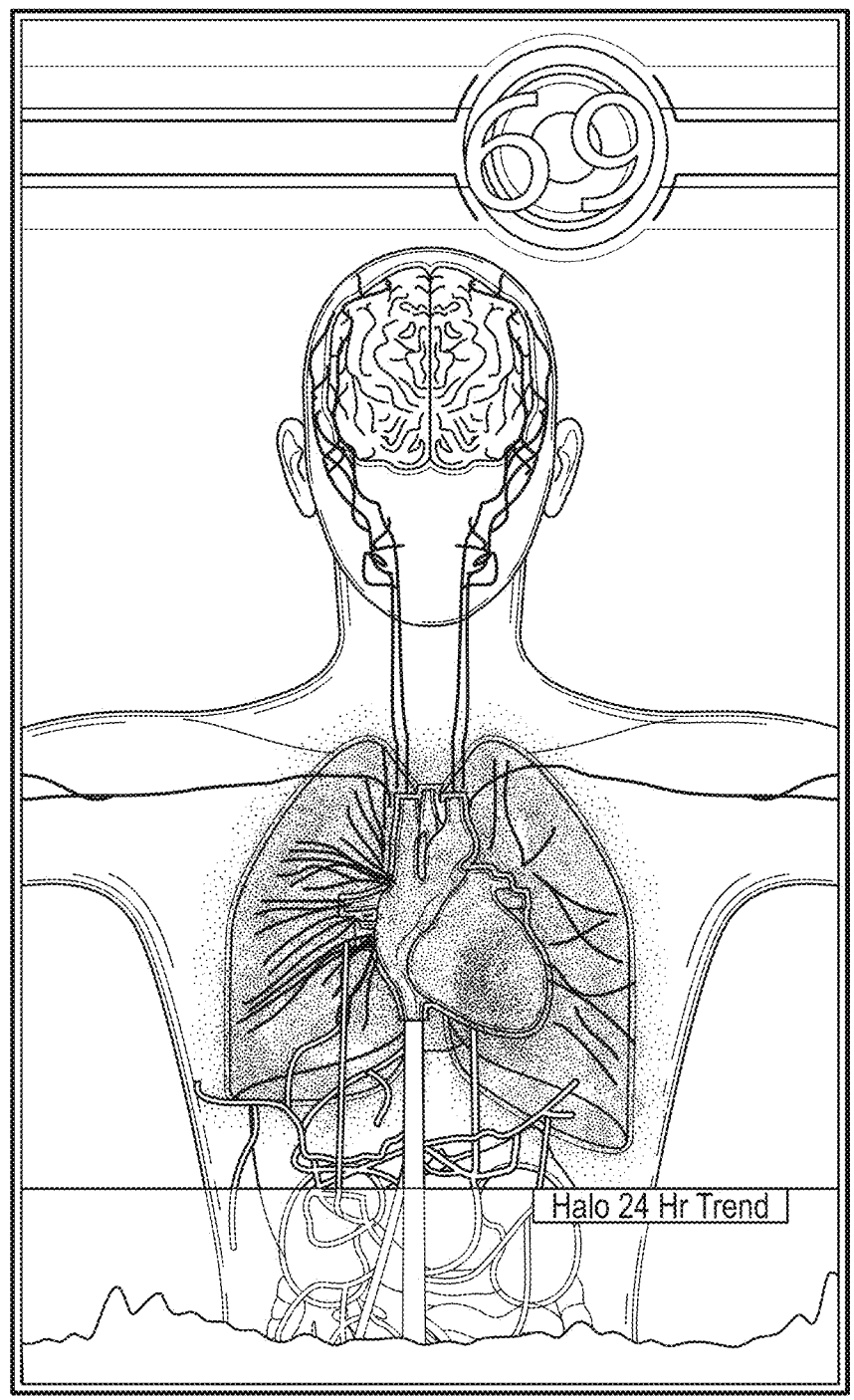

In FIG. 19F, additional organs, such as the kidneys are being monitored, but the respiratory system is not. In FIG. 19G, an alarming hear function is shown, and in FIG. 19H, an alarming circulatory system is being shown. FIG. 19I shows the wellness indication along with lungs, heart, brain and kidneys. FIG. 19J shows alarming lungs, heart, and circulatory system as well as the wellness indication. Moreover, FIG. 19J shows a severity contrast, such as, for example, the heart alarming red for urgent while the circulatory system alarms yellow for caution. An artisan will recognize other color schemes that are appropriate from the disclosure herein.

Figure 20A:
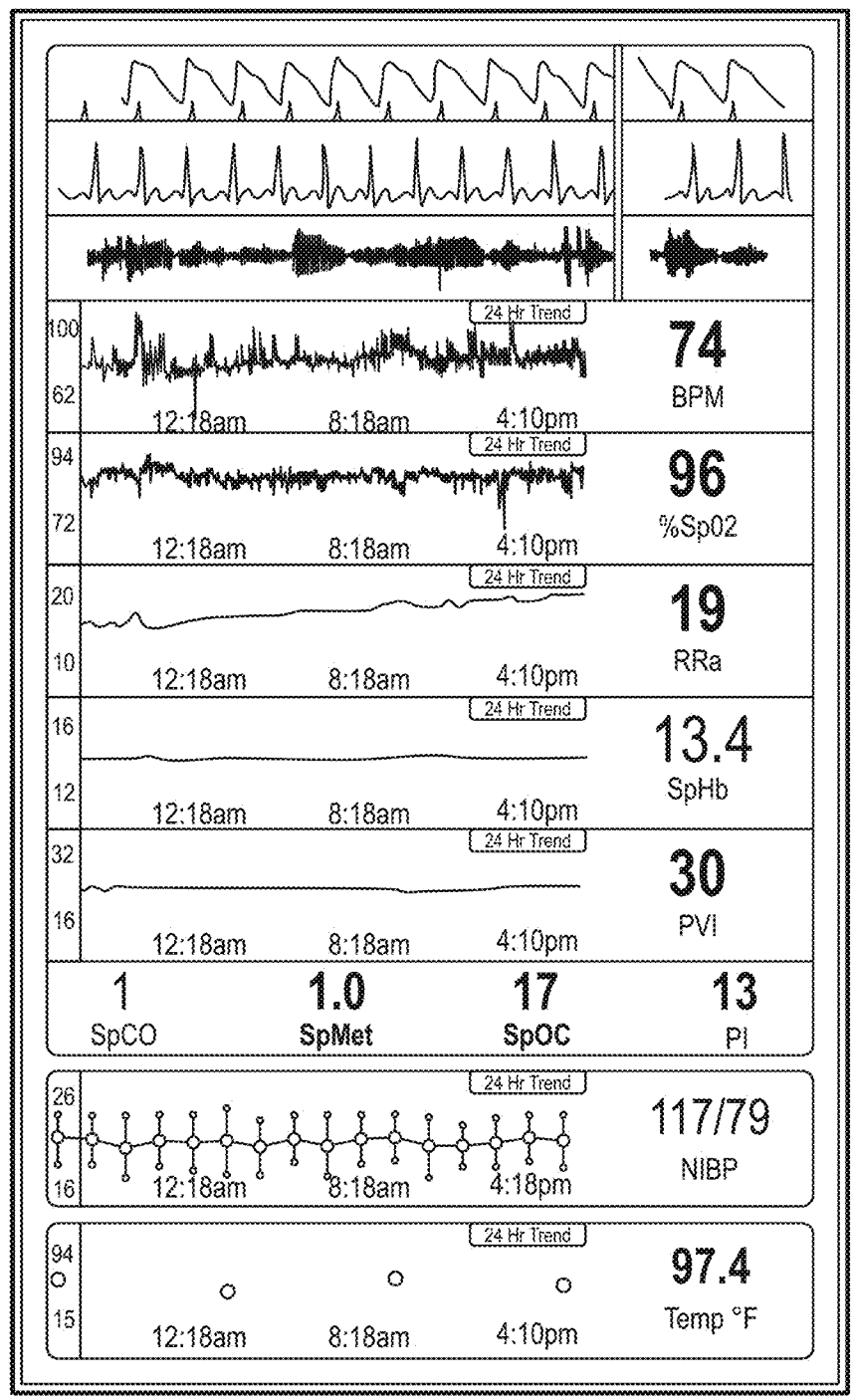
FIGS. 20A-20C illustrate exemplary displays of measurement data showing data separation and data overlap on a display of the hub of FIG. 1, respectively, according embodiments of the disclosure.
Figure 20B:
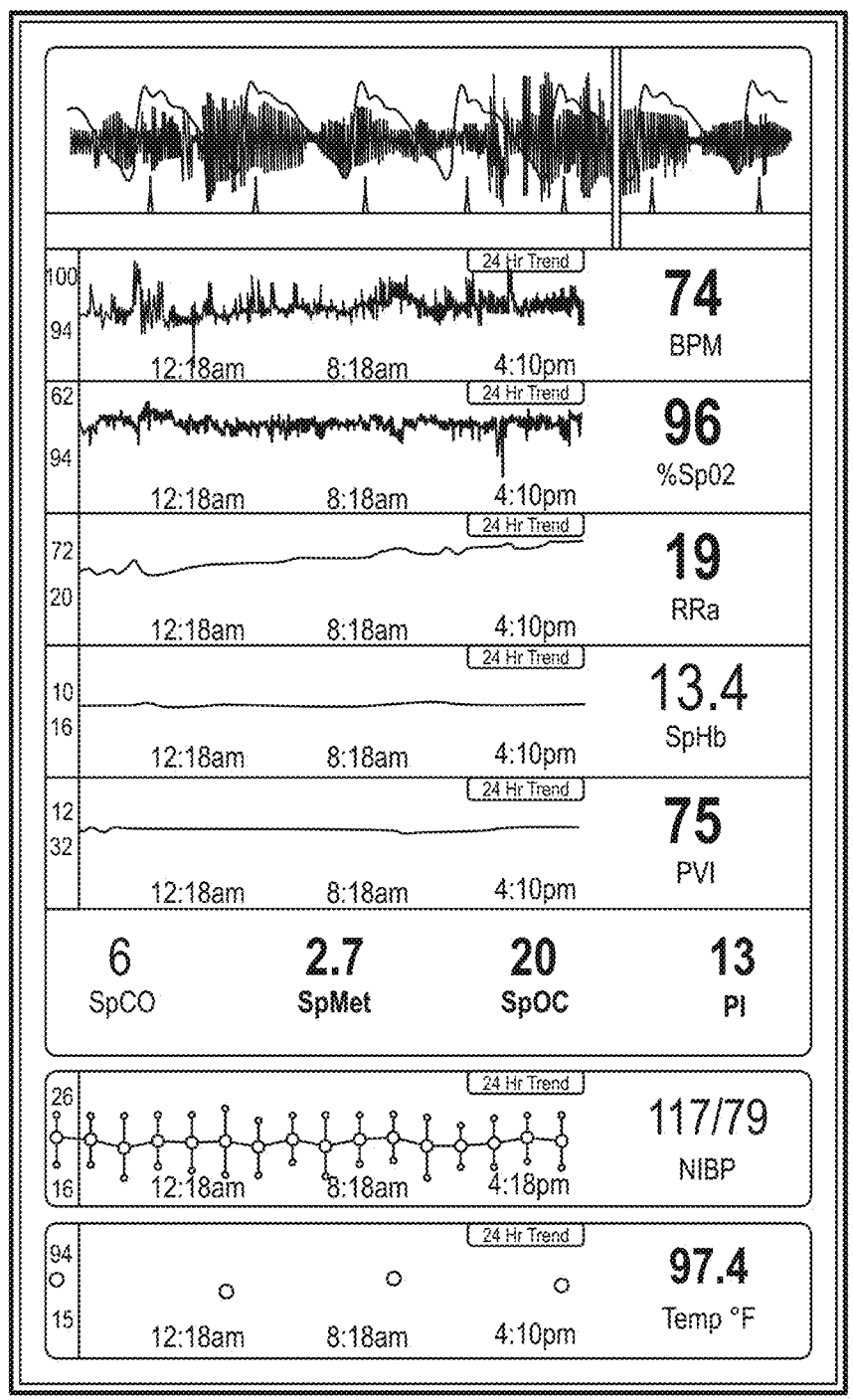
Figure 20C:
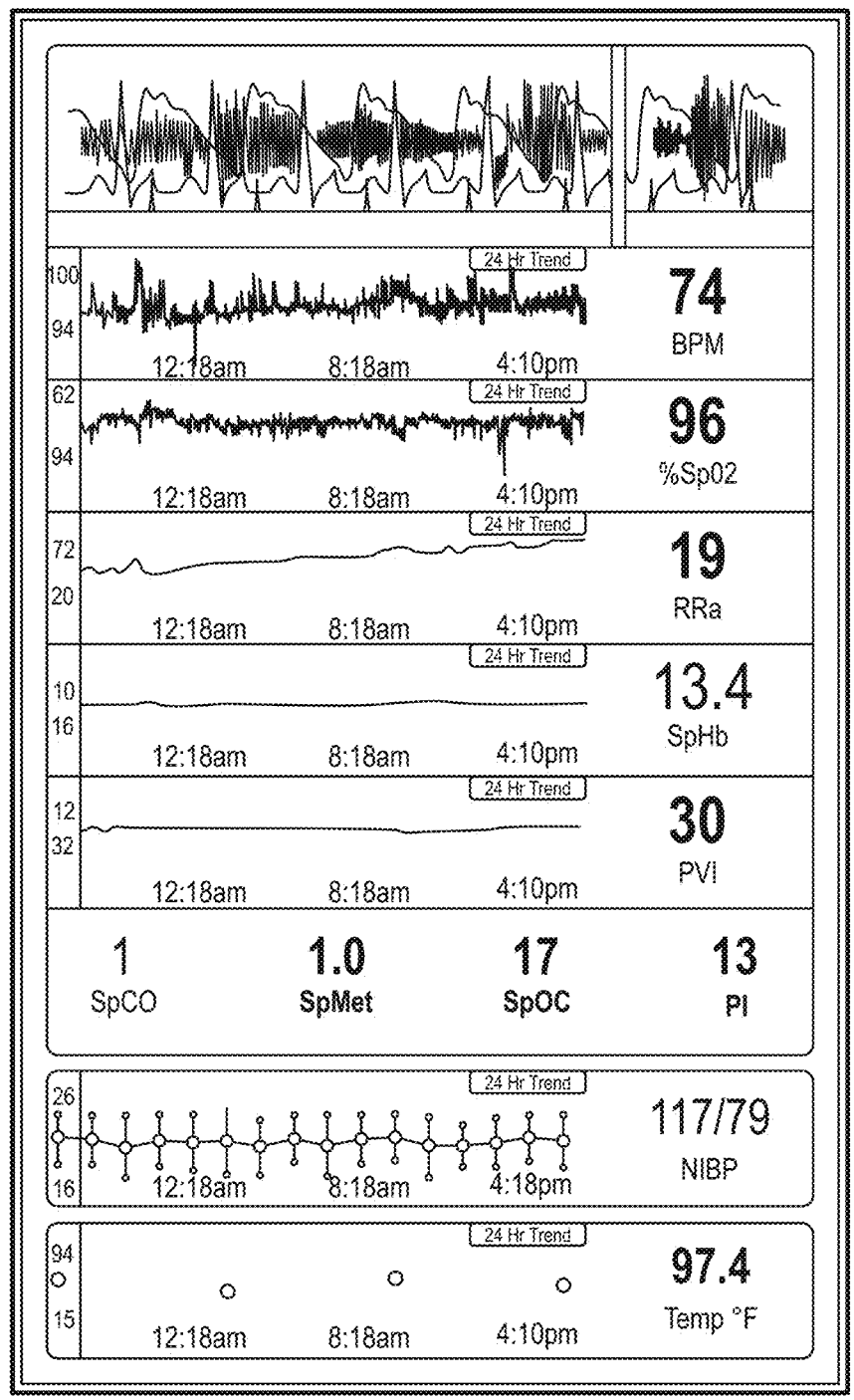
Figure 21A:
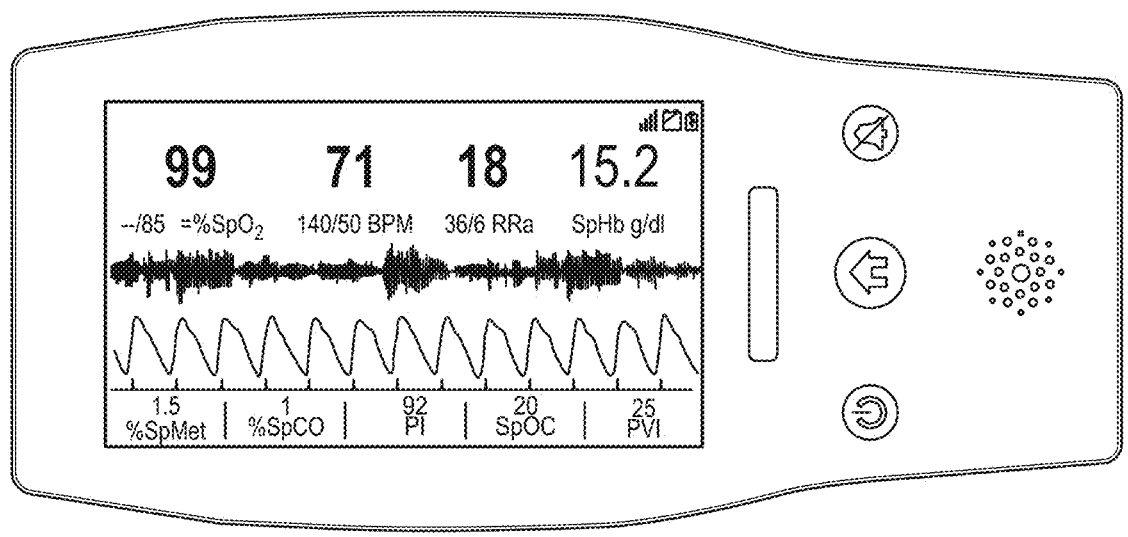
FIGS. 21A and 21B illustrate exemplary displays of measurement data showing data separation and data overlap on a display of the portable patient monitor of FIG. 1, respectively, according embodiments of the disclosure.
Figure 21B:
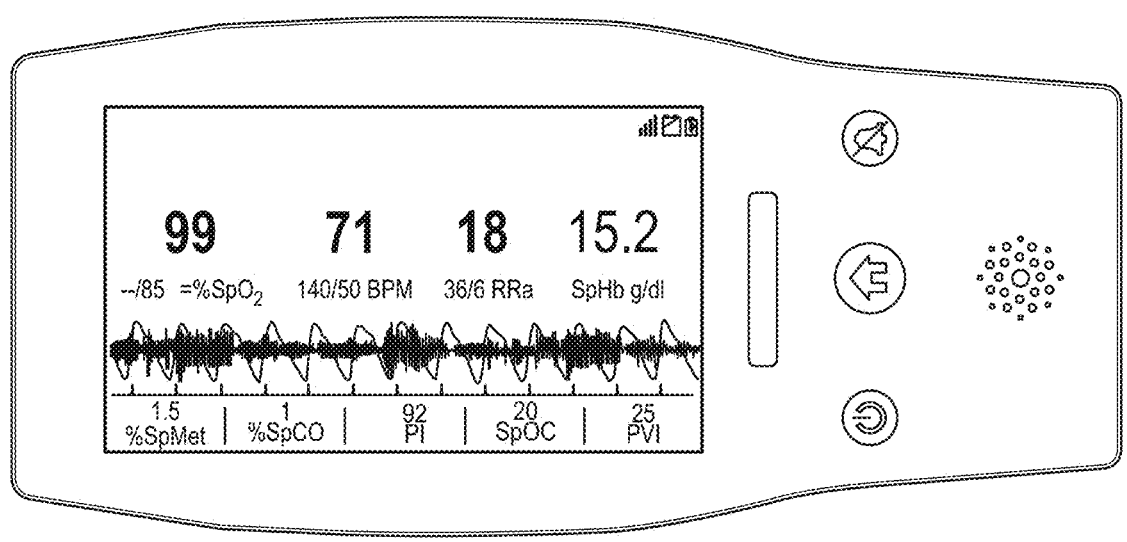

FIGS. 20A-20C illustrate exemplary displays of measurement data showing data separation and data overlap, respectively, according embodiments of the disclosure. FIGS. 21A and 21B illustrate exemplary displays of measurement data also showing data separation and data overlap, respectively, according embodiments of the disclosure.

For example, acoustic data from an acoustic sensor may advantageously provide breath sound data, while the plethysmograph and ECG or other signals can also be presented in separate waveforms (FIG. 20A, top of the screen capture). The monitor may determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases a system monitors other physiological sounds, such as heart rate to help with probe off detection, heart sounds (S1, S2, S3, S4, and murmurs), and change in heart sounds such as normal to murmur or split heart sounds indicating fluid overload.

Providing a visual correlation between multiple physiological signals can provide a number of valuable benefits where the signals have some observable physiological correlation. As one example of such a correlation, changes in morphology (e.g., envelope and/or baseline) of the plethysmographic signal can be indicative of patient blood or other fluid levels. And, these changes can be monitored to detect hypovolemia or other fluid-level related conditions. A pleth variability index may provide an indication of fluid levels, for example. And, changes in the morphology of the plethysmographic signal are correlated to respiration. For example, changes in the envelope and/or baseline of the plethysmographic signal are correlated to breathing. This is at least in part due to aspects of the human anatomical structure, such as the mechanical relationship and interaction between the heart and the lungs during respiration.

Thus, superimposing a plethysmographic signal and a respiratory signal (FIG. 20B) can give operators an indication of the validity of the plethysmographic signal or signals derived therefrom, such as a pleth variability index. For example, if bursts in the respiration signal indicative of inhalation and exhalation correlate with changes in peaks and valleys of the plethysmographic envelope, this gives monitoring personnel a visual indication that the plethysmographic changes are indeed due to respiration, and not some other extraneous factor. Similarly, if the bursts in the respiration signal line up with the peaks and valleys in the plethysmographic envelope, this provides monitoring personnel an indication that the bursts in the respiration signal are due to patient breathing sounds, and not some other non-targeted sounds (e.g., patient non-breathing sounds or non-patient sounds).

The monitor may also be configured to process the signals and determine whether there is a threshold level of correlation between the two signals, or otherwise assess the correlation. However, by additionally providing a visual indication of the correlation, such as by showing the signals superimposed with one another, the display provides operators a continuous, intuitive and readily observable gauge of the particular physiological correlation. For example, by viewing the superimposed signals, users can observe trends in the correlation over time, which may not be otherwise ascertainable.

The monitor can visually correlate a variety of other types of signals instead of, or in addition to plethysmographic and respiratory signals. For example, FIG. 20C depicts a screen shot of another example monitoring display. As shown in the upper right portion of FIG. 20C, the display superimposes a plethysmographic signal, an ECG signal, and a respiration signal. In other configurations, more than three different types of signals may be overlaid onto one another.

In one embodiment, the hub 100 nothing provides an interface through which the user can move the signals together to overlay on one another. For example, the user may be able to drag the respiration signal down onto the plethysmographic signal using a touch screen interface. Conversely, the user may be able to separate the signals, also using the touch screen interface. In another embodiment, the monitor includes a button the user can press, or some other user interface allowing the user to overlay and separate the signals, as desired. FIGS. 21A and 21B show similar separation and joining of the signals.

In certain configurations, in addition to providing the visual correlation between the plethysmographic signal and the respiratory signal, the monitor is additionally configured to process the respiratory signal and the plethysmographic signal to determine a correlation between the two signals. For example, the monitor may process the signals to determine whether the peaks and valleys in the changes in the envelope and/or baseline of the plethysmographic signal correspond to bursts in the respiratory signal. And, in response to the determining that there is or is not a threshold level of correlation, the monitor may provide some indication to the user. For example, the monitor may provide a graphical indication (e.g., a change in color of pleth variability index indicator), an audible alarm, or some other indication. The monitor may employ one or more envelope detectors or other appropriate signal processing componentry in making the determination.

In certain embodiments, the system may further provide an audible indication of the patient's breathing sounds instead of, or in addition to the graphical indication. For example, the monitor may include a speaker, or an earpiece (e.g., a wireless earpiece) may be provided to the monitoring personnel providing an audible output of the patient sounds. Examples of sensors and monitors having such capability are described in U.S. Pat. Pub. No. 2011/0172561 and are incorporated by reference herein.

In addition to the above described benefits, providing both the acoustic and plethysmographic signals on the same display in the manner described can allow monitoring personnel to more readily detect respiratory pause events where there is an absence of breathing, high ambient noise that can degrade the acoustic signal, improper sensor placement, etc.

Figure 22A:
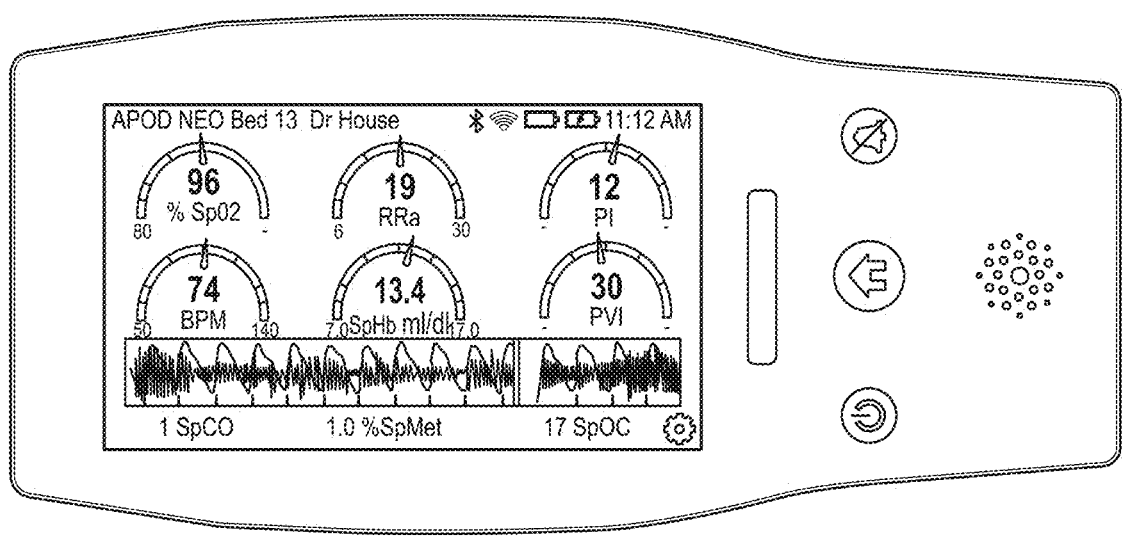
FIGS. 22A and 22B illustrate exemplary analog display indicia according to an embodiment of the disclosure.
Figure 22B:
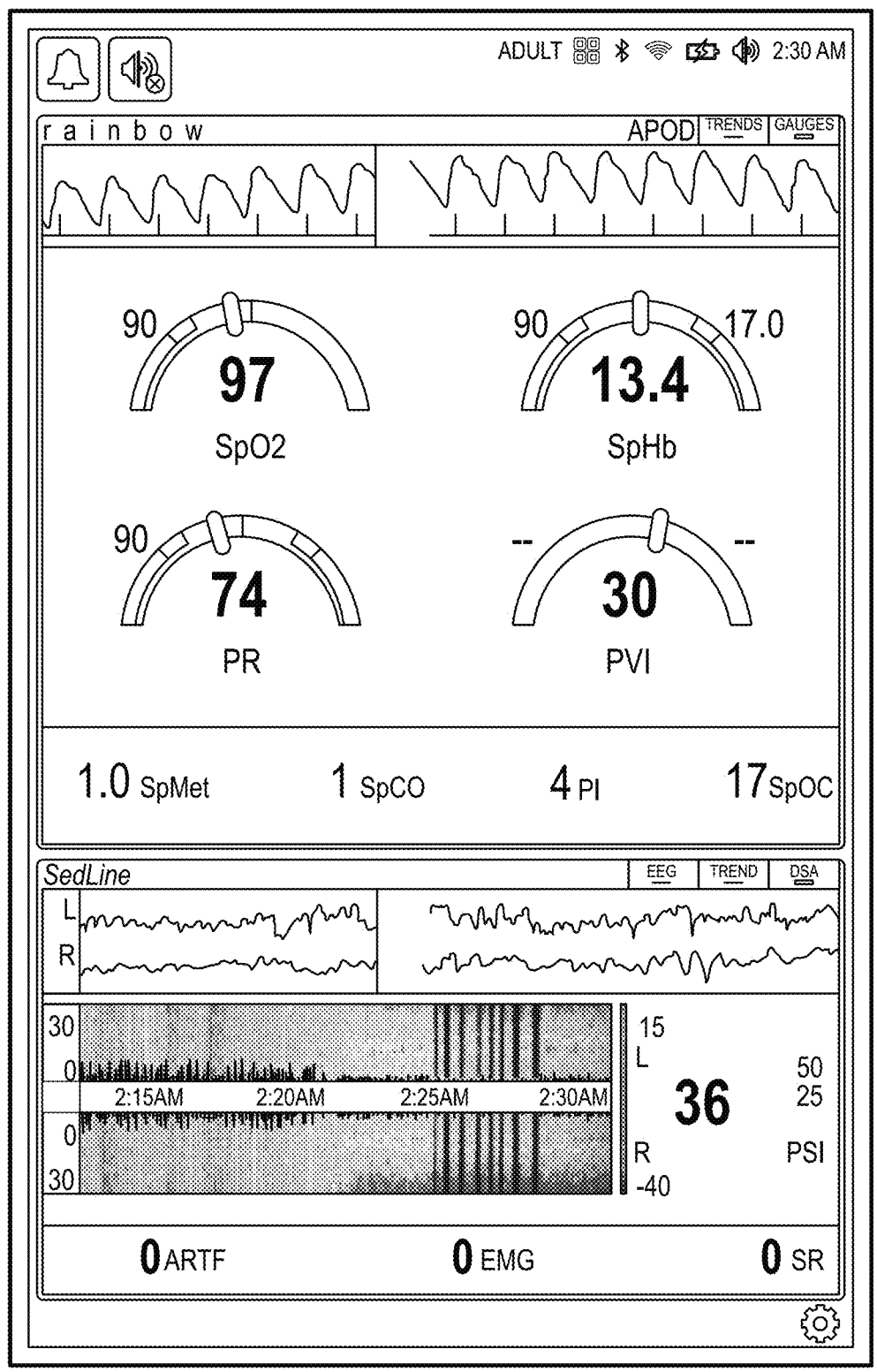

FIGS. 22A-22B illustrate exemplary analog display indicia, according to an embodiment of the disclosure. As shown in FIGS. 22A and 22B, the screen shots displays health indicators of various physiological parameters, in addition to other data. Each health indicator can include an analog indicator and/or a digital indicator. In embodiments where the health indicator includes an analog and a digital indicator, the analog and digital indicators can be positioned in any number of formations, such as side-by-side, above, below, transposed, etc. In the illustrated embodiment, the analog indicators are positioned above and to the sides of the digital indicators. As shown more clearly in FIG. 22B, the analog displays may include colored warning sections, dashes indicating position on the graph, and digital information designating quantitate information form the graph. In FIG. 22B, for example, the pulse rate PR graph shows that from about 50 to about 140 beats per minute, the graph is either neutral or beginning to be cautionary, whereas outside those numbers the graph is colored to indicate a severe condition. Thus, as the dash moves along the arc, a caregiver can readily see where in the range of acceptable, cautionary, and extreme the current measurements fall.

Each analog indicator of the health indicator can include a dial that moves about an arc based on measured levels of monitored physiological parameters. As the measured physiological parameter levels increase the dial can move clockwise, and as the measured physiological parameter levels decrease, the dial can move counter-clockwise, or vice versa. In this way, a user can quickly determine the patient's status by looking at the analog indicator. For example, if the dial is in the center of the arc, the observer can be assured that the current physiological parameter measurements are normal, and if the dial is skewed too far to the left or right, the observer can quickly assess the severity of the physiological parameter levels and take appropriate action. In other embodiments, normal parameter measurements can be indicated when the dial is to the right or left, etc.

In some embodiments, the dial can be implemented as a dot, dash, arrow, or the like, and the arc can be implemented as a circle, spiral, pyramid, or other shape, as desired. Furthermore, the entire arc can be lit up or only portions of the arc can be lit up based on the current physiological parameter measurement level. Furthermore, the arc can turn colors or be highlighted based on the current physiological parameter level. For example, as the dial approaches a threshold level, the arc and/or dial can turn from green, to yellow, to red, shine brighter, flash, be enlarged, move to the center of the display, or the like.

Different physiological parameters can have different thresholds indicating abnormal conditions. For example, some physiological parameters may upper a lower threshold levels, while others only have an upper threshold or a lower threshold. Accordingly, each health indicator can be adjusted based on the physiological parameter being monitored. For example, the SpO2 health indicator can have a lower threshold that when met activates an alarm, while the respiration rate health indicator can have both a lower and upper threshold, and when either is met an alarm is activated. The thresholds for each physiological parameter can be based on typical, expected thresholds and/or user-specified thresholds.

The digital indicator can provide a numerical representation of the current levels of the physiological parameter the digital indicator may indicate an actual level or a normalized level and can also be used to quickly asses the severity of a patient condition. In some embodiments, the display includes multiple health indicators for each monitored physiological parameter. In certain embodiments, the display includes fewer health indicators than the number of monitored physiological parameters. In such embodiments, the health indicators can cycle between different monitored physiological parameters.

Figure 23A:
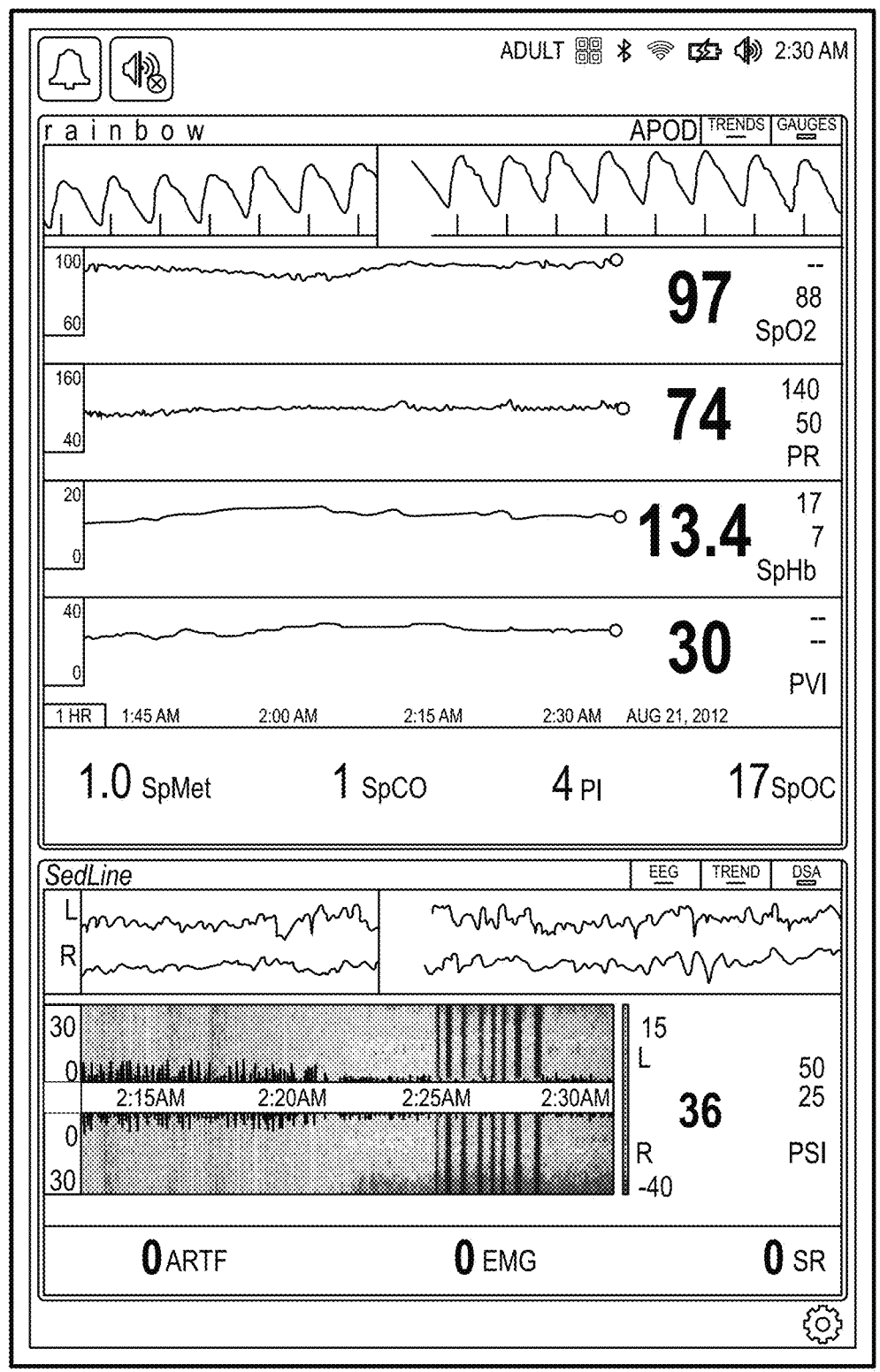
FIGS. 23A-23F illustrate exemplary displays of measurement data showing, for example, data presentation in FIGS. 23A-23D when a depth of consciousness monitor is connected to a channel port of the hub of FIG. 1, data presentation in FIG. 23E when temperature and blood pressure sensors communicate with the hub of FIG. 1 and data presentation in FIG. 23F when an acoustic sensor is also communicating with the hub of FIG. 1, according embodiments of the disclosure.
Figure 23B:
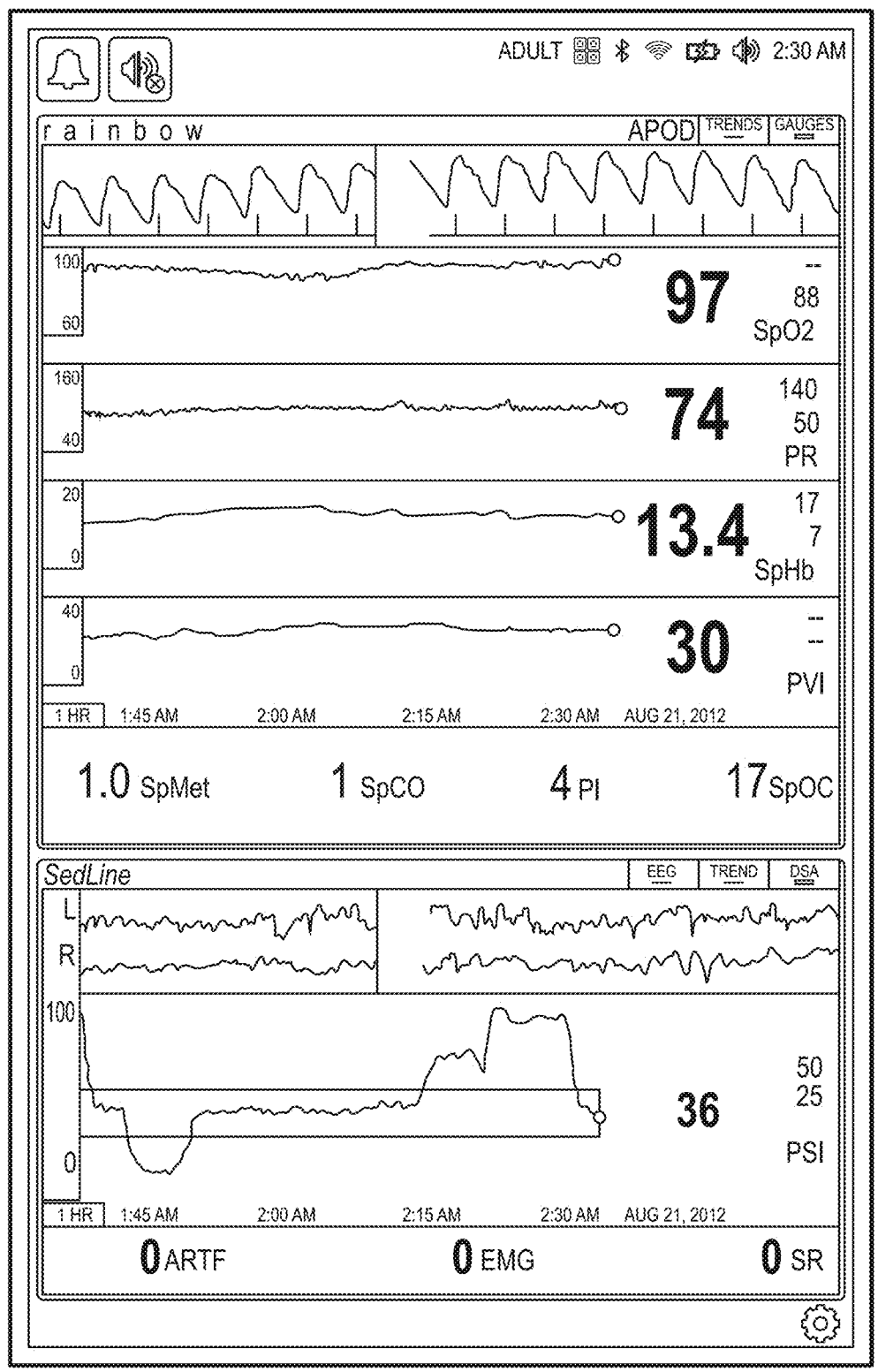
Figure 23C:
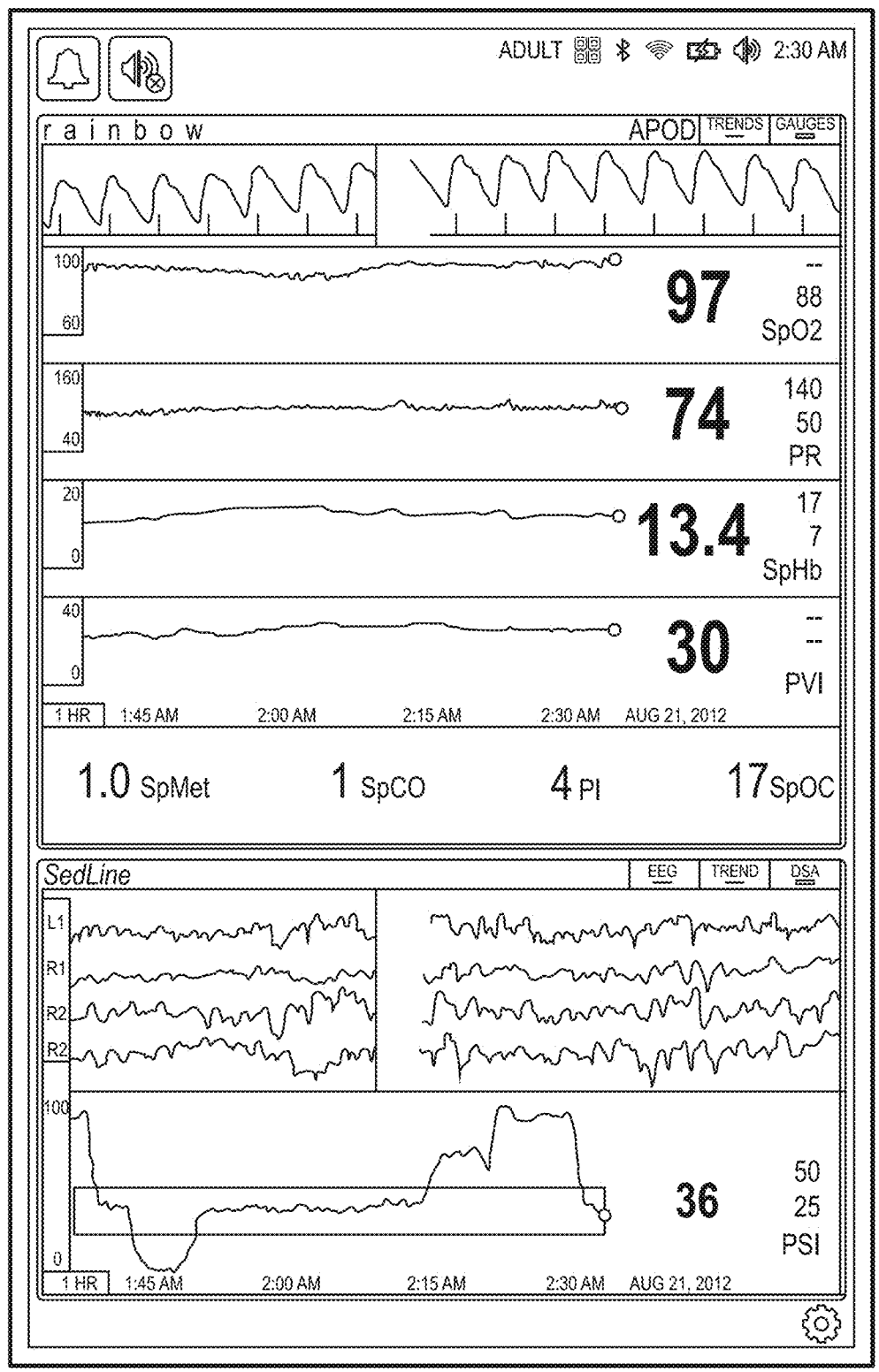
Figure 23D:
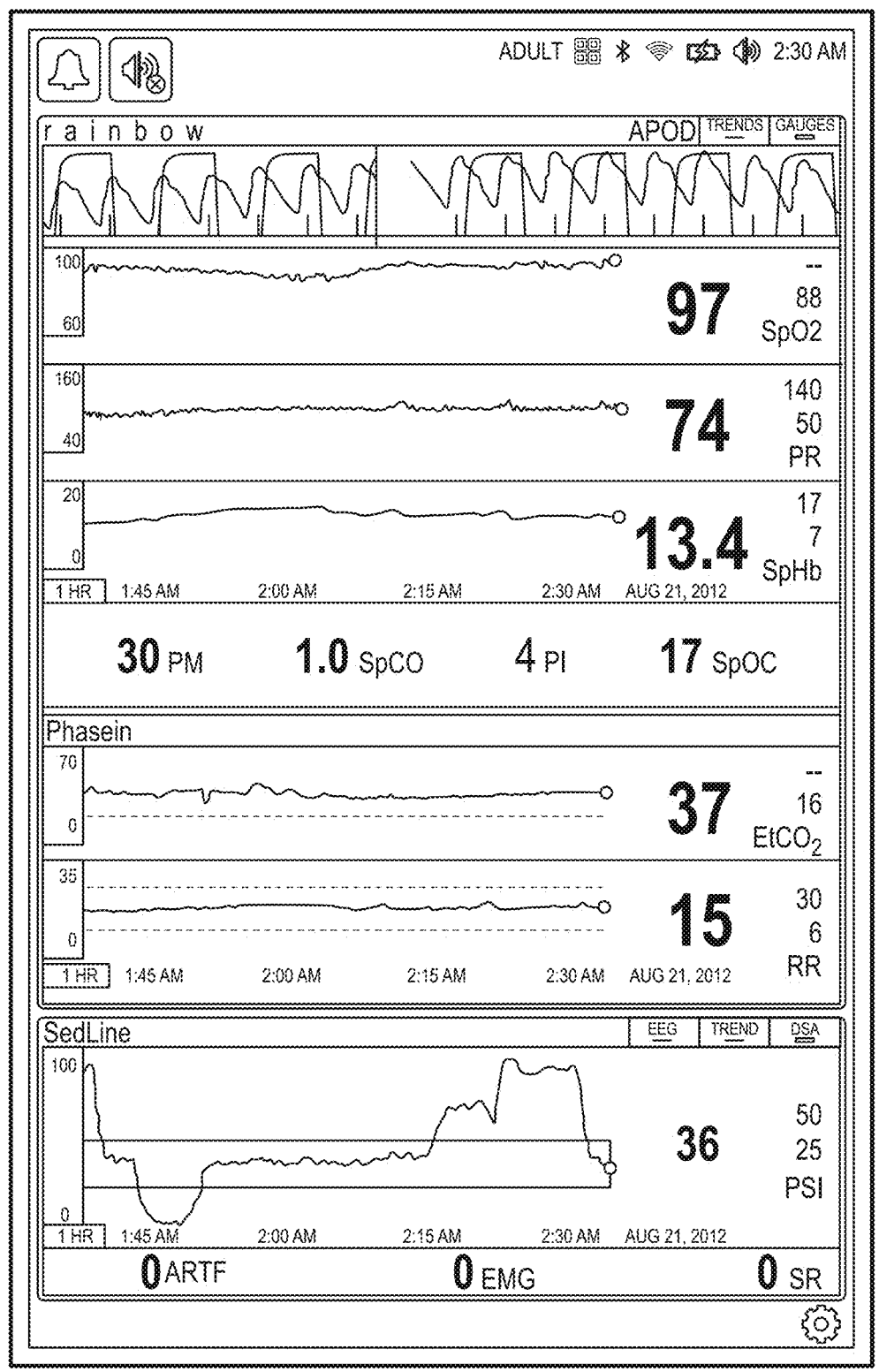
Figure 23E:
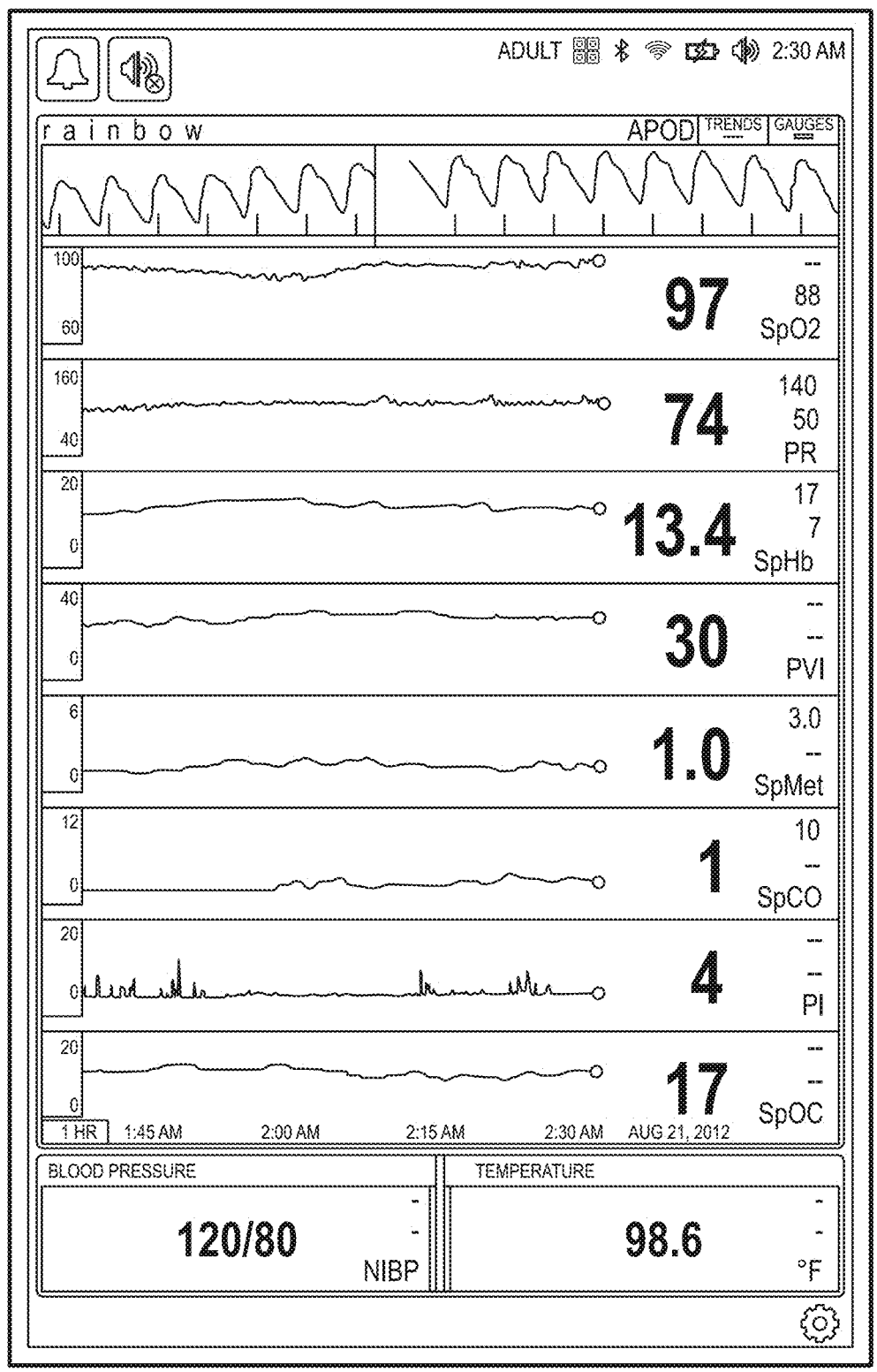
Figure 23F:
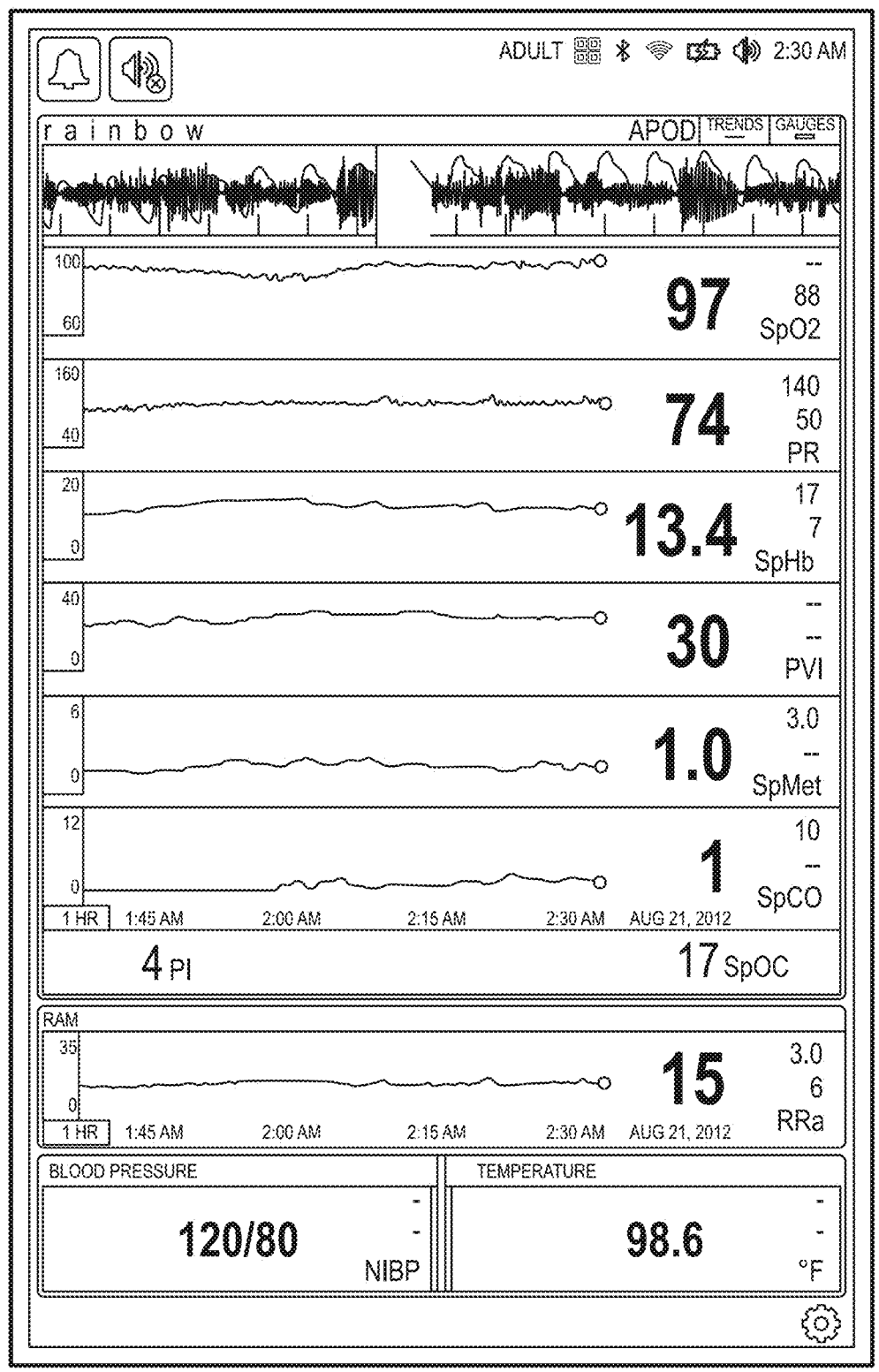

FIGS. 23A-23F illustrate exemplary displays of measurement data showing, for example, data presentation in FIGS. 23A-23D when a depth of consciousness monitor is connected to a channel port of the hub of FIG. 1. As shown in FIGS. 23A-23C, the hub 100 advantageously roughly bifurcates its display 104 to show various information from the, for example, SEDLine device, commercially available from Masimo Corp. of Irvine, Calif. In FIG. 23D, the hub 100 includes an attached PhaseIn device, commercially available by PHASEIN AB of Sweden, providing, for example, information about the patient's respiration. The hub 100 also includes the SEDLine information, so the hub 100 has divided the display 104 appropriately. In FIG. 23E, temperature and blood pressure sensors communicate with the hub of FIG. 1 and the hub 100 creates display real estate appropriate for the same. In FIG. 23F, an acoustic sensor is also communicating with the hub of FIG. 1, as well as the forgoing blood pressure and temperature sensor. Accordingly, the hub 100 adjust the display real estate to accommodate the data from each attached device.

The term "and/or" herein has its broadest least limiting meaning which is the disclosure includes A alone, B alone, both A and B together, or A or B alternatively, but does not require both A and B or require one of A or one of B. As used herein, the phrase at least one of A, B, and C should be construed to mean a logical A or B or C, using a non-exclusive logical or.

The term "plethysmograph" includes it ordinary broad meaning known in the art which includes data responsive to changes in volume within an organ or whole body (usually resulting from fluctuations in the amount of blood or air it contains).

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A method of associating data from disparate medical devices with a patient being monitored, the method comprising:

receiving a designation of a patient on a patient monitoring hub;

receiving data at the patient monitoring hub from a plurality of disparate medical devices, each disparate medical device monitoring the patient or associated with the patient at a monitoring facility, wherein receiving data comprises:

receiving data for a first time from a first disparate medical device via a connector of the first disparate medical device that is connected to a medical port of the patient monitoring hub, wherein the first disparate medical device provides data in a first format, and wherein, prior to connection of the first disparate medical device to the patient monitoring hub, the first format was not known to the patient monitoring hub; and receiving configuration information from a memory of the connector of the first disparate medical device, wherein the configuration information comprises at least information specifying the first format, and wherein the configuration information further comprises at least information specifying a device delay time;

configuring the patient monitoring hub, using the configuration information, to understand the first format without upgrading software on the patient monitoring hub or the first disparate medical device;

synchronizing, using the configuration information specifying the device delay time, the data from the first disparate medical device with data received from others of the plurality of disparate medical devices; and associating the data, including the synchronized data from the first disparate medical device and the data received from others of the plurality of disparate medical devices, with the patient.

2. The method of claim 1, wherein receiving the designation comprises receiving a selection from a list of patients at the monitoring facility, the list acquired from one or more electronic devices of the monitoring facility.

3. The method of claim 1 further comprising:
outputting the data associated with the patient to a medical server.

4. The method of claim 1, wherein the patient monitoring hub comprises a display.

5. The method of claim 4 further comprising:
displaying, on the display, one or more physiological parameter measurements determined based at least in part on the data associated with the patient.

6. A patient monitoring hub comprising:
one or more processors configured to execute instructions in order to:
receive a designation of a patient on the patient monitoring hub;
receive data from a plurality of disparate medical devices, each disparate medical device monitoring the patient or associated with the patient at a monitoring facility, wherein receiving data comprises:
receiving data for a first time from a first disparate medical device via a connector of the first disparate medical device that is connected to a medical port of the patient monitoring hub, wherein the first disparate medical device provides data in a first format, and wherein; prior to connection of the first disparate medical device to the patient monitoring hub, the first format was not known to the patient monitoring hub; and receiving configuration information from a memory of the connector of the first disparate medical device, wherein the configuration information comprises at least information specifying the first format, and wherein the configuration information further comprises at least information specifying a device delay time;

configure the patient monitoring hub medical device using the configuration information, to understand the first format without upgrading software on the patient monitoring hub medical device or the first disparate medical device;

synchronize, using the configuration information specifying the device delay time, the data from the first disparate medical device with data received from others of the plurality of disparate medical devices; and associate the data, including the synchronized data from the first disparate medical device and the data received from others of the plurality of disparate medical devices, with the patient.

7. The patient monitoring hub of claim 6, wherein receiving the designation comprises receiving a selection from a list of patients at the monitoring facility, the list acquired from the monitoring facility's electronic devices.

8. The patient monitoring hub of claim 6, wherein the one or more processors are further configured to execute instructions in order to:

output the data associated with the patient to a medical server.

9. The patient monitoring hub of claim 6 further comprising:

a display.

10. The patient monitoring hub of claim 9, wherein the one or more processors are configured to execute instructions in order to further:

display, on the display, one or more physiological parameter measurements determined based at least in part on the data associated with the patient.

* * * * *

UNITED STATES PATENT AND TRADEMARK OFFICE
CERTIFICATE OF CORRECTION

PATENT NO. : 10,925,550 B2  
APPLICATION NO. : 15/214276  
DATED : February 23, 2021  
INVENTOR(S) : Ammar Al-Ali Page 1 of 1

It is certified that error appears in the above-identified patent and that said Letters Patent is hereby corrected as shown below:

In the Claims

Column 20 Line 64, Claim 6, change "wherein;" to --wherein,--.

Column 21 Lines 8-12, Claim 6, change "configure the patient monitoring hub medical device using the configuration information, to understand the first format without upgrading software on the patient monitoring hub medical device or the first disparate medical device;" to --configure the patient monitoring hub, using the configuration information, to understand the first format without upgrading software on the patient monitoring hub or the first disparate medical device;--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*